(12) United States Patent
Fitzgibbons et al.

(10) Patent No.: US 12,220,229 B2
(45) Date of Patent: *Feb. 11, 2025

(54) RADAR SENSORS FOR PATIENT MONITORING

(71) Applicant: Hill-Rom Services, Inc., Batesville, IN (US)

(72) Inventors: Stacey A. Fitzgibbons, DeWitt, NY (US); David L. Ribble, Indianapolis, IN (US); Eric R. Meyer, Batesville, IN (US); Michael S. Hood, Batesville, IN (US); Gregory J. Shannon, Indianapolis, IN (US); Yue Wang, Columbus, IN (US); Charles A. Lachenbruch, Batesville, IN (US); Steven D. Baker, Beaverton, OR (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/539,742

(22) Filed: Dec. 14, 2023

(65) Prior Publication Data
US 2024/0122502 A1 Apr. 18, 2024

Related U.S. Application Data

(63) Continuation of application No. 17/151,889, filed on Jan. 19, 2021, now Pat. No. 11,877,844.
(Continued)

(51) Int. Cl.
A61B 5/11 (2006.01)
A61B 5/00 (2006.01)
(Continued)

(52) U.S. Cl.
CPC .............. *A61B 5/1113* (2013.01); *A61B 5/05* (2013.01); *A61B 5/08* (2013.01); *A61B 5/113* (2013.01);
(Continued)

(58) Field of Classification Search
None
See application file for complete search history.

(56) References Cited

U.S. PATENT DOCUMENTS 5,560,374 A 10/1996 Viard
5,625,914 A 5/1997 Schwab
(Continued)

FOREIGN PATENT DOCUMENTS

JP 2000118338 A 4/2000
JP 2006226847 A 8/2006
(Continued)

OTHER PUBLICATIONS

First Chinese Office Action for Application No. 2021101844040, Dated Mar. 25, 2024, With English Translation (12 Pages).
(Continued)

*Primary Examiner* — Meredith Weare
(74) *Attorney, Agent, or Firm* — Barnes & Thornburg LLP

(57) ABSTRACT

One or more radar sensors can be used to monitor patients in a variety of different environments and embodiments. In one embodiment, radar sensors can be used to monitor a patient's breathing, including monitoring of tidal volume, chest expansion distance, breathing rate, etc. In another embodiment, a patient position can be monitored in a patient bed, which can be used as feedback for control of bladders of a patient bed. Additional embodiments are described herein.

18 Claims, 24 Drawing Sheets

Related U.S. Application Data

(60) Provisional application No. 62/978,481, filed on Feb. 19, 2020.

(51) Int. Cl.

| | | |
|---|---|---|
| *A61B 5/05* | (2021.01) | |
| *A61B 5/08* | (2006.01) | |
| *A61B 5/113* | (2006.01) | |
| *A61G 7/057* | (2006.01) | |
| *A61G 7/10* | (2006.01) | |

(52) U.S. Cl.
CPC ........ *A61B 5/6891* (2013.01); *A61G 7/05769* (2013.01); *A61G 7/1021* (2013.01)

(56) References Cited

U.S. PATENT DOCUMENTS

| | | | |
|---|---|---|---|
| 5,963,130 | A | 10/1999 | Schlager et al. |
| 6,009,580 | A | 1/2000 | Caminade et al. |
| 6,034,526 | A | 3/2000 | Montant et al. |
| 6,079,068 | A | 6/2000 | Viard |
| 6,244,272 | B1 | 6/2001 | Montant et al. |
| 6,518,889 | B2 | 2/2003 | Schlager et al. |
| 6,560,804 | B2 | 5/2003 | Wise et al. |
| 7,515,059 | B2 | 4/2009 | Price et al. |
| 7,676,872 | B2 | 3/2010 | Block et al. |
| 7,973,666 | B2 | 7/2011 | Petrosenko et al. |
| 8,026,840 | B2 | 9/2011 | Dwelly et al. |
| 8,281,433 | B2 | 10/2012 | Riley et al. |
| 8,352,015 | B2 | 1/2013 | Bernstein et al. |
| 8,428,696 | B2 | 4/2013 | Foo |
| 8,454,528 | B2 | 6/2013 | Yuen et al. |
| 8,525,679 | B2 | 9/2013 | Riley et al. |
| 8,740,793 | B2 | 6/2014 | Cuddihy et al. |
| 8,750,971 | B2 | 6/2014 | Tran |
| 8,781,563 | B2 | 7/2014 | Foo |
| 9,002,427 | B2 | 4/2015 | Tupin, Jr. et al. |
| 9,022,032 | B2 | 5/2015 | Holzrichter |
| 9,468,307 | B2 | 10/2016 | Lafleche et al. |
| 9,526,437 | B2 | 12/2016 | Tupin, Jr. et al. |
| 9,549,691 | B2 | 1/2017 | Tran |
| 9,775,758 | B2 | 10/2017 | Riley et al. |
| 9,993,166 | B1 | 6/2018 | Johnson et al. |
| 10,318,809 | B2 | 6/2019 | Schultz et al. |
| 10,548,476 | B2 | 2/2020 | Lane et al. |
| 10,912,693 | B2 | 2/2021 | Baker et al. |
| 11,877,844 | B2 * | 1/2024 | Fitzgibbons ............ G16H 20/30 |
| 12,042,268 | B2 * | 7/2024 | Baker ................. A61B 5/0507 |
| 2004/0210155 | A1 * | 10/2004 | Takemura ................ A61B 5/00 702/159 |
| 2007/0070684 | A1 * | 3/2007 | Poulos ............... A61G 7/05776 365/149 |
| 2010/0101022 | A1 * | 4/2010 | Riley ..................... A61B 5/024 702/19 |
| 2010/0130873 | A1 | 5/2010 | Yuen et al. |
| 2010/0152600 | A1 * | 6/2010 | Droitcour ............ A61B 5/7221 600/534 |
| 2010/0240999 | A1 | 9/2010 | Droitcour et al. |
| 2010/0249630 | A1 | 9/2010 | Droitcour et al. |
| 2010/0249633 | A1 | 9/2010 | Droitcour et al. |
| 2010/0268121 | A1 | 10/2010 | Kilborn |
| 2010/0292568 | A1 | 11/2010 | Droitcour et al. |
| 2011/0060215 | A1 | 3/2011 | Tupin, Jr. et al. |
| 2011/0285579 | A1 | 11/2011 | Bangera et al. |
| 2012/0222214 | A1 * | 9/2012 | Lachenbruch ......... A61G 7/018 5/81.1 R |
| 2012/0245479 | A1 | 9/2012 | Ganesh et al. |
| 2013/0104312 | A1 | 5/2013 | O'Reagan |
| 2013/0123614 | A1 | 5/2013 | Bernstein et al. |
| 2013/0135137 | A1 | 5/2013 | Mulder et al. |
| 2014/0155729 | A1 | 6/2014 | Saitoh |
| 2015/0141794 | A1 | 5/2015 | Foo |
| 2015/0181840 | A1 | 7/2015 | Tupin, Jr. et al. |
| 2015/0208949 | A1 | 7/2015 | Tupin, Jr. et al. |
| 2015/0223733 | A1 | 8/2015 | Al-Alusi |
| 2015/0335310 | A1 | 11/2015 | Bernstein et al. |
| 2015/0351982 | A1 * | 12/2015 | Krenik .................. A47C 23/06 5/616 |
| 2015/0369911 | A1 | 12/2015 | Mabrouk et al. |
| 2016/0022145 | A1 | 1/2016 | Mostov |
| 2016/0022204 | A1 | 1/2016 | Mostov |
| 2016/0047909 | A1 | 2/2016 | Pu et al. |
| 2016/0213321 | A1 | 7/2016 | Bernstein et al. |
| 2016/0317370 | A1 | 11/2016 | Evans et al. |
| 2017/0181409 | A1 | 6/2017 | Tupin, Jr. et al. |
| 2017/0258366 | A1 | 9/2017 | Tupin, Jr. et al. |
| 2017/0347960 | A1 | 12/2017 | Falk et al. |
| 2018/0049669 | A1 * | 2/2018 | Vu ........................ A61B 5/0507 |
| 2018/0161225 | A1 | 6/2018 | Zerhusen et al. |
| 2018/0185222 | A1 | 7/2018 | Zerhusen et al. |
| 2018/0289305 | A1 | 10/2018 | Rahman et al. |
| 2018/0333103 | A1 | 11/2018 | Bardan et al. |
| 2018/0353086 | A1 | 12/2018 | Turner et al. |
| 2019/0015277 | A1 * | 1/2019 | Sauser .................... G01S 7/032 |
| 2019/0029900 | A1 * | 1/2019 | Walton .................. A61G 7/015 |
| 2019/0053707 | A1 * | 2/2019 | Lane ...................... G16H 40/67 |
| 2019/0104951 | A1 | 4/2019 | Valys et al. |
| 2019/0167500 | A1 | 6/2019 | Baker et al. |
| 2020/0046302 | A1 | 2/2020 | Jacquel et al. |
| 2020/0237252 | A1 * | 7/2020 | Lane ....................... G01S 13/88 |
| 2021/0251519 | A1 | 8/2021 | Fitzgibbons et al. |

FOREIGN PATENT DOCUMENTS

| | | |
|---|---|---|
| JP | 2008536121 A | 9/2008 |
| JP | 2010508128 A | 3/2010 |
| JP | 2013538598 A | 10/2013 |
| JP | 2014209957 A | 11/2014 |
| JP | 2015528349 A | 9/2015 |
| WO | 2018234394 A1 | 12/2018 |

OTHER PUBLICATIONS

Communication pursuant to Article 94(3) EPC for Application No. 21157153.4, Dated Apr. 12, 2024 (6 Pages).

Duraiswamy et al., "Build a UWB pulse generator on an FPGA," EDN Network, Jun. 23, 2011 (4 pages).

Spiral Antennas, "DAS and Public Safety Antennas—From Pulse Larsen-factory rep," http://www.antenna-theory.com/antennas/travelling/spiral.php; Jun. 12, 2017 (7 pages).

Tapered Baluns, Antenna Theory Home Antenna Definitions; http://www.antenna-theory.com/definitions/taperedbalun.php; Jun. 12, 2017 (2 pages).

The Infinite Balum; http://www.antenna-theory.com/definitions/infinite.php; Jun. 12, 2017 (3 pages).

Radar Basics—Minimal Measuring Range; http://www.radartutorial.eu/01.basics/Minimal%20Measuring%20Range.en.html; Jun. 12, 2017 (1 page).

Yilmaz et al, "Ultra-Wideband N-Bit Digitally Tunable Pulse Generator," published in 2005 IEEE International Conference on Ultra-Wideband; Date of Conference: Sep. 5-8, 2005; DOI: 10.1109/ICU.2005.1570027 (8 pages).

Amir et al., "Validation of remote dielectric sensing (ReDS™) technology for quantification of lung fluid status: Comparison to high resolution chest computed tomography in patients with and without acute heart failure," International Journal of Cardiology 221 (2016) 841-846 (6 pages).

Kaneko et al, "New scale to assess breathing movements of the chest and abdominal wall preliminary reliability testing," J. Phys. Ther. Sci. 27: 1987-1992, 2015 (6 pages).

Pramono et al., "Automatic Adventitious Respiratory Sound Analysis: A Systematic Review." PLoS One, May 26, 2027; 12(5):e0177926 (Year: 2017).

* cited by examiner

RADAR SENSORS FOR PATIENT MONITORING

The present application is a continuation of U.S. application Ser. No. 17/151,889, filed Jan. 19, 2021, now U.S. Pat. No. 11,877,844, which claims the benefit, under 35 U.S.C. § 119 (e), of U.S. Provisional Application No. 62/978,481, filed Feb. 19, 2020, and each of which is hereby incorporated by reference herein in its entirety.

BACKGROUND

Monitoring patient breathing and heart rate is desirable in clinical settings. Changes in breathing rate can indicate a change in a patient's condition, and certain factors such as an asymmetry of breathing may indicate a condition of the patient. Monitoring patient breathing may include manually counting breaths, measuring chest and abdominal wall mobility, determining any asymmetry in chest expansion, etc. Manual monitoring is time-intensive, prone to error, and cannot practically be done continuously for prolonged periods of time.

SUMMARY

An apparatus, system, or method may comprise one or more of the features recited in the appended claims and/or the following features which, alone or in any combination, may comprise patentable subject matter:

According to one aspect of the disclosure, a system for monitoring breathing, the system comprising one or more radar sensors configured to transmit a radar signal towards a patient; and receive a reflection of the radar signal from the patient, and circuitry comprising a radar controller to receive data from the one or more radar sensors indicative of the reflection of the radar signal from the patient; and a breathing pattern monitor to determine one or more parameters indicative of a breathing of the patient based on the data from the one or more radar sensors.

In some embodiments, to determine the one or more parameters indicative of the breathing of the patient based on the data from the one or more radar sensors comprises to determine that the patient has an asymmetrical breathing pattern.

In some embodiments, to determine the one or more parameters indicative of the breathing of the patient based on the data from the one or more radar sensors comprises to determine whether the patient is performing chest breathing.

In some embodiments, to determine the one or more parameters indicative of the breathing of the patient based on the data from the one or more radar sensors comprises to determine a chest expansion distance of the patient.

In some embodiments, to determine the one or more parameters indicative of the breathing of the patient based on the data from the one or more radar sensors comprises to determine a tidal volume of a patient's breathing.

In some embodiments, to determine the one or more parameters indicative of the breathing of the patient based on the data from the one or more radar sensors comprises to determine a rate of a patient's breathing.

In some embodiments, to determine the one or more parameters indicative of the breathing of the patient based on the data from the one or more radar sensors comprises to determine whether the patient has a Cheyne-Stokes breathing pattern.

In some embodiments, to determine the one or more parameters indicative of the breathing of the patient based on the data from the one or more radar sensors comprises to determine that the patient has a Kussmaul breathing pattern.

In some embodiments, to determine the one or more parameters indicative of the breathing of the patient based on the data from the one or more radar sensors comprises to determine that the patient has breathing apnea.

In some embodiments, the one or more radar sensors are connected to a patient bed, wherein the patient is in the patient bed.

In some embodiments, the one or more radar sensors are in a mobile radar unit.

In some embodiments, to transmit the radar signal comprises to transmit a radar signal between 30 and 300 gigahertz.

According to one aspect of the disclosure, a system for monitoring breathing, the system comprising one or more radar sensors configured to transmit a radar signal towards a patient; and receive, by the one or more radar sensors, a reflection of the radar signal from the patient, and circuitry comprising a radar controller to receive data from the one or more radar sensors indicative of the reflection of the radar signal from the patient; and an electronic stethoscope monitor to determine one or more breathing sounds of the patient based on the data from the one or more radar sensors.

In some embodiments, the system may further include a sound classifier to classify the breathing of the patient based on the one or more breathing sounds of the patient based on the data from the one or more radar sensors.

In some embodiments, to classify the breathing of the patient based on the one or more breathing sounds of the patient based on the data from the one or more radar sensors comprises to detect a wheezing sound based on the data from the one or more radar sensors; and classify the breathing of the patient as wheezing based on the wheezing sound.

In some embodiments, to classify the breathing of the patient based on the one or more breathing sounds of the patient based on the data from the one or more radar sensors comprises to detect a stridor sound based on the data from the one or more radar sensors; and classify the breathing of the patient as stridor based on the stridor sound.

In some embodiments, to classify the breathing of the patient based on the one or more breathing sounds of the patient based on the data from the one or more radar sensors comprises to detect a coarse crackles sound based on the data from the one or more radar sensors; and classify the breathing of the patient as coarse crackles based on the coarse crackles sound.

In some embodiments, to classify the breathing of the patient based on the one or more breathing sounds of the patient based on the data from the one or more radar sensors comprises to detect a fine crackles sound based on the data from the one or more radar sensors; and classify the breathing of the patient as fine crackles based on the fine crackles sound.

In some embodiments, to classify the breathing of the patient based on the one or more breathing sounds of the patient based on the data from the one or more radar sensors comprises to detect a pleural rub sound based on the data from the one or more radar sensors; and classify the breathing of the patient as pleural rub based on the pleural rub sound.

In some embodiments, to classify the breathing of the patient based on the one or more breathing sounds of the patient based on the data from the one or more radar sensors comprises to detect a normal breathing sound based on the data from the one or more radar sensors; and classify the breathing of the patient as normal based on the normal breathing sound.

In some embodiments, the one or more radar sensors are below a mattress in a patient bed.

In some embodiments, the one or more radar sensors are in a mobile radar unit.

According to one aspect of the disclosure, a system for monitoring movement of a patient, the system comprising one or more radar sensors configured to transmit a radar signal towards a patient on a patient bed; and receive a reflection of the radar signal from the patient, and circuitry comprising a patient position monitor to receive data from the one or more radar sensors indicative of the reflection of the radar signal from the patient; and determine a position parameter of the patient, wherein the position parameter is indicative of a location or orientation of the patient on the patient bed.

In some embodiments, the circuitry further comprises a rotation bladder controller to determine whether the patient should be rotated based on the position parameter of the patient.

In some embodiments, to determine whether the patient should be rotated comprises to determine that the patient has not been rotated for at least a threshold amount of time.

In some embodiments, the circuitry further comprises a rotation bladder controller to determine, based on the position parameter, a subset of a plurality of rotation bladders of the patient bed to inflate in order to rotate the patient; and send a signal to inflate the subset of the plurality of rotation bladders.

In some embodiments, the circuitry further comprises a rotation bladder controller to determine, based on the position parameter, a subset of a plurality of rotation bladders of the patient bed to inflate in order to move the patient towards a center of the patient bed; and send a signal to inflate the subset of the plurality of rotation bladders.

In some embodiments, the circuitry further comprises a percussion and vibration (P & V) bladder controller to determine, based on the position parameter, a subset of a plurality of P & V bladders of the patient bed to inflate in order to perform P & V therapy on the patient, wherein the selected subset of the plurality of P & V bladders are P & V bladders under a current position of the patient; and send a signal to inflate the subset of the plurality of P & V bladders.

In some embodiments, the one or more radar sensors are further configured to transmit an additional radar signal towards the patient during the P & V therapy; and receive a reflection of the additional radar signal from the patient, wherein the P & V bladder controller is further to receive additional data from the one or more radar sensors indicative of the reflection of the additional radar signal from the patient; determine, based on the additional data from the one or more radar sensors, an amplitude of vibration of the patient caused by the P & V therapy; and adjust a signal sent to inflate the subset of the plurality of P & V bladders based on the amplitude of vibration of the patient.

In some embodiments, the P & V bladder controller is further to determine, based on the position parameter, a subset of a plurality of rotation bladders of the patient bed to inflate in order to move the patient towards a center of the patient bed; and send a signal to inflate the subset of the plurality of rotation bladders to move the patient towards the center of the patient bed prior to sending the signal to inflate the subset of the plurality of P & V bladders.

According to one aspect of the disclosure, a system for facilitating breathing exercises, the system comprising circuitry comprising a video instructor circuitry to present a breathing instruction to a patient; one or more radar sensors configured to transmit a radar signal towards the patient after presentation of the breathing instruction; and receive a reflection of the radar signal from the patient, wherein the circuitry further comprises a breathing exercises monitor to receive data from the one or more radar sensors indicative of the reflection of the radar signal from the patient; and determine, based on the data from the one or more radar sensors, a parameter of one or more breaths of the patient, wherein the video instructor circuitry is further to present a second breathing instruction to the patient, wherein the second breathing instruction is based on the parameter of the one or more breaths of the patient.

In some embodiments, to present the breathing instruction to the patient comprises to present the breathing instruction on a display, wherein the patient is in a patient bed, and wherein the display is attached to the patient bed.

In some embodiments, to present the breathing instruction to the patient comprises to present the breathing instruction on a display, and wherein the display is attached to a mobile breathing exercise device.

In some embodiments, the breathing exercises monitor is further to store performance data of the patient during an exercise session associated with the breathing instruction and the second breathing instruction, wherein the performance data indicates a response of the patient to the breathing instruction and to the second breathing instruction.

In some embodiments, the breathing exercises monitor is further to determine, based on the performance data, a third breathing instruction of a second exercise session different from the first.

According to one aspect of the disclosure, a system for monitoring patients, the system comprising one or more radar sensors configured to transmit a radar signal towards a patient in a waiting room of a hospital; and receive a reflection of the radar signal from the patient; and a vital signs analysis server configured to receive data from the one or more radar sensors indicative of the reflection of the radar signal from the patient; and determine one or more vital sign parameters of the patient based on the data from the one or more radar sensors.

In some embodiments, the one or more radar sensors are attached to one or more chairs in the waiting room.

In some embodiments, the one or more radar sensors are attached to a rotatable mount.

In some embodiments, the one or more vital sign parameters comprise a parameter indicative of a breathing of the patient.

In some embodiments, the one or more vital sign parameters comprise a parameter indicative of a heartbeat of the patient.

In some embodiments, the vital signs analysis server is further configured to determine whether an alert should be provided to a caregiver based on the one or more vital sign parameters; and provide an alert to a caregiver in response to a determination that an alert should be provided to a caregiver based on the one or more vital sign parameters.

According to one aspect of the disclosure, a breathing therapy system comprising one or more radar sensors configured to transmit a radar signal towards a patient; receive a reflection of the radar signal from the patient; circuitry comprising a breathing monitor to receive data from the one or more radar sensors indicative of the reflection of the radar signal from the patient; and determine one or more parameters indicative of a breathing of the patient based on the data from the one or more radar sensors; and an airflow controller to control, based on the one or more parameters indicative of the breathing of the patient, an airflow provided to the patient by the breathing therapy system.

In some embodiments, to determine the one or more parameters indicative of the breathing of the patient based on the data from the one or more radar sensors comprises to determine a current phase of a breathing cycle of the patient based on the data from the one or more radar sensors, and wherein to control the airflow provided to the patient comprises to control the airflow provided to the patient based on a determined current phase of the breathing cycle of the patient.

In some embodiments, to determine the current phase of the breathing cycle of the patient based on the data from the one or more radar sensors comprises to determine that the patient is breathing in, and wherein to control the airflow provided to the patient based on a determined current phase of the breathing cycle of the patient comprises to provide a positive pressure airflow to the patient based on a determination that the patient is breathing in.

In some embodiments, to determine the one or more parameters indicative of the breathing of the patient based on the data from the one or more radar sensors comprises to determine that the patient is beginning a cough, and wherein to control the airflow provided to the patient comprises to provide a negative airflow to the patient to assist with the cough based on a determination that the patient is beginning the cough.

According to one aspect of the disclosure, an infant breathing monitor comprising one or more radar sensors configured to transmit a radar signal a radar signal towards an infant; and receive a reflection of the radar signal from the infant, and circuitry configured to receive data from the one or more radar sensors indicative of the reflection of the radar signal from the infant; determine, based on the data from the one or more radar sensors, whether the infant is breathing; and trigger an alert based on the airflow provided to the patient by the breathing therapy system.

In some embodiments, the infant breathing monitor is attached to a crib, wherein the infant is in the crib.

According to one aspect of the disclosure, a method for monitoring breathing, the method comprising transmitting, by one or more radar sensors, a radar signal towards a patient; receiving, by the one or more radar sensors, a reflection of the radar signal from the patient; receiving, by circuitry, data from the one or more radar sensors indicative of the reflection of the radar signal from the patient; and determining, by the circuitry, one or more parameters indicative of a breathing of the patient based on the data from the one or more radar sensors.

In some embodiments, determining the one or more parameters indicative of the breathing of the patient based on the data from the one or more radar sensors comprises determining that the patient has an asymmetrical breathing pattern.

In some embodiments, determining the one or more parameters indicative of the breathing of the patient based on the data from the one or more radar sensors comprises determining whether the patient is performing chest breathing.

In some embodiments, determining the one or more parameters indicative of the breathing of the patient based on the data from the one or more radar sensors comprises determining a chest expansion distance of the patient.

In some embodiments, determining the one or more parameters indicative of the breathing of the patient based on the data from the one or more radar sensors comprises determining a tidal volume of a patient's breathing.

In some embodiments, determining the one or more parameters indicative of the breathing of the patient based on the data from the one or more radar sensors comprises determining a rate of a patient's breathing.

In some embodiments, determining the one or more parameters indicative of the breathing of the patient based on the data from the one or more radar sensors comprises determining whether the patient has a Cheyne-Stokes breathing pattern.

In some embodiments, determining the one or more parameters indicative of the breathing of the patient based on the data from the one or more radar sensors comprises determining that the patient has a Kussmaul breathing pattern.

In some embodiments, determining the one or more parameters indicative of the breathing of the patient based on the data from the one or more radar sensors comprises determining that the patient has breathing apnea.

In some embodiments, the one or more radar sensors are connected to a patient bed, wherein the patient is in the patient bed.

In some embodiments, the one or more radar sensors are in a mobile radar unit.

In some embodiments, transmitting the radar signal comprises transmitting a radar signal between 30 and 300 gigahertz.

According to one aspect of the disclosure, a method for monitoring breathing, the method comprising transmitting, by one or more radar sensors, a radar signal towards a patient; receiving, by the one or more radar sensors, a reflection of the radar signal from the patient; receiving, by circuitry, data from the one or more radar sensors indicative of the reflection of the radar signal from the patient; determining, by the circuitry, one or more breathing sounds of the patient based on the data from the one or more radar sensors.

In some embodiments, the method may further include classifying, by the circuitry, the breathing of the patient based on the one or more breathing sounds of the patient based on the data from the one or more radar sensors.

In some embodiments, classifying, by the circuitry, the breathing of the patient based on the one or more breathing sounds of the patient based on the data from the one or more radar sensors comprises detecting, by the circuitry, a wheezing sound based on the data from the one or more radar sensors; and classifying the breathing of the patient as wheezing based on the wheezing sound.

In some embodiments, classifying, by the circuitry, the breathing of the patient based on the one or more breathing sounds of the patient based on the data from the one or more radar sensors comprises detecting, by the circuitry, a stridor sound based on the data from the one or more radar sensors; and classifying the breathing of the patient as stridor based on the stridor sound.

In some embodiments, classifying, by the circuitry, the breathing of the patient based on the one or more breathing sounds of the patient based on the data from the one or more radar sensors comprises detecting, by the circuitry, a coarse crackles sound based on the data from the one or more radar sensors; and classifying the breathing of the patient as coarse crackles based on the coarse crackles sound.

In some embodiments, classifying, by the circuitry, the breathing of the patient based on the one or more breathing sounds of the patient based on the data from the one or more radar sensors comprises detecting, by the circuitry, a fine crackles sound based on the data from the one or more radar sensors; and classifying the breathing of the patient as fine crackles based on the fine crackles sound.

In some embodiments, classifying, by the circuitry, the breathing of the patient based on the one or more breathing sounds of the patient based on the data from the one or more radar sensors comprises detecting, by the circuitry, a pleural rub sound based on the data from the one or more radar sensors; and classifying the breathing of the patient as pleural rub based on the pleural rub sound.

In some embodiments, classifying, by the circuitry, the breathing of the patient based on the one or more breathing sounds of the patient based on the data from the one or more radar sensors comprises detecting, by the circuitry, a normal breathing sound based on the data from the one or more radar sensors; and classifying the breathing of the patient as normal based on the normal breathing sound.

In some embodiments, the one or more radar sensors are below a mattress in a patient bed.

In some embodiments, the one or more radar sensors are in a mobile radar unit.

According to one aspect of the disclosure, a method for monitoring movement of a patient, the method comprising transmitting, by one or more radar sensors, a radar signal towards a patient on a patient bed; receiving, by the one or more radar sensors, a reflection of the radar signal from the patient; receiving, by circuitry, data from the one or more radar sensors indicative of the reflection of the radar signal from the patient; determining, by the circuitry, a position parameter of the patient, wherein the position parameter is indicative of a location or orientation of the patient on the patient bed.

In some embodiments, the method may further include determining, by the circuitry, whether the patient should be rotated based on the position parameter of the patient.

In some embodiments, the method may further include determining whether the patient should be rotated comprises determining that the patient has not been rotated for at least a threshold amount of time.

In some embodiments, the method may further include determining, by the circuitry and based on the position parameter, a subset of a plurality of rotation bladders of the patient bed to inflate in order to rotate the patient; and sending, by the circuitry, a signal to inflate the subset of the plurality of rotation bladders.

In some embodiments, the method may further include determining, by the circuitry and based on the position parameter, a subset of a plurality of rotation bladders of the patient bed to inflate in order to move the patient towards a center of the patient bed; and sending, by the circuitry, a signal to inflate the subset of the plurality of rotation bladders.

In some embodiments, the method may further include determining, by the circuitry and based on the position parameter, a subset of a plurality of percussion and vibration (P & V) bladders of the patient bed to inflate in order to perform P & V therapy on the patient, wherein the selected subset of the plurality of P & V bladders are P & V bladders under a current position of the patient; and sending, by the circuitry, a signal to inflate the subset of the plurality of P & V bladders.

In some embodiments, the method may further include transmitting, by the one or more radar sensors, an additional radar signal towards the patient during the P & V therapy; receiving, by the one or more radar sensors, a reflection of the additional radar signal from the patient; receiving, by the circuitry, additional data from the one or more radar sensors indicative of the reflection of the additional radar signal from the patient; determining, by the circuitry and based on the additional data from the one or more radar sensors, an amplitude of vibration of the patient caused by the P & V therapy; and adjusting, by the circuitry, a signal sent to inflate the subset of the plurality of P & V bladders based on the amplitude of vibration of the patient.

In some embodiments, the method may further include determining, by the circuitry and based on the position parameter, a subset of a plurality of rotation bladders of the patient bed to inflate in order to move the patient towards a center of the patient bed; and sending, by the circuitry, a signal to inflate the subset of the plurality of rotation bladders to move the patient towards the center of the patient bed prior to sending the signal to inflate the subset of the plurality of P & V bladders.

According to one aspect of the disclosure, a method for facilitating breathing exercises, the method comprising presenting, by circuitry, a breathing instruction to a patient; transmitting, by one or more radar sensors, a radar signal towards the patient after presentation of the breathing instruction; receiving, by the one or more radar sensors, a reflection of the radar signal from the patient; receiving, by the circuitry, data from the one or more radar sensors indicative of the reflection of the radar signal from the patient; determining, by the circuitry and based on the data from the one or more radar sensors, a parameter of one or more breaths of the patient; and presenting, by the circuitry, a second breathing instruction to the patient, wherein the second breathing instruction is based on the parameter of the one or more breaths of the patient.

In some embodiments, presenting the breathing instruction to the patient comprises presenting the breathing instruction on a display, wherein the patient is in a patient bed, and wherein the display is attached to the patient bed.

In some embodiments, presenting the breathing instruction to the patient comprises presenting the breathing instruction on a display, and wherein the display is attached to a mobile breathing exercise device.

In some embodiments, the method may further include storing, by the circuitry, performance data of the patient during an exercise session associated with the breathing instruction and the second breathing instruction, wherein the performance data indicates a response of the patient to the breathing instruction and to the second breathing instruction.

In some embodiments, the method may further include determining, by the circuitry and based on the performance data, a third breathing instruction of a second exercise session different from the first.

According to one aspect of the disclosure, a method for monitoring patients, the method comprising transmitting, by one or more radar sensors, a radar signal towards a patient in a waiting room of a hospital; receiving, by the one or more radar sensors, a reflection of the radar signal from the patient; receiving, by circuitry, data from the one or more radar sensors indicative of the reflection of the radar signal from the patient; and determining, by the circuitry, one or more vital sign parameters of the patient based on the data from the one or more radar sensors.

In some embodiments, the one or more radar sensors are attached to one or more chairs in the waiting room.

In some embodiments, the one or more radar sensors are attached to a rotatable mount.

In some embodiments, the one or more vital sign parameters comprise a parameter indicative of a breathing of the patient.

In some embodiments, the one or more vital sign parameters comprise a parameter indicative of a heartbeat of the patient.

In some embodiments, the method may further include determining, by the circuitry, whether an alert should be provided to a caregiver based on the one or more vital sign parameters; and providing, by the circuitry, an alert to a caregiver in response to a determination that an alert should be provided to a caregiver based on the one or more vital sign parameters.

According to one aspect of the disclosure, a method for operating a breathing therapy system, the method comprising transmitting, by one or more radar sensors of the breathing therapy system, a radar signal towards a patient; receiving, by the one or more radar sensors, a reflection of the radar signal from the patient; receiving, by circuitry of the breathing therapy system, data from the one or more radar sensors indicative of the reflection of the radar signal from the patient; determining, by the circuitry, one or more parameters indicative of a breathing of the patient based on the data from the one or more radar sensors; and controlling, by the circuitry and based on the one or more parameters indicative of the breathing of the patient, an airflow provided to the patient by the breathing therapy system.

In some embodiments, determining the one or more parameters indicative of the breathing of the patient based on the data from the one or more radar sensors comprises determining a current phase of a breathing cycle of the patient based on the data from the one or more radar sensors, and wherein controlling the airflow provided to the patient comprises controlling the airflow provided to the patient based on a determined current phase of the breathing cycle of the patient.

In some embodiments, determining the current phase of the breathing cycle of the patient based on the data from the one or more radar sensors comprises determining that the patient is breathing in, and wherein controlling the airflow provided to the patient based on a determined current phase of the breathing cycle of the patient comprises providing a positive pressure airflow to the patient based on a determination that the patient is breathing in.

In some embodiments, determining the one or more parameters indicative of the breathing of the patient based on the data from the one or more radar sensors comprises determining that the patient is beginning a cough, and wherein controlling the airflow provided to the patient comprises providing a negative airflow to the patient to assist with the cough based on a determination that the patient is beginning the cough.

According to one aspect of the disclosure, a method for monitoring an infant, the method comprising transmitting, by one or more radar sensors of the breathing therapy system, a radar signal towards the infant; receiving, by the one or more radar sensors, a reflection of the radar signal from the infant; receiving, by circuitry of an infant breathing monitor, data from the one or more radar sensors indicative of the reflection of the radar signal from the infant; determining, by the circuitry and based on the data from the one or more radar sensors, whether the infant is breathing; and triggering, by the circuitry, an alert based on the airflow provided to the patient by the breathing therapy system.

In some embodiments, the infant breathing monitor is attached to a crib, wherein the infant is in the crib.

According to one aspect of the disclosure, one or more non-transitory computer-readable media comprising a plurality of instructions stored thereon that, when executed by a processor of a system for monitoring breathing, causes the system to transmit, by one or more radar sensors of the system, a radar signal towards a patient; receive, by the one or more radar sensors, a reflection of the radar signal from the patient; receive data from the one or more radar sensors indicative of the reflection of the radar signal from the patient; and determine one or more parameters indicative of a breathing of the patient based on the data from the one or more radar sensors.

In some embodiments, to determine the one or more parameters indicative of the breathing of the patient based on the data from the one or more radar sensors comprises to determine that the patient has an asymmetrical breathing pattern.

In some embodiments, to determine the one or more parameters indicative of the breathing of the patient based on the data from the one or more radar sensors comprises to determine whether the patient is performing chest breathing.

In some embodiments, to determine the one or more parameters indicative of the breathing of the patient based on the data from the one or more radar sensors comprises to determine a chest expansion distance of the patient.

In some embodiments, to determine the one or more parameters indicative of the breathing of the patient based on the data from the one or more radar sensors comprises to determine a tidal volume of a patient's breathing.

In some embodiments, to determine the one or more parameters indicative of the breathing of the patient based on the data from the one or more radar sensors comprises to determine a rate of a patient's breathing.

In some embodiments, to determine the one or more parameters indicative of the breathing of the patient based on the data from the one or more radar sensors comprises to determine whether the patient has a Cheyne-Stokes breathing pattern.

In some embodiments, to determine the one or more parameters indicative of the breathing of the patient based on the data from the one or more radar sensors comprises to determine that the patient has a Kussmaul breathing pattern.

In some embodiments, to determine the one or more parameters indicative of the breathing of the patient based on the data from the one or more radar sensors comprises to determine that the patient has breathing apnea.

In some embodiments, the one or more radar sensors are connected to a patient bed, wherein the patient is in the patient bed.

In some embodiments, the one or more radar sensors are in a mobile radar unit.

In some embodiments, to transmit the radar signal comprises to transmit a radar signal between 30 and 300 gigahertz.

According to one aspect of the disclosure, one or more non-transitory computer-readable media comprising a plurality of instructions stored thereon that, when executed by a processor of a system for monitoring breathing, causes the system to transmit, by one or more radar sensors of the system, a radar signal towards a patient; receive, by the one or more radar sensors, a reflection of the radar signal from the patient; receive data from the one or more radar sensors indicative of the reflection of the radar signal from the patient; and determine one or more breathing sounds of the patient based on the data from the one or more radar sensors.

In some embodiments, the plurality of instructions further cause the system to classify the breathing of the patient based on the one or more breathing sounds of the patient based on the data from the one or more radar sensors.

In some embodiments, to classify the breathing of the patient based on the one or more breathing sounds of the patient based on the data from the one or more radar sensors comprises to detect a wheezing sound based on the data from the one or more radar sensors; and classify the breathing of the patient as wheezing based on the wheezing sound.

In some embodiments, to classify the breathing of the patient based on the one or more breathing sounds of the patient based on the data from the one or more radar sensors comprises to detect a stridor sound based on the data from the one or more radar sensors; and classify the breathing of the patient as stridor based on the stridor sound.

In some embodiments, to classify the breathing of the patient based on the one or more breathing sounds of the patient based on the data from the one or more radar sensors comprises to detect a coarse crackles sound based on the data from the one or more radar sensors; and classify the breathing of the patient as coarse crackles based on the coarse crackles sound.

In some embodiments, to classify the breathing of the patient based on the one or more breathing sounds of the patient based on the data from the one or more radar sensors comprises to detect a fine crackles sound based on the data from the one or more radar sensors; and classify the breathing of the patient as fine crackles based on the fine crackles sound.

In some embodiments, to classify the breathing of the patient based on the one or more breathing sounds of the patient based on the data from the one or more radar sensors comprises to detect a pleural rub sound based on the data from the one or more radar sensors; and classify the breathing of the patient as pleural rub based on the pleural rub sound.

In some embodiments, to classify the breathing of the patient based on the one or more breathing sounds of the patient based on the data from the one or more radar sensors comprises to detect a normal breathing sound based on the data from the one or more radar sensors; and classify the breathing of the patient as normal based on the normal breathing sound.

In some embodiments, the one or more radar sensors are below a mattress in a patient bed.

In some embodiments, the one or more radar sensors are in a mobile radar unit.

According to one aspect of the disclosure, one or more non-transitory computer-readable media comprising a plurality of instructions stored thereon that, when executed by a processor of a system for monitoring movement of a patient, causes the system to transmit, by one or more radar sensors of the system, a radar signal towards a patient on a patient bed; receive, by the one or more radar sensors, a reflection of the radar signal from the patient; receive data from the one or more radar sensors indicative of the reflection of the radar signal from the patient; and determine a position parameter of the patient, wherein the position parameter is indicative of a location or orientation of the patient on the patient bed.

In some embodiments, the plurality of instructions further cause the system to determine whether the patient should be rotated based on the position parameter of the patient.

In some embodiments, to determine whether the patient should be rotated comprises to determine that the patient has not been rotated for at least a threshold amount of time.

In some embodiments, the plurality of instructions further cause the system to determine, based on the position parameter, a subset of a plurality of rotation bladders of the patient bed to inflate in order to rotate the patient; and send a signal to inflate the subset of the plurality of rotation bladders.

In some embodiments, the plurality of instructions further cause the system to determine, based on the position parameter, a subset of a plurality of rotation bladders of the patient bed to inflate in order to move the patient towards a center of the patient bed; and send a signal to inflate the subset of the plurality of rotation bladders.

In some embodiments, the plurality of instructions further cause the system to determine, based on the position parameter, a subset of a plurality of percussion and vibration (P & V) bladders of the patient bed to inflate in order to perform P & V therapy on the patient, wherein the selected subset of the plurality of P & V bladders are P & V bladders under a current position of the patient; and send a signal to inflate the subset of the plurality of P & V bladders.

In some embodiments, the plurality of instructions further cause the system to transmit, by the one or more radar sensors, an additional radar signal towards the patient during the P & V therapy; receive, by the one or more radar sensors, a reflection of the additional radar signal from the patient; receive additional data from the one or more radar sensors indicative of the reflection of the additional radar signal from the patient; determine, based on the additional data from the one or more radar sensors, an amplitude of vibration of the patient caused by the P & V therapy; and adjust a signal sent to inflate the subset of the plurality of P & V bladders based on the amplitude of vibration of the patient.

In some embodiments, the plurality of instructions further cause the system to determine, based on the position parameter, a subset of a plurality of rotation bladders of the patient bed to inflate in order to move the patient towards a center of the patient bed; and send a signal to inflate the subset of the plurality of rotation bladders to move the patient towards the center of the patient bed prior to sending the signal to inflate the subset of the plurality of P & V bladders.

According to one aspect of the disclosure, one or more non-transitory computer-readable media comprising a plurality of instructions stored thereon that, when executed by a processor of a system for facilitating breathing exercises, causes the system to present a breathing instruction to a patient; transmit, by one or more radar sensors of the system, a radar signal towards the patient after presentation of the breathing instruction; receive, by one or more radar sensors of the system, a reflection of the radar signal from the patient; receive data from the one or more radar sensors indicative of the reflection of the radar signal from the patient; determine, based on the data from the one or more radar sensors, a parameter of one or more breaths of the patient; and present a second breathing instruction to the patient, wherein the second breathing instruction is based on the parameter of the one or more breaths of the patient.

In some embodiments, to present the breathing instruction to the patient comprises to present the breathing instruction on a display, wherein the patient is in a patient bed, and wherein the display is attached to the patient bed.

In some embodiments, to present the breathing instruction to the patient comprises to present the breathing instruction on a display, and wherein the display is attached to a mobile breathing exercise device.

In some embodiments, the plurality of instructions further cause the system to store performance data of the patient during an exercise session associated with the breathing instruction and the second breathing instruction, wherein the performance data indicates a response of the patient to the breathing instruction and to the second breathing instruction.

In some embodiments, the plurality of instructions further cause the system to determine, based on the performance data, a third breathing instruction of a second exercise session different from the first.

According to one aspect of the disclosure, one or more non-transitory computer-readable media comprising a plurality of instructions stored thereon that, when executed by a processor of a system for monitoring patients, causes the system to transmit, by one or more radar sensors of the system, a radar signal towards a patient in a waiting room of a hospital; receive, by the one or more radar sensors, a reflection of the radar signal from the patient; receive data from the one or more radar sensors indicative of the reflection of the radar signal from the patient; and determine one or more vital sign parameters of the patient based on the data from the one or more radar sensors.

In some embodiments, the one or more radar sensors are attached to one or more chairs in the waiting room.

In some embodiments, the one or more radar sensors are attached to a rotatable mount.

In some embodiments, the one or more vital sign parameters comprise a parameter indicative of a breathing of the patient.

In some embodiments, the one or more vital sign parameters comprise a parameter indicative of a heartbeat of the patient.

In some embodiments, plurality of instructions further causes the system to determine whether an alert should be provided to a caregiver based on the one or more vital sign parameters; and provide an alert to a caregiver in response to a determination that an alert should be provided to a caregiver based on the one or more vital sign parameters.

According to one aspect of the disclosure, one or more non-transitory computer-readable media comprising a plurality of instructions stored thereon that, when executed by a processor of a breathing therapy system, causes the breathing therapy system to transmit, by one or more radar sensors of the breathing therapy system, a radar signal towards a patient; receive, by the one or more radar sensors, a reflection of the radar signal from the patient; receive data from the one or more radar sensors indicative of the reflection of the radar signal from the patient; determine one or more parameters indicative of a breathing of the patient based on the data from the one or more radar sensors; and control, based on the one or more parameters indicative of the breathing of the patient, an airflow provided to the patient by the breathing therapy system.

In some embodiments, to determine the one or more parameters indicative of the breathing of the patient based on the data from the one or more radar sensors comprises to determine a current phase of a breathing cycle of the patient based on the data from the one or more radar sensors, and wherein to control the airflow provided to the patient comprises to control the airflow provided to the patient based on a determined current phase of the breathing cycle of the patient.

In some embodiments, to determine the current phase of the breathing cycle of the patient based on the data from the one or more radar sensors comprises to determine that the patient is breathing in, and wherein to control the airflow provided to the patient based on a determined current phase of the breathing cycle of the patient comprises to provide a positive pressure airflow to the patient based on a determination that the patient is breathing in.

In some embodiments, to determine the one or more parameters indicative of the breathing of the patient based on the data from the one or more radar sensors comprises to determine that the patient is beginning a cough, and wherein to control the airflow provided to the patient comprises to provide a negative airflow to the patient to assist with the cough based on a determination that the patient is beginning the cough.

According to one aspect of the disclosure, one or more non-transitory computer-readable media comprising a plurality of instructions stored thereon that, when executed by a processor of an infant breathing monitor, causes the infant breathing monitor to transmit, by one or more radar sensors of the infant breathing monitor, a radar signal a radar signal towards an infant; receive, by the one or more radar sensors, a reflection of the radar signal from the infant; receive data from the one or more radar sensors indicative of the reflection of the radar signal from the infant; determine, based on the data from the one or more radar sensors, whether the infant is breathing; and trigger an alert based on the airflow provided to the patient by the breathing therapy system.

In some embodiments, the infant breathing monitor is attached to a crib, wherein the infant is in the crib.

BRIEF DESCRIPTION OF THE DRAWINGS

The detailed description particularly refers to the accompanying figures, in which.

DETAILED DESCRIPTION

Figure 1:
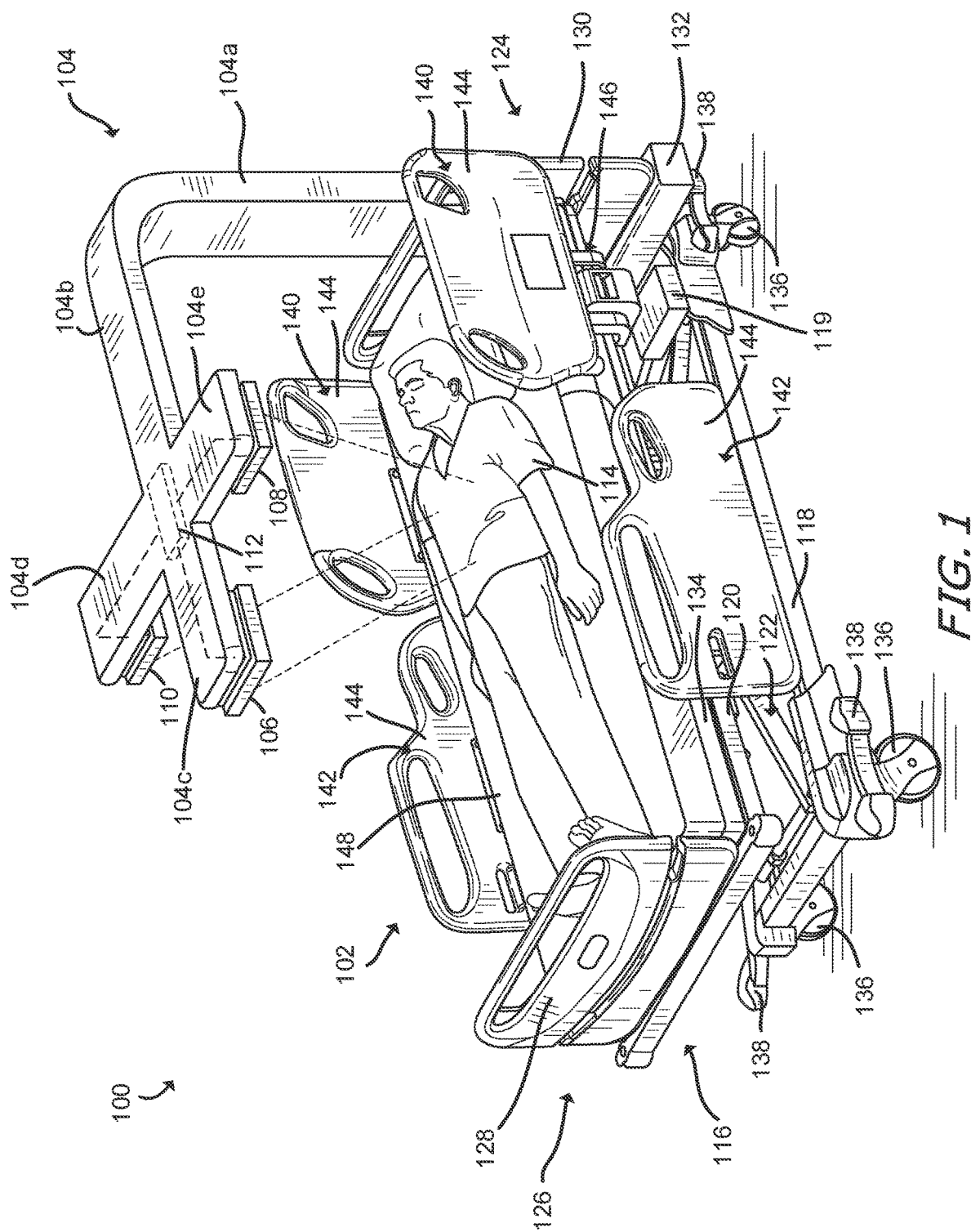
FIG. 1 is a perspective view of a system for monitoring a patient using one or more radio detection and ranging (radar) sensors.

According to some embodiments of the present disclosure, one or more radio detection and ranging (radar) apparatuses are integrated into systems such as patient support systems and breathing monitor systems. The radar apparatuses are used to monitor patients, such as by monitoring heart rate, breathing, and positioning.

While all types of systems implementing the disclosed technology are contemplated herein, some examples of a patient support system include a standalone mattress system, a mattress overlay, a patient bed, a patient bed with an integrated mattress system, a surgical table, an examination table, an imaging table, a stretcher, a chair, a wheelchair, and a patient lift, just to name a few. Patient support surfaces contemplated herein include air mattress, foam mattresses, combination air and foam mattresses, mattress overlays, surgical table pads and mattresses, stretcher pads and mattresses, chair pads, wheelchair pads, and patient lift pads, just to name a few.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features Referring now to FIG. 1, a patient support system 100 includes a patient bed 102, a radar support mount 104, an abdominal radar sensor 106, a left radar sensor 108, a right radar sensor 110, and bed circuitry 112. The radar sensors 106, 108, 110 monitor a patient 114 on the patient bed 102. As discussed in more detail below, the radar sensors 106, 108, 110 may monitor a patient's heartrate, breathing patterns, position on the bed, etc.

Each radar sensor 106, 108, 110 may be any suitable radar sensor. In the illustrative embodiment, each radar sensor 106, 108, 110 is a millimeter-wave sensor that operates at 30-300 gigahertz (GHz). Each radar sensor 106, 108, 110 may operate over a range of frequencies, such as 60-64 GHz or 76-81 GHz. Each radar sensor 106, 108, 110 has one or more transmitter and one or more receiver. For example, each of the radar sensors 106, 108, 110 may include one or more of an AWR1843, AWR1642, AWR1443, AWR1243, IWR6843AoP, IWR6843, IWR1843, IWR1642, and/or IWR1443 chip by Texas Instruments. In some embodiments, the radar sensors 106, 108, 110 may include two or more radar chips that are cascaded together such that they operate synchronously, giving improved target detection and resolution. Additionally or alternatively, the radar sensors 106, 108, 110 may be cascaded together.

In use, each radar sensor 106, 108, 110 emits radio waves, such as millimeter waves. The radar sensors 106, 108, 110 may emit a single frequency, a series of pulses, a shaped pulse, a chirped pulse, or any other suitable wave. The waves propagate from the radar sensors 106, 108, 110 and are reflected from the patient 114 back to the radar sensors 106, 108, 110. As used herein, a reflected radar signal or reflection of a radar signal refers to a radar signal that is scattered, coherently reflected, incoherently reflected, partially reflected, etc. The reflected signals can be processed to determine a distance from the radar sensors 106, 108, 110 to one or more areas of the patient 114, such as by determining a time-of-flight or phase of the reflected signals. Multiple areas of the patient 114 can be detected as multiple reflected signals. The location of the areas reflecting the waves can be determined by the difference in reflected signals in different receivers. Additionally or alternatively, the velocity of certain areas of the patient 114 that are reflecting waves may be determined based on a Doppler shift of the reflected waves. In this way, the radar sensors 106, 108, 110 can be used to map the position and contour of the patient 114. In the illustrative embodiment, the abdominal radar sensor 106 maps the contour of the area of the patient 114 located in the center of the patient bed 102, and the left radar sensor 110 and right radar sensor 110 maps the area of the patient 114 located in the right and left parts of the patient bed 102, respectively. Additionally or alternatively, any of the radar sensors 106, 108, 110 may be used to map any area of the patient 114 in any part of the patient bed 102.

In some embodiments, multiple transmitting antennae from some or all of the radar sensors 106, 108, 110 may be operating with a controlled phase difference, allowing for beamforming. Beamforming may be used to probe a particular area of a patient 114, patient bed 102, or room.

It should be appreciated that, in some embodiments, the radio waves may penetrate some materials such as clothes, blankets, sheets, allowing for a patient 114 to be monitored under a blanket without contact.

In the illustrative embodiment, the radar support mount 104 extends over a patient bed 102. The radar support mount 104 may be attached to the patient bed 102 or may form part of a free-standing radar monitoring unit. It should be appreciated that, in some embodiments, the radar sensors 106, 108, 110 may be positioned differently from the configuration shown in FIG. 1. For example, some or all of the radar sensors 106, 108, 110 may be positioned to the side of the patient 114, on a wall of a room, embedded in the patient bed 102, and/or in any other suitable location relative to the patient 114.

The radar sensors 106, 108, 110 may be connected to the bed circuitry 112 in any suitable manner. In the illustrative embodiment, one or more wires connect the radar sensors 106, 108, 110 to the bed circuitry 112. Additionally or alternatively, the radar sensors 106, 108, 110 may be connected to the bed circuitry 112 using fiber optics or a wireless signal. In some embodiments, the bed circuitry 112 may be located next to one or more of the radar sensors 106, 108, 110 and/or may be integrated into the radar sensors 106, 108, 110. In some embodiments, some or all of the bed circuitry 112 may be located in the radar support mount 104, as shown in FIG. 1. Additionally or alternatively, some or all of the bed circuitry 112 may be located in any suitable location, such as in the base of the patient bed 102, in a separate component near the patient bed 102, in a remote location, etc.

The bed circuitry 112 may be embodied as any circuitry capable of performing the functions described herein. For example, the bed circuitry 112 may be embodied as or otherwise be included in, without limitation, an embedded computing system, a System-on-a-Chip (SoC), a multiprocessor system, a processor-based system, a consumer electronic device, a smartphone, a cellular phone, a desktop computer, a server computer, a tablet computer, a notebook computer, a laptop computer, a network device, a router, a switch, a networked computer, a wearable computer, a handset, a messaging device, a camera device, and/or any other computing device. The bed circuitry 112 may include one or more processors, memory, one or more data storage devices, communication circuitry, and/or any other suitable component. In some embodiments, one or more of the components of the bed circuitry 112 may be incorporated in, or otherwise form a portion of, another component. For example, memory, or portions thereof, may be incorporated in the processor in some embodiments.

Still referring to FIG. 1, bed 102 includes a frame 116 that, in turn, includes a lower frame or base 118, an upper frame assembly 120, and a lift system 122 coupling upper frame assembly 120 to base 118. Lift system 122 is operable to raise, lower, and tilt upper frame assembly 120 relative to base 118. Bed 102 has a head end 124 and a foot end 126. Bed 10 further includes a footboard 128 at the foot end 126 and a headboard 130 at the head end 124. Headboard 130 is coupled to a raised portion 132 of base 28. Footboard 128 is coupled to foot end 126 of upper frame assembly 120 in the illustrative example. In other embodiments, footboard 128 is coupled to an extendable and retractable portion of a foot section of a mattress support deck 134 of upper frame assembly 120. Base 118 includes wheels or casters 136 that roll along a floor as bed 102 is moved from one location to another. A set of foot pedals 138 are coupled to base 118 and are used to brake and release casters 136 as is known in the art. Base 118 also supports a housing 119 in which portions of bed circuitry, such as some or all of bed circuitry 112 described herein, resides.

Illustrative hospital bed 102 has four siderail assemblies coupled to upper frame assembly 120 as shown in FIG. 1. The four siderail assemblies include a pair of head siderail assemblies 140 (sometimes referred to as head rails) and a pair of foot siderail assemblies 142 (sometimes referred to as foot rails). Each of the siderail assemblies 140, 142 is movable between a raised position, as shown in FIG. 1 with regard to both head rails 140 and the right foot rail 142, and a lowered position, as shown in FIG. 1 with regard to the left foot rail 142. Siderail assemblies 140, 142 are sometimes referred to herein as just siderails 140, 142. Each siderail 140, 142 includes a barrier panel 144 and a linkage 146. Each linkage 56 is coupled to the upper frame assembly 120 and is configured to guide the barrier panel 144 during movement of siderails 140, 142 between the respective raised and lowered positions.

Mattress support deck 134 of upper frame assembly 120 supports a mattress 148 which, in turn, supports the patient 114. Mattress support deck 134 is situated over an upper frame of upper frame assembly 120. In some embodiments, mattress support deck 38 includes articulated deck sections such as a head section that supports the head and torso regions of the patient 114, a seat section that supports the buttocks and sacral regions of the patient 114, a thigh section that supports the patient's thighs, and a foot section that supports the calves and feet of the patient 114. One or more of the deck sections are movable relative to the upper frame of upper frame assembly 120. For example, the head section pivotably raises and lowers relative to the seat section whereas foot section 44 pivotably raises and lowers relative to the thigh section. Additionally, the thigh section 43 articulates relative to the seat section. Also, in some embodiments, the foot section 44 is extendable and retractable to change the overall length of the foot section and therefore, to change the overall length of mattress support deck 134. Additional details of suitable embodiments of bed 102 is found, for example, in U.S. Patent Application Publication No. 2018/0161225 A1 which is hereby incorporated by reference herein for all that teaches to the extent not inconsistent with the present disclosure which shall control as to any inconsistencies.

As noted above, bed 102 includes radar support mount 104 that, in turn, supports radar sensors 106, 108, 110. In the illustrative example, radar support mount 104 includes a generally vertically oriented column or mast 104a and a generally horizontally oriented arm 104b extending in a cantilevered manner from an upper end of mast 104a so as to overlie mattress 148 of bed 102 and the patient 114 supported thereon. Arm 104b has a distal end region 104c to which radar sensor 106 is coupled. Arm 104b is situated generally vertically above a longitudinal centerline of bed 102. Radar support mount 104 further includes right and left arms 104d, 104e that extend in a cantilevered manner from right and left sides, respectively, of arm 104b. When viewed from above, arm 104b including its distal end region 104c and arms 104d, 104e resemble a cross.

In some embodiments, radar sensors 106, 108, 110 are movable along respective arms 104b, 104d, 104e so that the trajectory of the radar beams from sensors 106, 108, 110 can be adjusted by a large or gross amount as compared to the amount of adjustment possible using beam forming techniques. For example, clamps or locks associated with each of sensors 106, 108, 110 may be manually locked and released to permit sensors 106, 108, 110 to be manually repositioned along tracks, guides, rods, bars, or the like included in respective arms 104b, 104d, 104e in some contemplated embodiments. Alternatively, sensors 106, 108, 110 may be mounted to nuts that travel along lead screws which are manually rotated by hand cranks or knobs and which are included in arms 104b, 104d, 104e. Automated or motorized control of such lead screws using motors are also contemplated by the present disclosure with regard to the manner of adjusting the positions of sensors 106, 108, 110 relative to arms 104b, 104d, 104e. Other automated adjustment mechanisms for repositioning sensors 106, 108, 110 on mount 104, such as linear actuators, motorized sprocket and chain arrangements, motorized belt and pulley arrangements, and the like are also contemplated by the present disclosure. Embodiments in which arms 104d, 104e are repostionable along arm 104b in the longitudinal dimension thereof so as to move arms 104d, 104e closer to and further from distal end region 104c of arm 104b are also within the scope of the present disclosure. Similar manual and/or automated repositioning mechanisms as those described above may be used for that purpose.

In some embodiments, a lower end of mast 104a of mount 104 is coupled to the head end 124 of the upper frame of upper frame assembly 120 of bed 102. In such embodiments, therefore, radar support mount 104 and the radar sensors 106, 108, 110 supported thereby raise, lower, and tilt relative to base 118 as upper frame assembly 120 is raised, lowered, and tilted, respectively, by lift system 122. In other embodiments, the lower end of mast 104a is coupled to the head end of base 118 of bed 102. In such embodiments, mount 104 and sensors 106, 108, 110 remain stationary as upper frame assembly 120 is raised, lowered, and tilted by lift system 122 relative to base 118. As mentioned above, in still other embodiments, mount 104 comprises a freestanding frame, such as one having casters for mobility, that is moved into position over bed 102, for example.

In some embodiments, mast 104a of mount 104 is telescopic so as to lengthen and shorten in the generally vertical direction. Thus, extending mast 104a telescopically raises arms 104b, 104d, 104e and the associated radar sensors 106, 108, 110 relative to mattress 148 and the patient 114 thereon, whereas retracting mast 104a telescopically lowers arms 104b, 104d, 104e and the associated radar sensors 106, 108, 110 relative to mattress 148 and the patient 114 thereon. In such embodiments, mast 104a includes at least first and second mast segments, if not more, that are extendable and retractable relative to each other such as with the use of one or more linear actuators, lead screw drives (manual or automatic), and the like. Optionally, arm 104b of mount 104 is telescopic to move distal end region 104c and arms 104d, 104e as a unit over the mattress 148 and patient 114 in a generally horizontal direction defined by the longitudinal dimension of arm 104b. In such embodiments, arm 104b includes at least first and second arm segments, if not more, that are extendable and retractable relative to each other such as with the use of one or more linear actuators, lead screw drives (manual or automatic), and the like. The adjustability of the locations of sensors 106, 108, 110, both generally vertically and generally horizontally, as discussed above allows the disclosed patient monitoring system using radar sensors 106, 108, 110 to account for patients of different sizes and to account for the particular position of the patient 114 on bed 102 between the head end 124 and foot end 126.

It is contemplated by the present disclosure that, in some embodiments, the portions of bed circuitry 112 that control movement of portions of bed 102 communicate with the portions of circuitry 112 that controls operation of radar sensors 106, 108, 110 to alter the operation of radar sensors 106, 108, 110 under certain conditions. For example, if the head section of mattress support deck 134 is pivotably raised at a head of bed (HOB) angle that exceeds a threshold amount, say about 15 to about 30 degrees just to give an arbitrary threshold range, then use of radar sensors 106, 108, 110 may become disabled by circuitry 112 in some embodiments. This is because the inclination of the patient's torso at such steep angles may negatively affect the ability of sensors 106, 108, 110 and circuitry 112 to accurately sense the heart rate, respiration rate, and/or position of the patient. In this regard, it will be appreciated that bed 102 includes an angle sensor such as an accelerometer, inclinometer, rotary potentiometer, string potentiometer, ball switch, mercury switch, and the like that is coupled to circuitry 112 and that is used to sense the HOB angle of the head section of mattress support deck 134 of bed 102. To give another example, if circuitry 112 analyzes image intensity (e.g., lightness or darkness) of various zones of an image generated by radar sensors 106, 108, 110 (e.g., see the discussion below of FIGS. 4A-4C) and compares the light intensity to various threshold intensity values for determining the patient's heart rate, respiration rate, position, health condition, etc., it may be desirable to use different light intensity threshold values depending upon on how close the patient is to radar sensors 106, 108, 110. Thus, in some embodiments, circuitry 112 analyzes the height and/or tilt of upper frame assembly 120 relative to base 118 and/or the amount of extension or retraction of mast 104a and then adjusts the image intensity threshold values accordingly.

Figure 2:
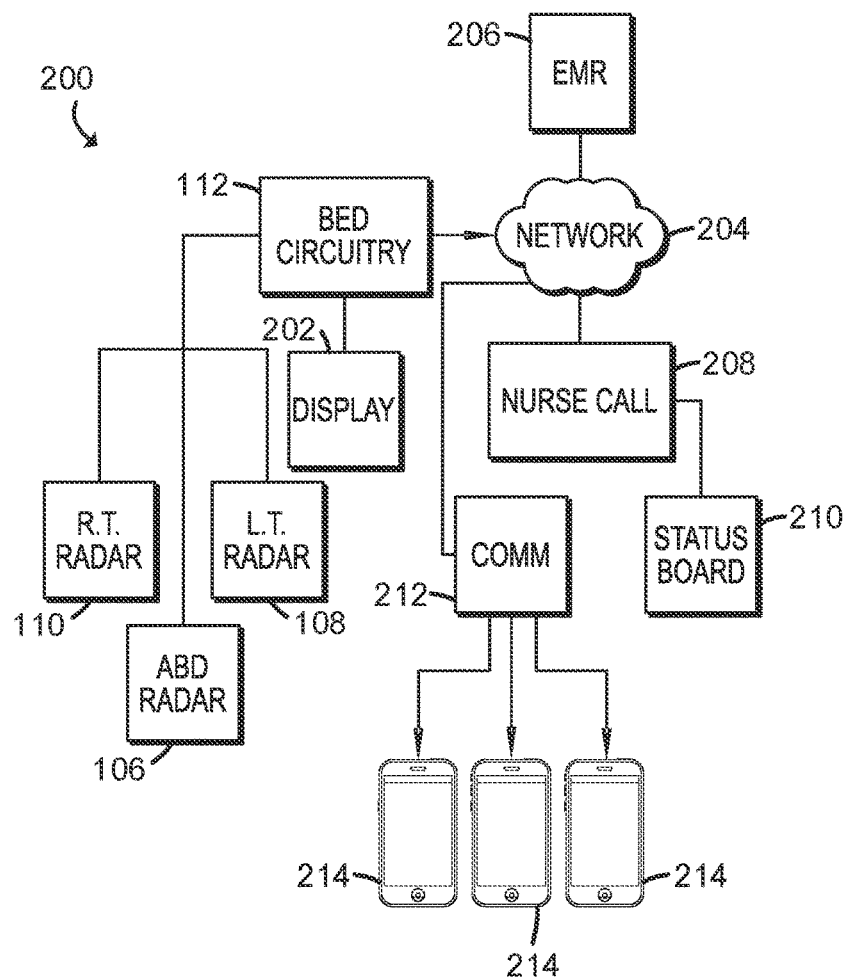
FIG. 2 is a block diagram showing one embodiment of circuitry associated with the system of FIG. 1.

Referring now to FIG. 2, a system 200 for monitoring a patient using radar sensors includes the radar sensors 106, 108, 110, the bed circuitry 112, and a display 202. The bed circuitry 112 may be connected over a network 204 to additional components, such as an electronic medical records server 206, a nurse call system 208, a status board 210, a communication system 212, and one or more mobile compute devices 214. In use, the bed circuitry 112 may communicate monitoring information of the patient to other components of the system 200. For example, the bed circuitry 112 may monitor the heart rate of a patient 114 and send the heartrate of the patient 114 to the electronic medical records server 206 to be stored as part of the medical record of the patient 114. The bed circuitry 112 may also send the heartrate of the patient 114 to the nurse call system 208, allowing the heartrate to be presented on a status board 210 and/or sent to mobile compute devices 214 carried by nurses.

The display 202 may be local to the bed circuitry 112, such as a display on one or more of the siderails 140, 142 of the patient bed 102. The display 202 may be any suitable display, such as an LCD display, an LED display, a laser display, and/or the like. The display 202 is operable under the control of circuitry 112 to show information, including image data, sensed by radar sensors 106, 108, 110 in some embodiments. Moreover, in some embodiments, display 202 comprises a graphical user interface (GUI) that is also operable to display user inputs for control of various features and functions of bed 102 including control of components associated with mattress 148 and control of movable portions of frame 116.

The network 204 may be any suitable network. In the illustrative embodiment, the network 204 is an Ethernet network. Additionally or alternatively, the network 204 may be embodied as a Wi-Fi® network, a Bluetooth® network, a WiMAX network, a near field communication (NFC) network, etc.

Figure 3:
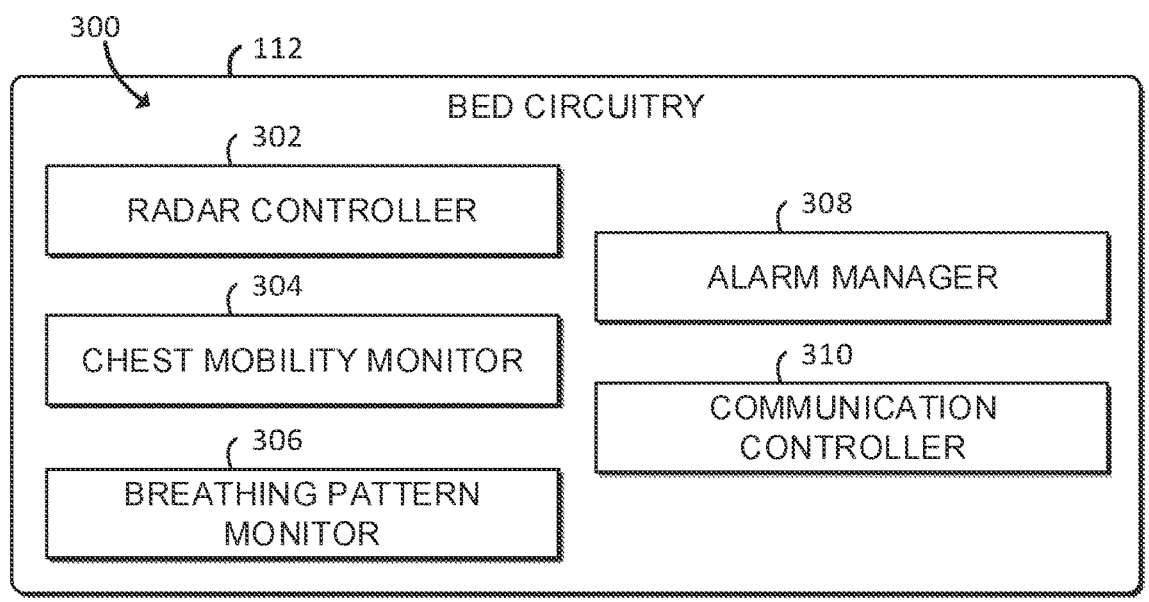
FIG. 3 is a block diagram of an environment that may be established by some or all of the circuitry of FIG. 2.

Referring now to FIG. 3, in an illustrative embodiment, the bed circuitry 112 establishes an environment 300 during operation. The illustrative environment 300 includes a radar controller 302, a chest mobility monitor 304, a breathing pattern monitor 306, an alarm manager 308, and a communication controller 310. The various modules of the environment 300 may be embodied as hardware, software, firmware, or a combination thereof. For example, the various modules, logic, and other components of the environment 300 may form a portion of, or otherwise be established by, a processor, memory, or other hardware components of the bed circuitry 112. As such, in some embodiments, one or more of the modules of the environment 300 may be embodied as circuitry or collection of electrical devices (e.g., radar controller circuitry 302, chest mobility monitor circuitry 304, breathing pattern monitor circuitry 306, etc.). It should be appreciated that, in such embodiments, one or more of the circuits (e.g., the radar controller circuitry 302, the chest mobility monitor circuitry 304, the breathing pattern monitor circuitry 306, etc.) may form a portion of one or more of the processor, the memory, the data storage, and/or other components of the bed circuitry 112. Additionally, in some embodiments, one or more of the illustrative modules may form a portion of another module and/or one or more of the illustrative modules may be independent of one another. Further, in some embodiments, one or more of the modules of the environment 300 may be embodied as virtualized hardware components or emulated architecture, which may be established and maintained by the processor or other components of the bed circuitry 112.

The radar controller 302, which may be embodied as hardware, firmware, software, virtualized hardware, emulated architecture, and/or a combination thereof as discussed above, is configured to interface with the radar sensors 106, 108, 110. The radar controller 302 may send commands to the radar sensors 106, 108, 110, configure the radar sensors 106, 108, 110, and receive data from the radar sensors 106, 108, 110. In the illustrative embodiment, the radar controller 302 receives indications of the signals received by the radar sensors 106, 108, 110, such as the intensity, phase, electric field, etc., received at each receiver of the radar sensors 106, 108, 110. In some embodiments, the radar sensors 106, 108, 110 may perform some pre-processing before sending data to the radar controller 302, such as by processing data received to determine the location and/or velocity of objects that reflected waves to the radar sensors 106, 108, 110.

Figure 4A:
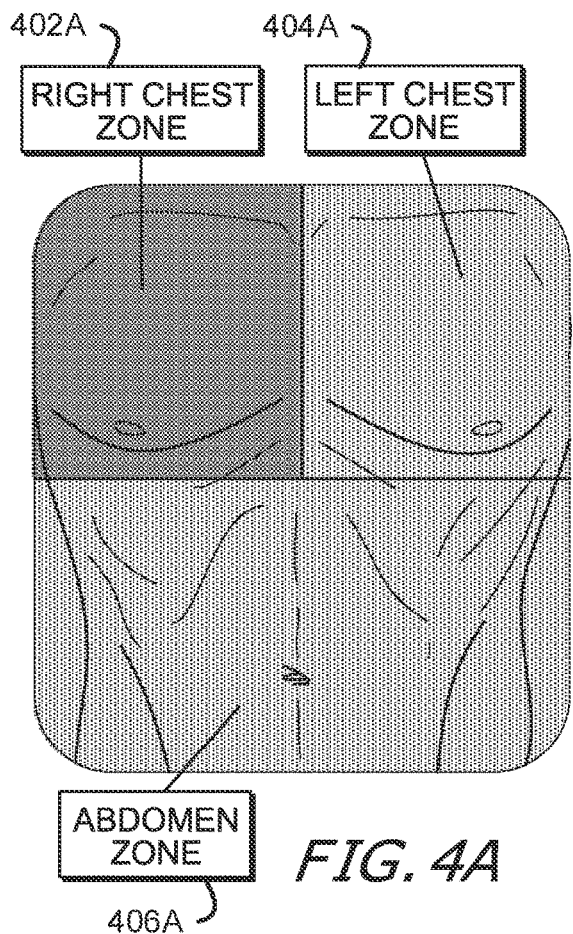
FIGS. 4A-4C depict chest and abdomen monitoring regions that can be used in one embodiment of the system of FIG. 1.
Figure 4B:
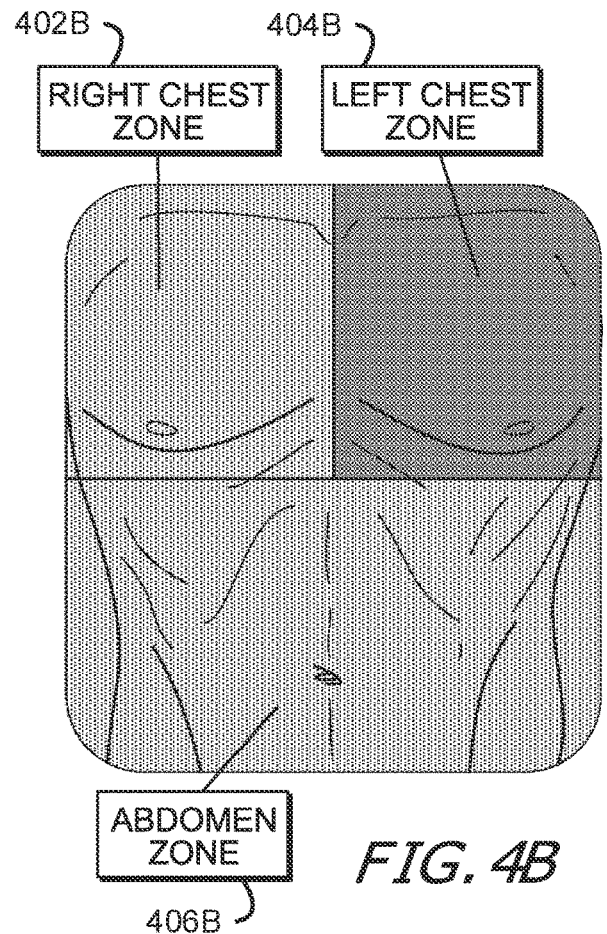
Figure 4C:
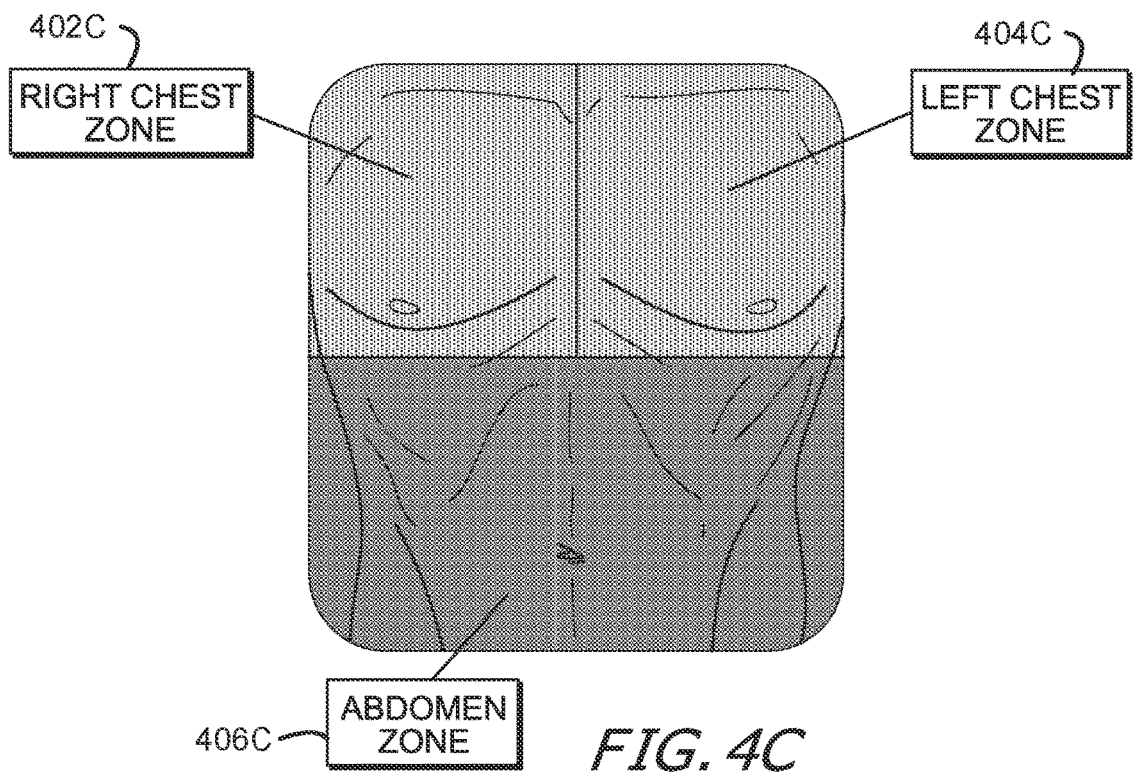

The chest mobility monitor 304, which may be embodied as hardware, firmware, software, virtualized hardware, emulated architecture, and/or a combination thereof as discussed above, is configured to analyze data from the radar sensors 106, 108, 110 to monitor the mobility of the chest of the patient 114. The chest mobility monitor 304 may monitor a position of different portions of the patient, such as the right half of the chest of the patient 114, the left half of the chest of the patient 114, and the abdomen of the patient 114. For example, in one illustrative embodiment, the chest mobility monitor 304 may monitor a right chest zone 402A, a left chest zone 404A, and an abdomen zone 406A, as shown in FIG. 4A. In FIG. 4A, the right chest zone 402A may be lagging behind the left chest zone 404A as the patient takes breaths, indicating a unilateral lung or pleural disease on the patient's right lung. In FIG. 4B, the left chest zone 404B may be lagging behind the right chest zone 402B, indicating a unilateral lung or pleural disease on the patient's right lung. In FIG. 4C, the abdomen zone 406C may not move an expected amount compared to the right chest zone 402C and the left chest zone 404C, indicating that the patient is breathing from their chest rather than their belly.

The chest mobility monitor 304 may determine various parameters related to chest mobility, such as chest expansion distance, monitor tidal volume, chest asymmetry during breathing, and belly expansion. A chest expansion distance (as measured by a change in circumference of the chest) of 2-5" may indicate a normal chest expansion distance. A chest expansion distance less than 2" (or a decrease in chest expansion distance, even if it is still about 2") may indicate a lung or pleural disease or condition. An asymmetry in the chest during breathing such as one side expanding less and/or after the other side may indicate a unilateral lung or pleural disease. A patient breathing from their chest (as opposed to their belly), which may occur, e.g., after surgery, can increase the chance of developing pneumonia. If chest breathing is detected, a patient can be coached to breathing from the belly. The chest mobility monitor 304 may store chest mobility data, locally and/or remotely, to allow for current or future analysis of chest mobility data.

The breathing pattern monitor 306, which may be embodied as hardware, firmware, software, virtualized hardware, emulated architecture, and/or a combination thereof as discussed above, is configured to analyze chest mobility data provided by the chest mobility monitor 304 to determine breathing data. The breathing pattern monitor 306 may determine parameters such as a breathing rate, breathing depth, inspiratory/expiratory time ratio. A breathing rate that is too high or too low may indicate certain conditions. Shallow breathing can be detected based on the breathing rate and breathing depth. Cheyne-Stokes breathing, in which breathing increases and decreases in depth along with recurring periods where the patient does not breathe at all. Cheyne-Stokes breathing can indicate severe head trauma and/or altitude sickness. Kussmaul breathing, in which the patient breathes deeply and rapidly, may indicate that a person is in diabetic ketoacidosis. The breathing pattern monitor 306 may store breathing data, locally and/or remotely, to allow for current or future analysis of breathing data.

The alarm manager 308, which may be embodied as hardware, firmware, software, virtualized hardware, emulated architecture, and/or a combination thereof as discussed above, is configured to determine whether an alarm should be triggered based on the chest mobility or breathing of the patient. An alarm may be triggered based on any suitable measurement of the patient's condition. For example, an alarm may be triggered if chest expansion distance drops below a threshold or changes by a threshold amount, if a tidal volume drops below a threshold amount or changes by a threshold amount, if an asymmetry in chest movement is detected during breathing, if chest breathing is detected, if a breathing rate above a threshold is detected, if a breathing rate below a threshold is detected, if shallow breathing is detected, if Cheyne-Stokes breathing is detected, and/or is Kussmaul breathing is detected. In some embodiments, a baseline for various breathing parameters may be determined based on past breathing data of a patient, and if one or more breathing parameters of the patient deviate from the baseline (such as by a specific amount and/or time), then an alarm may be triggered. The alarm manager 308 may trigger an alarm in any suitable way, such as by making a local visible or audible alarm, sending a message to be displayed on the status board 210, sending a message to one or more mobile compute devices 214 of caregivers, etc. It should be appreciated that, in some embodiments, some or all of the alarm manager 308 may be located separately from the patient bed 102 and/or separately from other components of the bed circuitry 112. For example, in some embodiments, the alarm manager 308 may form part of the nurse call system 208 or the status board 210.

The communication controller 310 is configured to communicate with other devices, such as the electronic medical records server 206 or the nurse call system 208. As discussed above, the communication controller 310 may communicate with other devices directly or indirectly through, for example, Ethernet, Bluetooth®, Wi-Fi®, WiMAX, near field communication (NFC), etc.

Figure 5:
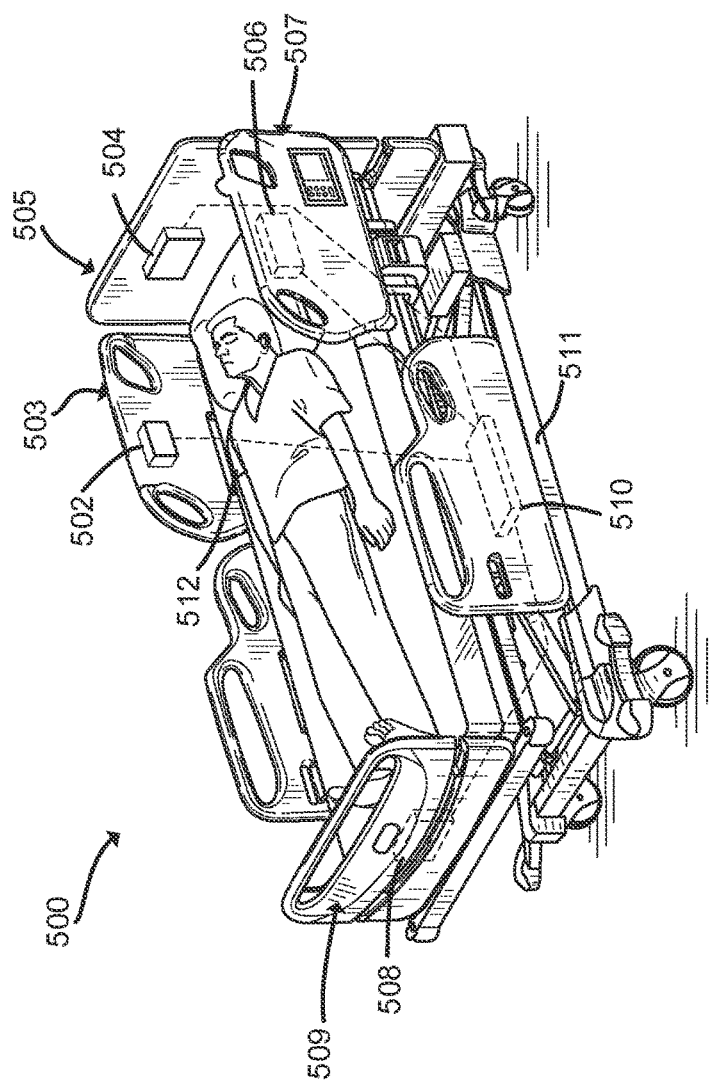
FIG. 5 is a perspective view of an alternative embodiment of a system for monitoring a patient using one or more radar sensors.
Figure 6:
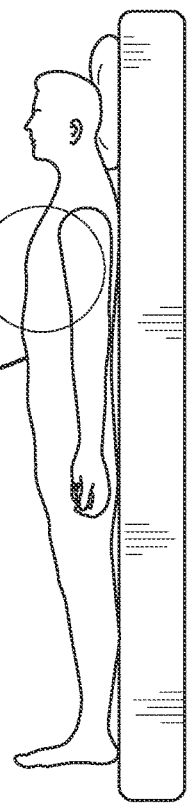
FIG. 6 is a side view of a patient that can be monitored using the system of FIG. 5.
Figure 7:
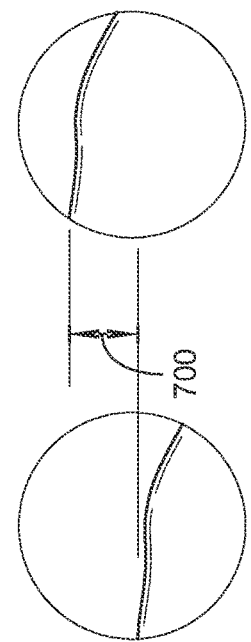
FIG. 7 is a graphic of one embodiment of a change in chest height due to a patient breathing.

It should be appreciated that the radar sensors 106, 108, 110 may be configured in different location than over the patient 114 in the patient bed 102. For example, in FIG. 5, a patient bed 500 includes a right radar sensor 502 positioned in a right siderail 503 of the patient bed 500, a head radar sensor 504 located in a headboard 505 at the head end of the patient bed 500, a left radar sensor 506 positioned in a left siderail 507 of the patient bed 500, and a foot radar sensor 508 located in a footboard 509 at the foot end of the patient bed 500. Each radar sensor 502, 504, 506, 508 is connected to bed circuitry 510 located in the patient bed 500 below the patient 512, such as on the lower frame or base 511 of bed 500. Each radar sensor 502, 504, 506, 508 (and other radar sensors discussed throughout the present disclosure) may be similar to the radar sensors 106, 108, 110, and the bed circuitry 510 (and other circuitry discussed throughout the present disclosure) may be similar to the bed circuitry 112. The description of those components, and similar components described throughout the present disclosure, will not be repeated in the interest of clarity. It should be appreciated that, instead of a top-down view, the radar sensors 502, 504, 506, 508 provide a side view of the patient as shown in FIG. 6. This view provides different measurement data compared to the radar sensors 106, 108, 110. For example, zooming in on a chest region 602 of the patient 512, a chest breathing depth 700, shown graphically in FIG. 7, may be measured based on the chest of the patient occluding different portions of the field of view of the radar sensors 502, 504, 506, 508. It should be appreciated that any combination of radar sensors 502, 504, 506, 508 and radar sensors 106, 108, and 110 may be used in various embodiments. In some embodiments, some or all of radar sensors 502, 504, 506, 508 may be used in conjunction with some or all of radar sensors 106, 108, 110, such as by measuring the same parameter such as chest movement depth from two different perspectives.

Figure 8:
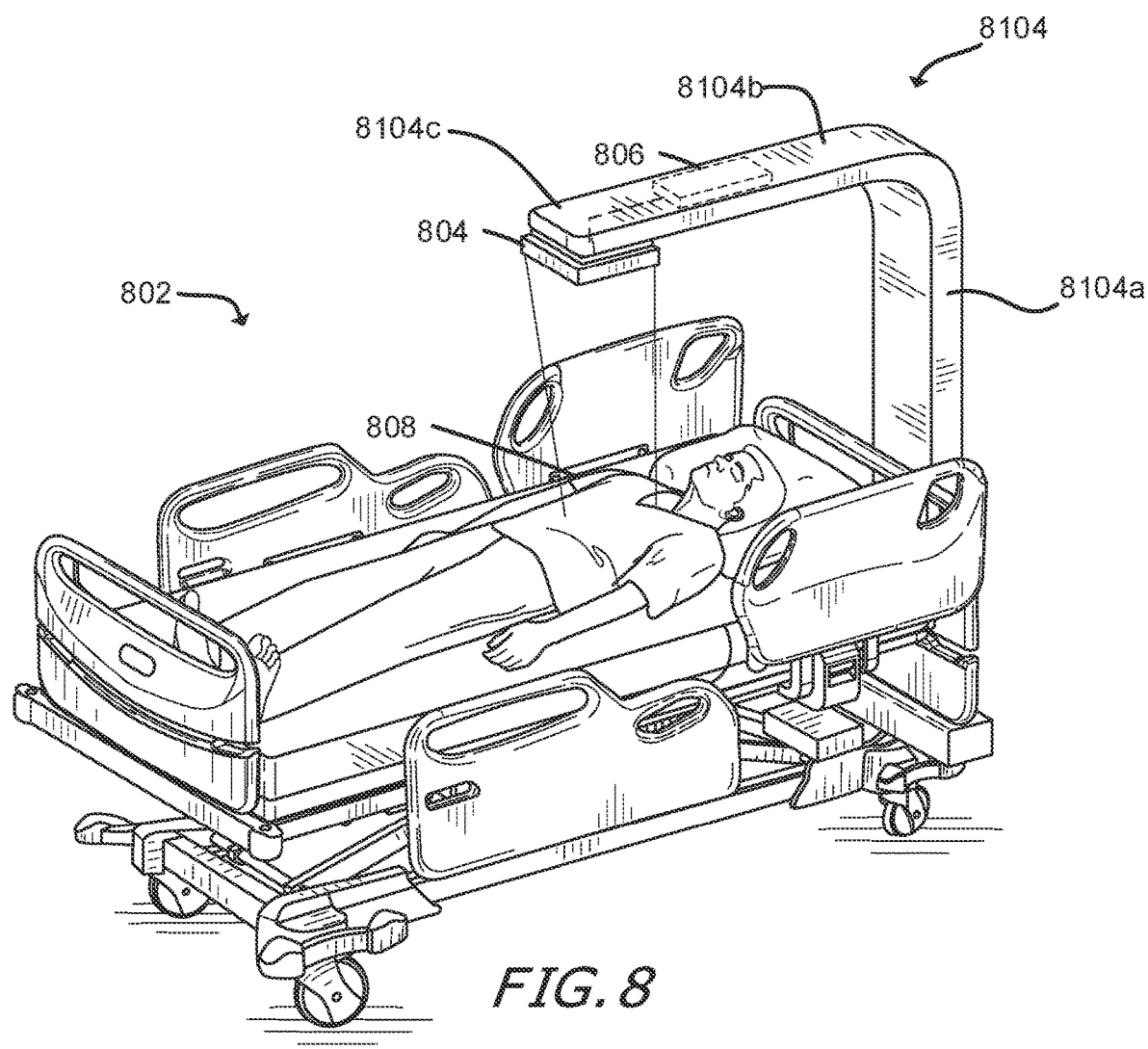
FIG. 8 is a perspective view of an alternative mobile embodiment of a system for monitoring a patient using one or more radar sensors.

In another configuration, as shown in FIG. 8, a patient bed 802 may have one or more radar sensors 804 connected to bed circuitry 806 located over the center of the patient 808 without any radar sensors on the sides. Bed 802 of FIG. 8 is substantially the same as bed 102 of FIG. 1 and so the discussion above of bed 102 is equally applicable to bed 802. Furthermore, a radar support mount 8104 is used in connection with bed 802 in the same manner as discussed above in connection with mount 104 used with bed 102. Thus, the discussion above of mount 104, including all of the variants thereof, is equally applicable to mount 8104. Thus, for example, mount 8104 includes a generally vertically oriented column or mast 8104a and a generally horizontal arm 8104b having a distal end region 8104c to which radar sensor 804 is coupled. The discussion above of mast 104a is equally applicable to mast 8104a and the discussion above of arm 104b is equally applicable to arm 8104b.

Figure 9:
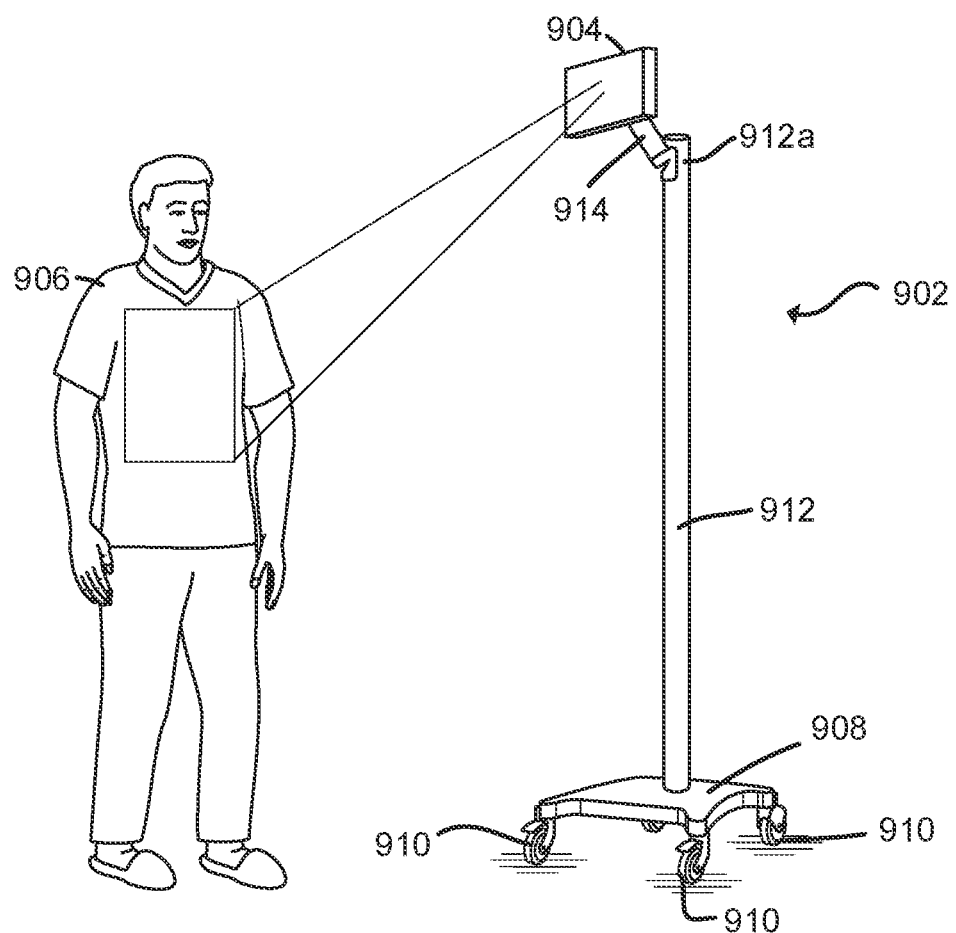
FIG. 9 is a perspective view of an alternative embodiment of a system for monitoring a patient using one or more radar sensors.

In another configuration, as shown in FIG. 9, a standalone mobile radar unit 902 may have a radar sensor 904 positioned near the top of the mobile radar unit 902. The radar sensor 904 may be configured to monitor a chest area of a patient 906 as suggested by the diagrammatic rectangular box shown on patient 906 in FIG. 9. Each of the components identified in FIGS. 8 & 9 may be similar to the corresponding components identified in FIG. 1, the description of which will not be repeated in the interest of clarity. Mobile radar unit 902 includes a wheeled base 908 having casters 910 coupled thereto. Mobile radar unit 902 further includes a generally vertically oriented pole or mast 912 extending upwardly from base 908. A pivotable arm 914 extends from an upper region 912a of pole 912 and radar sensor 904 is mounted to a distal end of arm 914 in spaced relation with pole 912. Arm 914 is pivotable upwardly and downwardly relative to pole 912 to adjust a height at which radar sensor 904 is supported above the floor.

In some embodiments, arm 914 is movable vertically along pole 912 to provide further adjustment of the vertical position of radar sensor 904 relative to the floor. For example, a lockable and releasable collar may be coupled to pole 912 and arm 914 may extend from the collar. When released, the collar is movable upwardly and downwardly along pole 912 and then lockable in the desired position. A clamp, lock, thumb screw, or similar releasable locking device is provided in some embodiments for locking the collar relative to pole 912. Mobile radar unit 902 with radar sensor 904 is well suited for obtaining patient monitoring data from patients who are standing up such as may be the case during a medical examination at a doctor's office, for example.

Figure 10A:
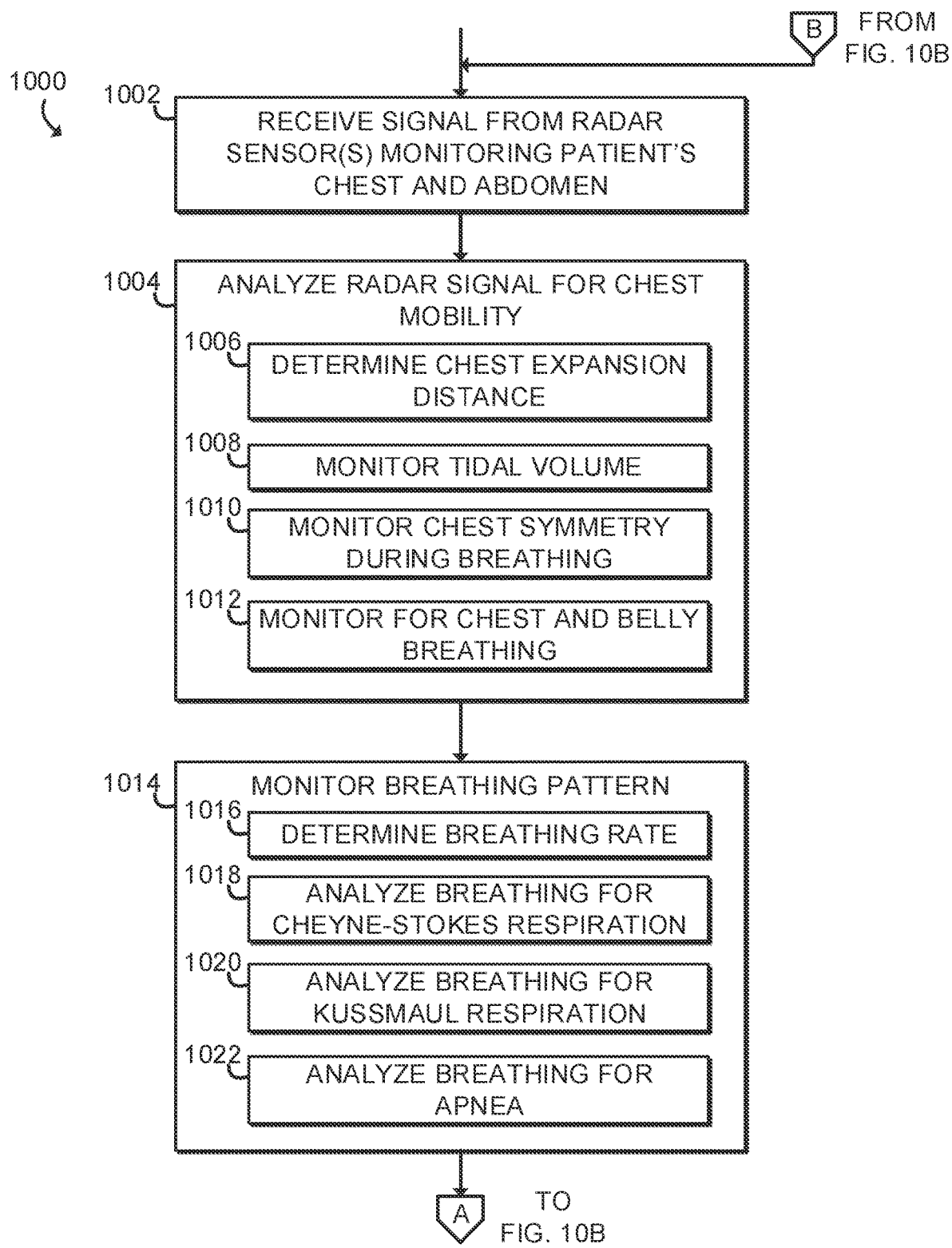
FIGS. 10A & 10B are a flowchart for one embodiment of a method to monitor breathing patterns using one of the systems of FIG. 1, 5, 8, or 9.

Referring now to FIG. 10A, in use, a method 1000 for monitoring a patient with radar may be performed. In some embodiments, some or all of the method 1000 may be performed by the bed circuitry 112. Additionally or alternatively, in some embodiments, the bed circuitry 112 may provide data such as a breathing rate, and a caregiver may monitor the data from the bed circuitry 112 to determine whether the patient has, e.g., Cheyne-Stokes breathing. The method 1000 begins in block 1002, in which the bed circuitry 112 receives a signal from one or more radar sensors 106, 108, 110 monitoring a patient's chest and abdomen. The bed circuitry 112 may receive the raw signal received by an antenna of a radar sensor 106, 108, 110. In some embodiments, the radar sensors 106, 108, 110 may perform some pre-processing before sending data to the bed circuitry 112, such as by processing data received to determine the location and/or velocity of objects that reflected waves to the radar sensors 106, 108, 110.

In block 1004, the bed circuitry 112 analyzes the radar signal for chest mobility. The bed circuitry 112 may group the patient's chest into areas, such as a right chest area, a left chest area, and an abdomen area. The bed circuitry 112 may determine a position and/or velocity of each area. Of course, it should be appreciated that the radar signal may be analyzed in many different ways to determine mobility of the patient's chest.

In block 1006, the bed circuitry 112 determines the chest expansion distance. In the illustrative embodiment, the bed circuitry 112 determines a circumference of the patient's chest, and the chest expansion distance is the change in circumference of the patient's chest over the course of one or more breaths. Additionally or alternatively, in some embodiments the bed circuitry 112 may monitor a change in height of the patient's chest, and use the change in height as an indication of the chest expansion distance. See FIG. 7 and the above discussion thereof in this regard.

In block 1008, the bed circuitry 112 determines the tidal volume over the course of one breath. For example, a change in volume of the patient's chest between a minimum and maximum value over a relatively short time frame, such as about five to about ten seconds, may be attributable to the volume of air inhaled and then exhaled by the patient. In block 1010, the bed circuitry 112 monitors chest asymmetry during breathing. The bed circuitry 112 may do so by monitoring the height over time of the right chest area compared to the left chest area. If the height of one chest area peaks at a lower value and/or lags behind the other chest area, the patient may have an asymmetry in breathing. See FIGS. 4A and 4B and the above discussion thereof in this regard.

In block 1012, the bed circuitry 112 monitors for chest and belly breathing. To do so, the bed circuitry 112 may determine whether the abdomen area expands at least a threshold amount when the patient takes a breath. See FIG. 4C and the above discussion thereof in this regard.

In block 1014, the bed circuitry 112 monitors the breathing pattern of the patient. The bed circuitry 112 may determine a breathing rate in block 1016. The bed circuitry 112 may analyze the patient's breathing for Cheyne-Stokes breathing in block 1018, in which breathing increases and decreases in depth along with recurring periods where the patient does not breathe at all. Cheyne-Stokes breathing can indicate severe head trauma and/or altitude sickness. The bed circuitry 112 may analyze the patient's breathing for Kussmaul respiration in block 1020, in which the patient breathes deeply and rapidly and may indicate that a person is in diabetic ketoacidosis. In block 1022, the bed circuitry 112 may analyze the breathing pattern of the patient for apnea.

Figure 10B:
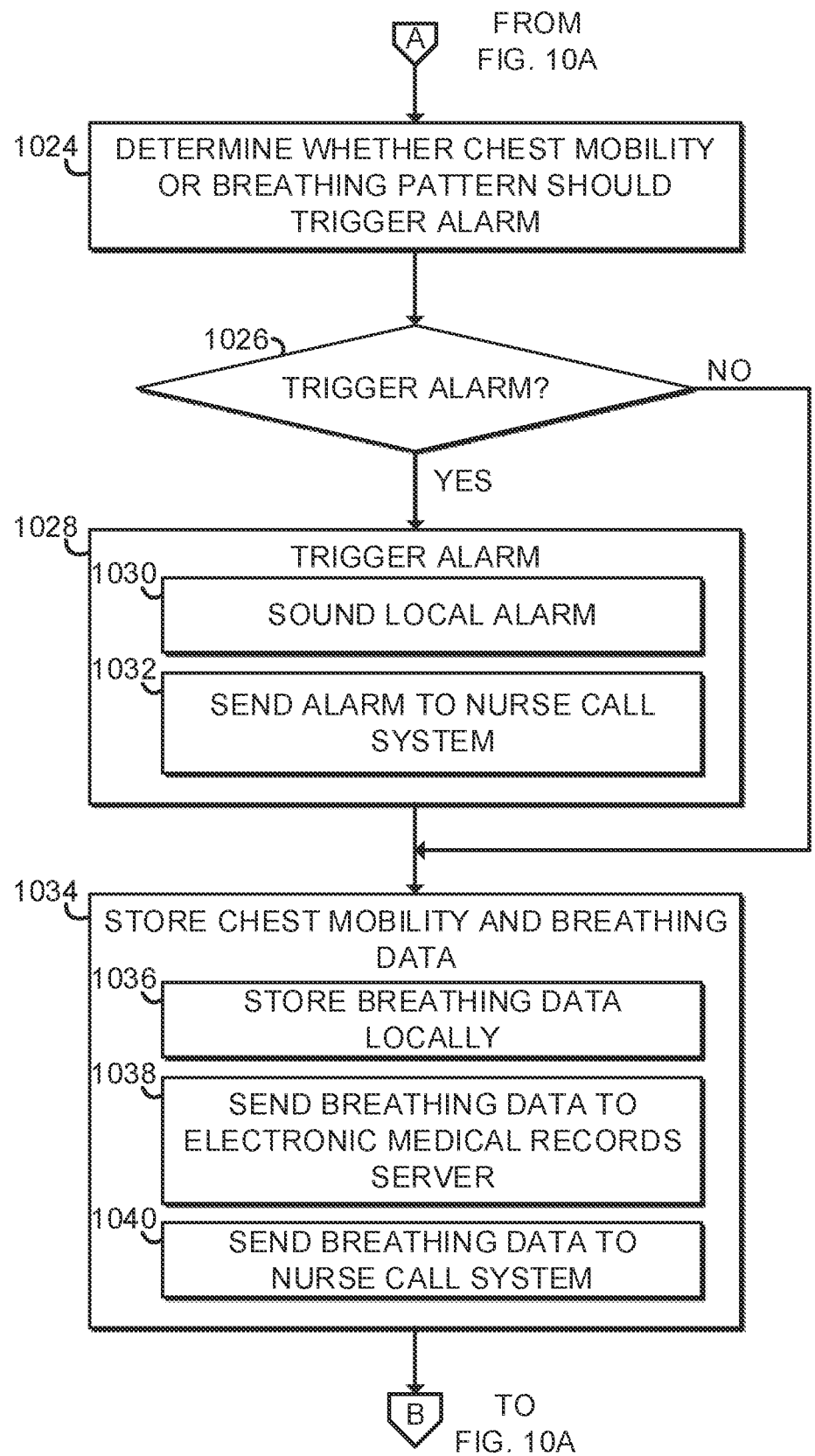

The method 1000 proceeds to block 1024 in FIG. 10B, in which the bed circuitry 112 determines whether the chest mobility and/or breathing pattern of the patient indicates that an alarm should be triggered. The bed circuitry 112 may be configured to trigger an alarm based on any suitable measurement of the patient's condition. For example, an alarm may be triggered if chest expansion distance drops below a threshold or changes by a threshold amount, if a tidal volume drops below a threshold amount or changes by a threshold amount, if an asymmetry in chest movement is detected during breathing, if chest breathing is detected, if a breathing rate above a threshold is detected, if a breathing rate below a threshold is detected, if shallow breathing is detected, if Cheyne-Stokes breathing is detected, and/or is Kussmaul breathing is detected.

In block 1026, if an alarm is not to be triggered, the method 1000 jumps to block 1034, in which the chest mobility and breathing data is stored. If the alarm is to be triggered, the method proceeds to block 1028, in which the bed circuitry 112 triggers an alarm. The bed circuitry 112 may trigger a local alarm, such as by making a local visible or audible alarm, in block 1030. Additionally or alternatively, the bed circuitry 112 may trigger a remote alarm, such as by sending an alarm to the nurse call system 208 in block 1032. The alarm may result in a message being displayed on the status board 210, a message being sent to one or more mobile compute devices 214 of caregivers, a message being displayed on a display of bed 102, etc. It should be appreciated that, in some embodiments, some or all of the analysis of whether an alarm should be triggered may be performed separately from the patient bed 102 and/or separately from at least some components of the bed circuitry 112. For example, in some embodiments, the nurse call system 208 may determine whether to trigger an alarm.

In block 1034, the bed circuitry 112 stores chest mobility and breathing data. The bed circuitry 112 may store the chest and mobility breathing data locally in block 1036, which can then be used to determine, e.g., if there is a change in a rate of a patient's breathing. Additionally or alternatively, in some embodiments, the bed circuitry 112 may send chest mobility and breathing data to an electronic medical records server in block 1038 and/or send chest mobility and breathing data to a nurse call system in block 1040. The method 1000 then loops back to block 1002 in FIG. 10A to receive additional data from radar sensors 106, 108, 110.

Figure 11:
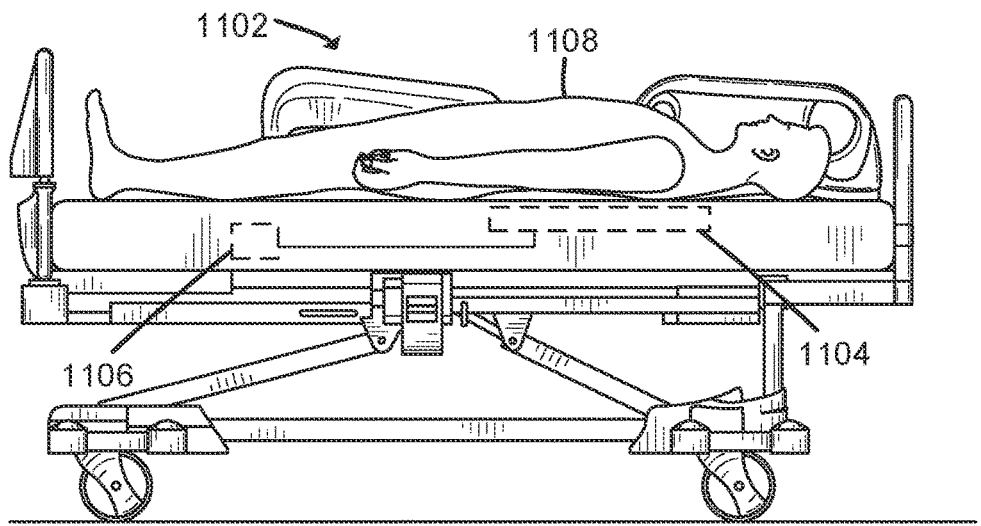
FIG. 11 is a side view of an alternative embodiment of a system for monitoring a patient using one or more radar sensors.

Referring now to FIG. 11, a patient bed 1102 may include a radar sensor 1104 connected to bed circuitry 1106 that is embedded in or below a mattress of the patient bed so that the radar sensor 1104 is below the patient 1108. Bed 1102 of FIG. 11 is substantially the same as bed 102 of FIG. 1 and therefore, the discussion above of bed 102 is equally applicable to bed 1102. In use and as described in more detail below, the radar sensor 1104 may be used to monitor breathing sounds of the patient 1108 and to determine whether the patient is, e.g., wheezing. It should be appreciated that, in some embodiments, the radar 1104 positioned below the patient 1106 may be used to monitor chest mobility and/or breathing patterns, as described above in regard to radar sensors 106, 108, 110. Additionally or alternatively, it should be appreciated that, in some embodiments, the radar sensors 106, 108, 110 may be used in a similar manner as the radar sensor 1104 to detect the sound of the patient 114 breathing. Each of the radar sensor 1104 and the bed circuitry 1106 may be similar to the radar sensors 106, 108, 110 and bed circuitry 112, respectively, the description of which will not be repeated in the interest of clarity. Additional details of the use of one or more radar sensors in mattresses or adjacent to mattresses, such as being situated on the mattress support deck beneath the mattress, can be found in U.S. Patent Application Publication Nos. 2019/0015277 A1 and 2019/0167500 A1, each of which is hereby incorporated by reference herein in its entirety to the extent not inconsistent with the present disclosure which shall control as to any inconsistencies.

Figure 12:
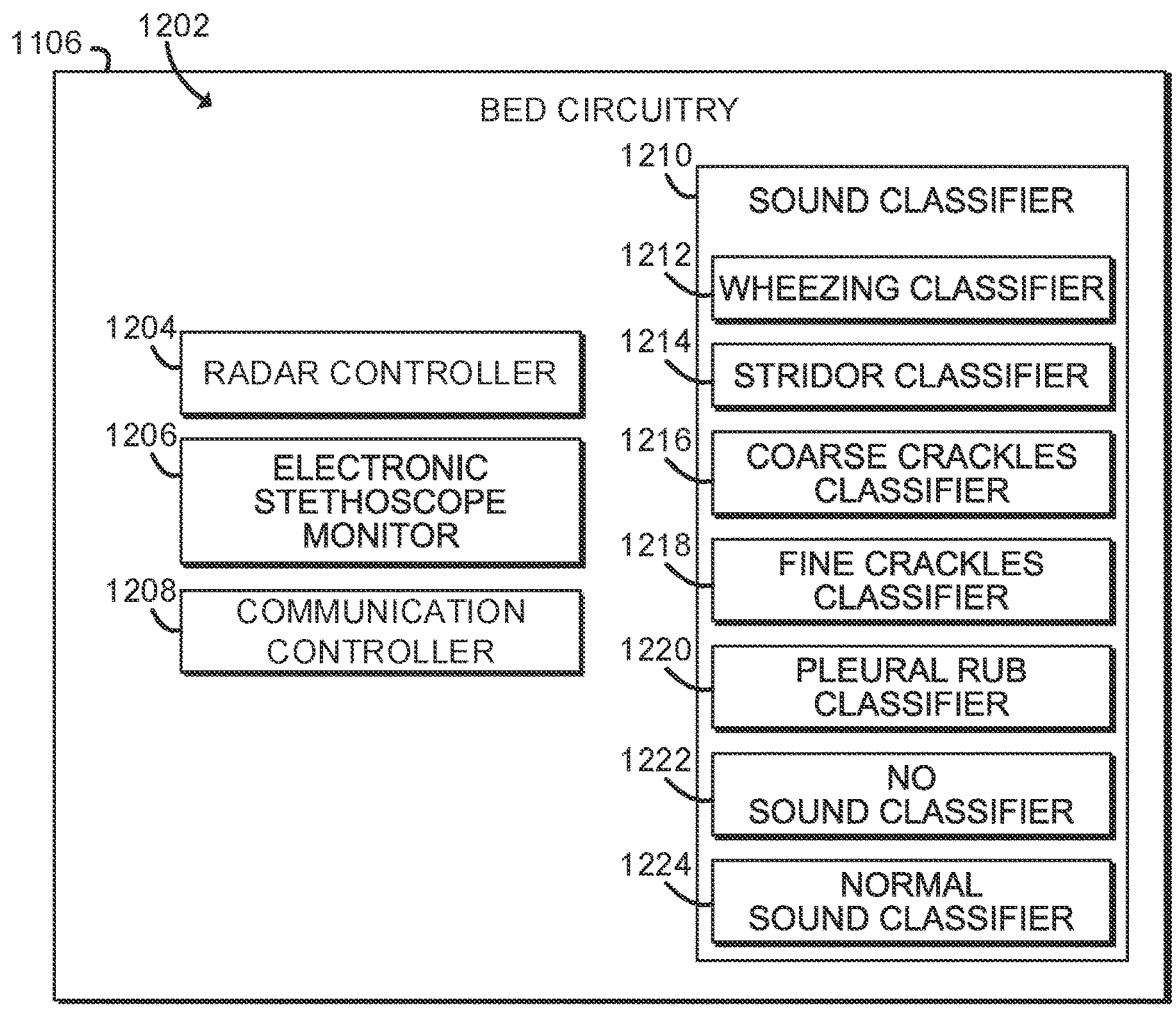
FIG. 12 is an environment that may be established by bed circuitry of the system of FIG. 11.

Referring now to FIG. 12, in an illustrative embodiment, the bed circuitry 1106 may establish an environment 1202 during operation. The illustrative environment 1202 includes a radar controller 1204, an electronic stethoscope monitor 1206, a communication controller 1208, and a sound classifier 1210. The various modules of the environment 1202 may be embodied as hardware, software, firmware, or a combination thereof. For example, the various modules, logic, and other components of the environment 1202 may form a portion of, or otherwise be established by, a processor, memory, or other hardware components of the bed circuitry 1106. As such, in some embodiments, one or more of the modules of the environment 1202 may be embodied as circuitry or collection of electrical devices (e.g., radar controller circuitry 1104, electronic stethoscope monitor circuitry 1206, communication controller circuitry 1208, etc.). It should be appreciated that, in such embodiments, one or more of the circuits (e.g., the radar controller circuitry 1104, the electronic stethoscope monitor circuitry 1206, the communication controller circuitry 1208, etc.) may form a portion of one or more of the processor, the memory, the data storage, and/or other components of the bed circuitry 1106. Additionally, in some embodiments, one or more of the illustrative modules may form a portion of another module and/or one or more of the illustrative modules may be independent of one another. Further, in some embodiments, one or more of the modules of the environment 1202 may be embodied as virtualized hardware components or emulated architecture, which may be established and maintained by the processor or other components of the bed circuitry 1106.

The radar controller 1204, which may be embodied as hardware, firmware, software, virtualized hardware, emulated architecture, and/or a combination thereof as discussed above, is configured to interface with the radar sensor 1104. The radar controller 1204 may send commands to the radar sensor 1104, configure the radar sensor 1104, and receive data from the radar sensor 1104. In the illustrative embodiment, the radar controller 1204 receives indications of the signals received by the radar sensor 1104 such as the intensity, phase, electric field, etc., received at each receiver of the radar sensor 1104. In some embodiments, the radar sensor 1104 may perform some pre-processing before sending data to the radar controller 1204, such as by processing data received to produce a sound waveform corresponding to the sound of the patient 1108 breathing.

The electronic stethoscope monitor 1206, which may be embodied as hardware, firmware, software, virtualized hardware, emulated architecture, and/or a combination thereof as discussed above, is configured to analyze the radar signal received from the radar controller 1204 to generate a sound waveform corresponding to the user breathing. In some embodiments, the electronic stethoscope monitor 1206 may apply a spatial filter to information received from the radar controller 1204 so that a particular spatial location (such as a user's back) is used to generate the sound waveform. Additionally or alternatively, the electronic stethoscope monitor 1206 may apply one or more filters or amplifiers to the generated sound waveform.

The communication controller 1208 is configured to communicate with other devices, such as the electronic medical records server 206 or the nurse call system 208. The communication controller 1208 may communicate with other devices directly or indirectly through, for example, Ethernet, Bluetooth®, WiMAX, near field communication (NFC), etc.

The sound classifier 1210, which may be embodied as hardware, firmware, software, virtualized hardware, emulated architecture, and/or a combination thereof as discussed above, is configured to classify the sound waveform generated by the electronic stethoscope monitor 1206. The sound classifier 1210 may apply a wheezing classifier 1212. The wheezing classifier 1212 may monitor for wheezing sounds, such as variable high pitched but continuous sound on expiration. Wheezing sounds may be an indication of asthma, chronic obstructive pulmonary disorder (COPD), allergies, or anaphylaxis.

The sound classifier 1210 may apply a stridor classifier 1214. The stridor classifier 1214 may monitor for stridor sounds of a single high pitched sound that is continuous on inspiration. Stridor may be an indication of croup, epiglottitis, or a foreign object.

The sound classifier 1210 may apply a coarse crackles classifier 1216. The coarse crackles classifier 1216 may monitor for low pitch, brief, discontinuous popping/bubbling sounds on inspiration and/or expiration. The coarse crackles may be cleared by the patient 1108 coughing. Coarse crackles may be an indication of pneumonia, bronchitis, asbestosis, or pulmonary edema.

The sound classifier 1210 may apply a fine crackles classifier 1218. The fine crackles classifier 1218 may monitor for higher pitched, fine popping noises during the late inspiratory phase. Fine crackles may be an indication of atelectasis, pulmonary fibrosis, or pulmonary edema.

The sound classifier 1210 may apply a pleural rub classifier 1220. The pleural rub classifier 1220 may monitor for a creaking or grating sound during inspiration. A pleural rub sound may indicate inflammation of the pleura due to infection, injury, or tumor.

The sound classifier 1210 may apply a no sound classifier 1222. No sound may indicate that the patient is not breathing or that the patient 1108 has moved, such as gotten out of the patient bed 1102. In some embodiments, the sound classifier 1210 may classify no sound as apnea if the patient 1108 is still in the patient bed 1102 and has not moved since a previous breath. Patient presence in bed 1102 may be determined based on a weigh scale system and/or patient position monitoring (PPM) system of the bed, such as those that use load cells to sense patient weight on a bed.

The sound classifier 1210 may apply a normal sound classifier 1224. The normal sound classifier may be configured to determine when the patient 1108 has a normal breathing sound. It should be appreciated that, in some embodiments, the sound classifier 1210 may be able to classify and/or ignore other sounds, such as sounds of a patient eating, talking, hiccoughing, etc.

Figure 13A:
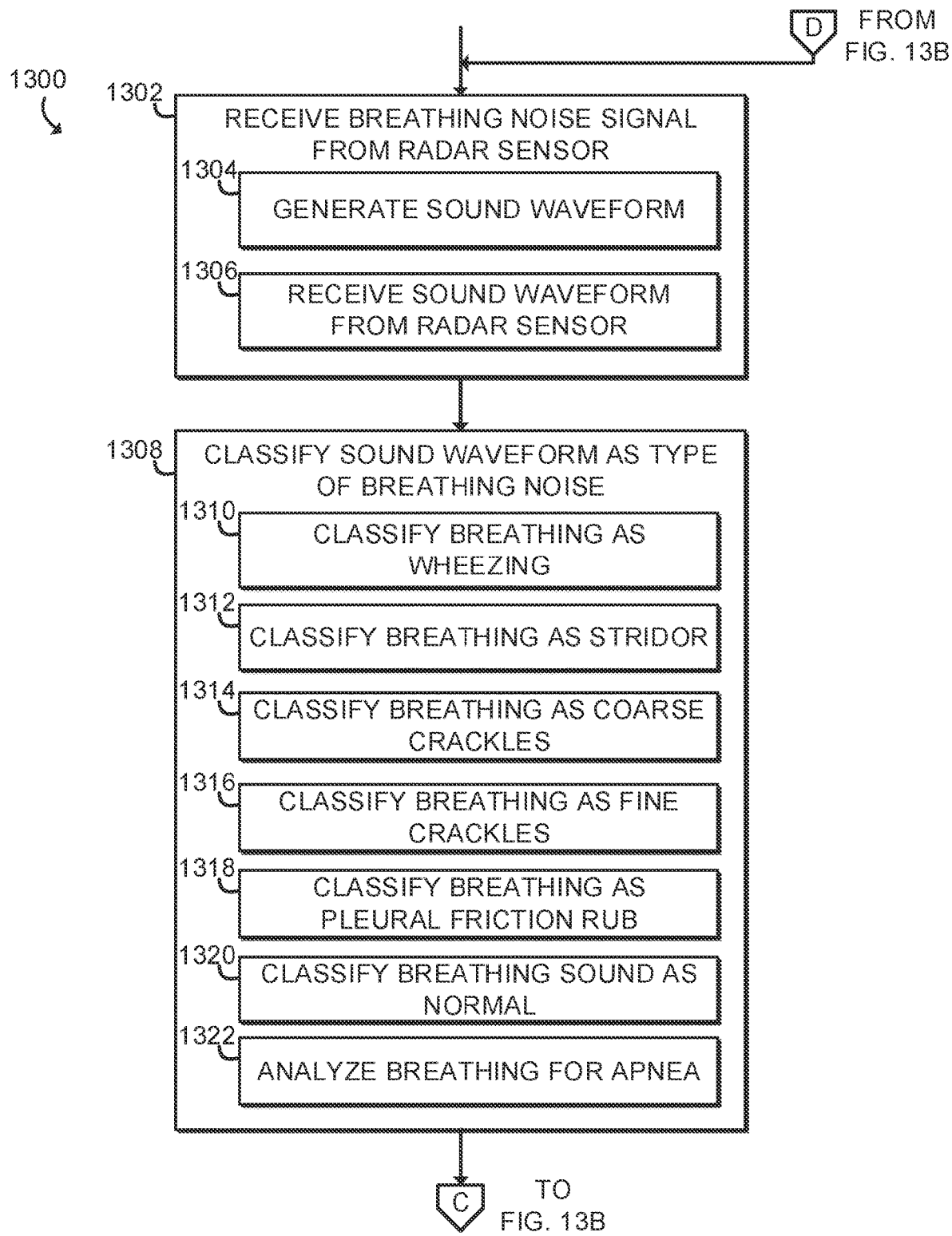
FIGS. 13A & 13B are a flowchart for one embodiment of a method to monitor breathing that may be executed by the system of FIG. 11.

Referring now to FIG. 13A, in use, a method 1300 for monitoring a patient with radar may be performed. In some embodiments, some or all of the method 1300 may be performed by the bed circuitry 1106. Additionally or alternatively, in some embodiments, certain portions of the method 1300 may be performed by a person, such as a caregiver of the patient. For example, the bed circuitry 1106 may provide data such as a sound waveform, and a caregiver may listen to the waveform data from the bed circuitry 1106 to determine, e.g., whether the patient is breathing. The method 1300 begins in block 1302, in which the bed circuitry 1106 receives a noise signal from a radar sensor 1104. In the illustrative embodiment, the bed circuitry 1106 generates a sound waveform based on the radar signal in block 1304. In some embodiments, the bed circuitry 1106 may receive a sound waveform from the radar sensor 1104 in block 1306.

In block 1308, the bed circuitry 1106 classifies the sound waveform as a type of breathing noise. The bed circuitry 1106 may classify the sound waveform as wheezing in block 1310. The bed circuitry 1106 may monitor for wheezing sounds, such as variable high pitched but continuous sound on expiration. Wheezing sounds may be an indication of asthma, chronic obstructive pulmonary disorder (COPD), allergies, or anaphylaxis.

The bed circuitry 1106 may classify the sound waveform as stridor in block 1312. The bed circuitry 1106 may monitor for stridor sounds of a single high pitched sound that is continuous on inspiration. Stridor may be an indication of croup, epiglottitis, or a foreign object.

The bed circuitry 1106 may classify the sound waveform as coarse crackles in block 1314. The bed circuitry 1106 may monitor for low pitch, brief, discontinuous popping/bubbling sounds on inspiration and/or expiration. The coarse crackles may be cleared by the patient 1108 coughing. Coarse crackles may be an indication of pneumonia, bronchitis, asbestosis, or pulmonary edema.

The bed circuitry 1106 may classify the sound waveform as fine crackles in block 1316. The bed circuitry 1106 may monitor for higher pitched, fine popping noises during the late inspiratory phase. Fine crackles may be an indication of atelectasis, pulmonary fibrosis, or pulmonary edema.

The bed circuitry 1106 may classify the sound waveform as a pleural rub in block 1318. The bed circuitry 1106 may monitor for a creaking or grating sounds during inspiration. A pleural rub sound may indicate inflammation of the pleura due to infection, injury, or tumor.

The bed circuitry 1106 may classify the sound waveform as normal in block 1320. The bed circuitry 1106 may be configured to determine when the patient 1108 has a normal breathing sound.

The bed circuitry 1106 may classify the sound waveform as apnea in block 1322. The bed circuitry 1106 may classify the sound waveform as apnea if no breathing sound is detected and the patient 1108 is still in the patient bed 1102.

Figure 13B:
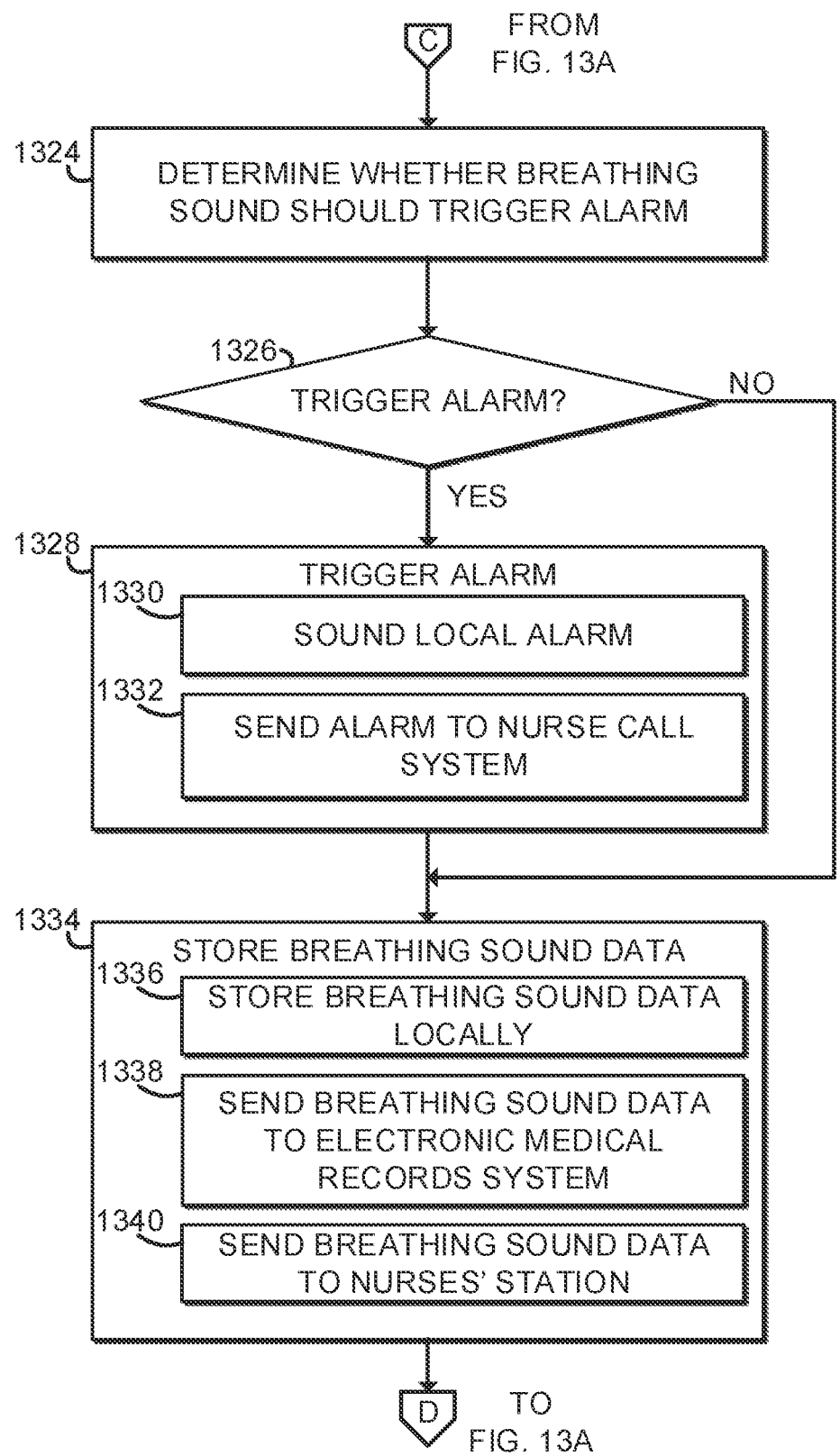

The method 1300 proceeds to block 1324 in FIG. 13B, in which the breathing sound indicates that an alarm should be triggered. The bed circuitry 1106 may be configured to trigger an alarm based on any suitable measurement of the patient's condition. For example, an alarm may be triggered if wheezing is detected, if stridor is detected, if coarse crackles are detected, if fine crackles are detected, if a pleural friction rub is detected, or if apnea is detected.

In block 1326, if an alarm is not to be triggered, the method 1300 jumps to block 1334, in which the breathing sound data is stored. If the alarm is to be triggered, the method proceeds to block 1328, in which the bed circuitry 1106 triggers an alarm. The bed circuitry 1106 may trigger a local alarm, such as by making a local visible or audible alarm, in block 1330. Additionally or alternatively, the bed circuitry 1106 may trigger a remote alarm, such as by sending an alarm to the nurse call system 208 in block 1332. The alarm may result in a message being displayed on the status board 210, a message being sent to one or more mobile compute devices 214 of caregivers, etc. It should be appreciated that, in some embodiments, some or all of the analysis of whether an alarm should be triggered may be performed separately from the patient bed 102 and/or separately from at least some components of the bed circuitry 1106. For example, in some embodiments, the nurse call system 208 may determine whether to trigger an alarm.

In block 1334, the bed circuitry 1106 stores breathing sound data. The bed circuitry 1106 may store the chest and mobility breathing data locally in block 1336, which can then be used to determine, e.g., if there is a change in a sound of a patient's breathing. Additionally or alternatively, in some embodiments, the bed circuitry 1106 may send breathing sound data to an electronic medical records server in block 1338 and/or send breathing sound data to a nurse call system in block 1340. The method 1300 then loops back to block 1302 in FIG. 13A to receive additional data from the radar sensor 1104.

Figures 14, 15:
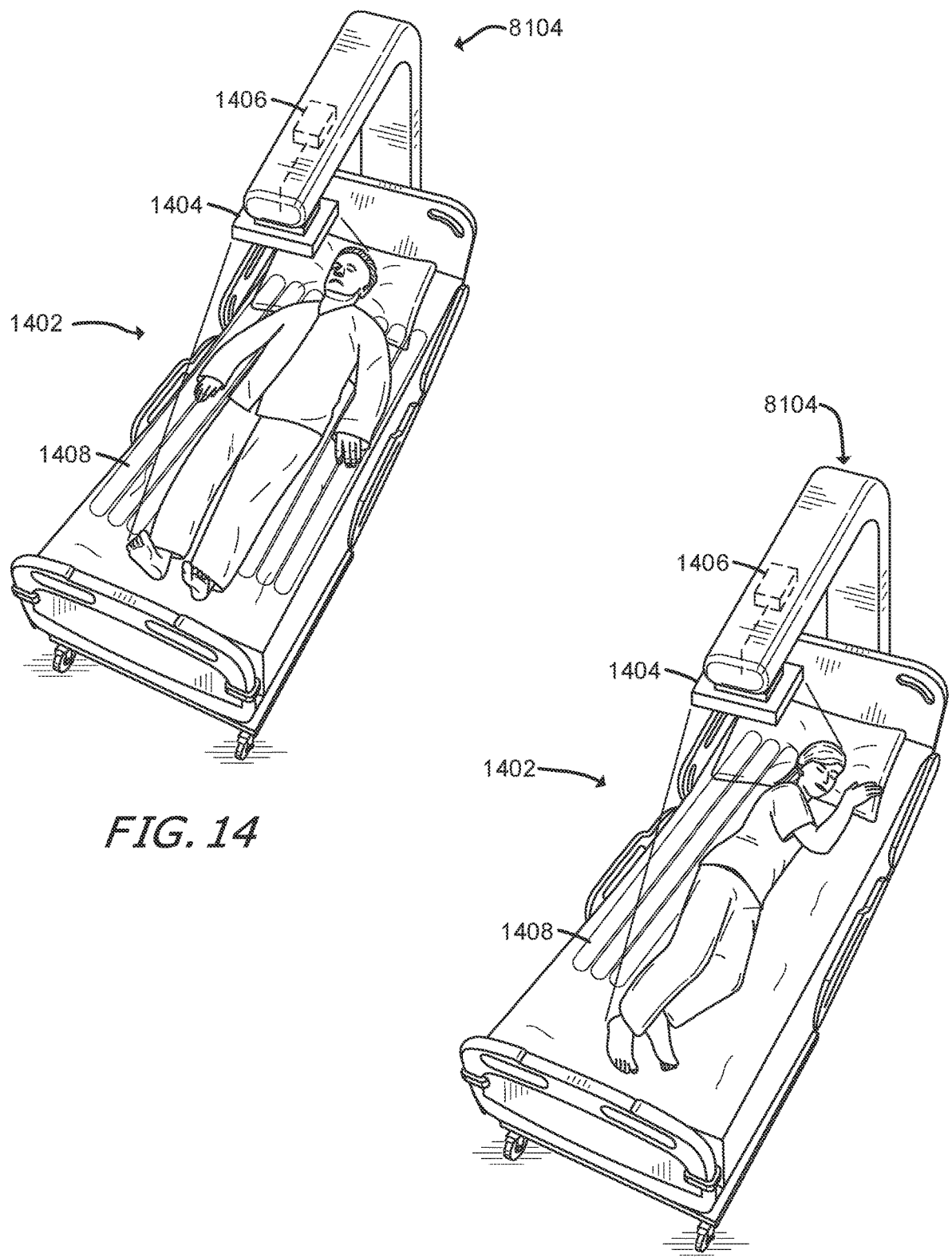
FIG. 14 is a perspective view of one embodiment of a system for monitoring a patient's position using one or more radar sensors.
FIG. 15 is a perspective view of one embodiment of a system for monitoring a patient's position using one or more radar sensors.

Referring now to FIGS. 14 and 15, in one embodiment, a patient bed 1402 includes one or more radar sensors 1404 connected to bed circuitry 1406. In the illustrative example, radar support mount 8104 is used to support the one or more radar sensors 1404 and circuitry 1406. Mount 810 was discussed above in connection with FIG. 8 and the discussion is equally applicable to the use of mount 810 with bed 1402 of FIGS. 14 and 15. The patient bed 1402 also includes one or more rotation bladders 1408 that can inflate, causing a patient to rotate. For example, the rotation bladders 1408 may inflate to rotate a patient from lying in a supine position as shown in FIG. 14 to a patient lying on the patient's left side, as shown in FIG. 15.

In use, the bed circuitry 1406 may be configured to monitor a position of the patient using the radar sensor 1404 and turn the patient as necessary. The radar sensor 1404 can be used to both determine when the patient moves and to determine where a patient is. For example, if a patient has not rotated within a certain amount of time, such as the past two hours, the bed circuitry 1406 may inflate the rotation bladders 1408 to cause the patient to rotate to the patient's side (or deflate the rotation bladders 1408 to rotate the patient back to a supine position). In some embodiments, the bed circuitry 1406 may be configured to determine a position of the patient on the bed using the radar sensor 1406, and then inflate the rotation bladders 1408 that would cause the most rotation, such as the rotation bladders 1408 that are under the patient's right side if the patient is to be rotated on her left side, as shown in FIG. 15. Additionally or alternatively, the rotation bladders 1408 can be used to reposition a patient to a desired position Referring now to FIG. 16, in one embodiment, a patient bed 1602 includes one or more radar sensors 1604 connected to bed circuitry 1606. Furthermore, a radar support mount 1605 is used in connection with bed 1602 in the same manner as discussed above in connection with mount 104 used with bed 102 of FIG. 1 and mount 8104 used with bed 802 of FIG. 8. Thus, the discussion above of mounts 104, 8104, including all of the variants thereof, is equally applicable to mount 1605. Thus, for example, mount 1605 includes a generally vertically oriented column or mast 1605a and a generally horizontal arm 1605b having a distal end region 1605c to which radar sensor 1604 is coupled. The discussion above of mast 104a and mast 8104a is equally applicable to mast 1605a and the discussion above of arm 104b and arm 8104b is equally applicable to arm 1605b. In the illustrative example of FIG. 16, radar support mount 1605 has a floor supported base 1605g without casters. Thus, it is contemplated that mount 1605 may remain stationary in a room, or even to be anchored to the floor in the room, and the bed 1602 with the patient is maneuvered into place relative to mount 1605 with the radar sensor 1604 situated above the patient's torso.

Figure 16:
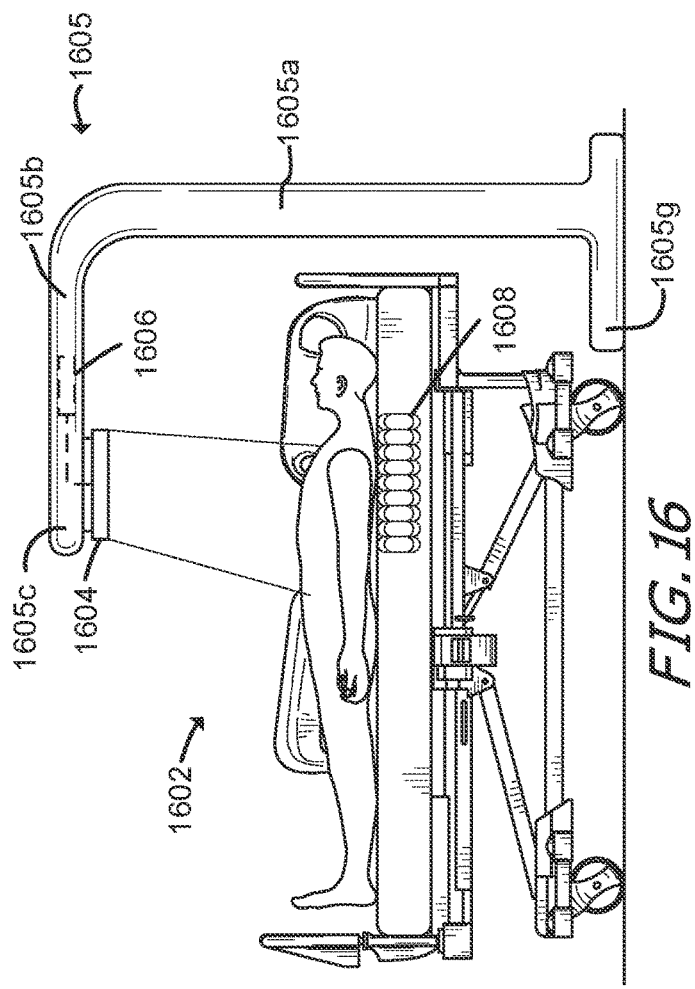
FIG. 16 is a side view of one embodiment of a system for monitoring a patient's position using one or more radar sensors.

Still referring to FIG. 16, the patient bed 1602 also includes one or more percussion and vibration (P & V) bladders 1608 that can rapidly inflate and deflate, causing P & V on the area of the patient above the P & V bladders 1608. P & V treatment may be used to loosen and expel secretions that collect in the lungs of pulmonary patients.

The radar sensor 1604 can be used to monitor the position of the patient, and the P & V bladders 1608 that are under the patient's chest can be selected for the P & V therapy. Additionally or alternatively, in some embodiments, the radar sensor 1604 may monitor the magnitude of the vibration of the patient's chest caused by the P & V bladders 1608. The magnitude of the vibrations of the P & V bladders 1608 can be tuned to cause an optimized vibration level of the patient's chest. In some embodiments, the patient bed 1602 may include P & V bladders 1608 and rotation bladders 1408. The rotation bladders 1408 may be used to properly position the patient over the P & V bladders 1608 for P & V therapy.

Figure 17:
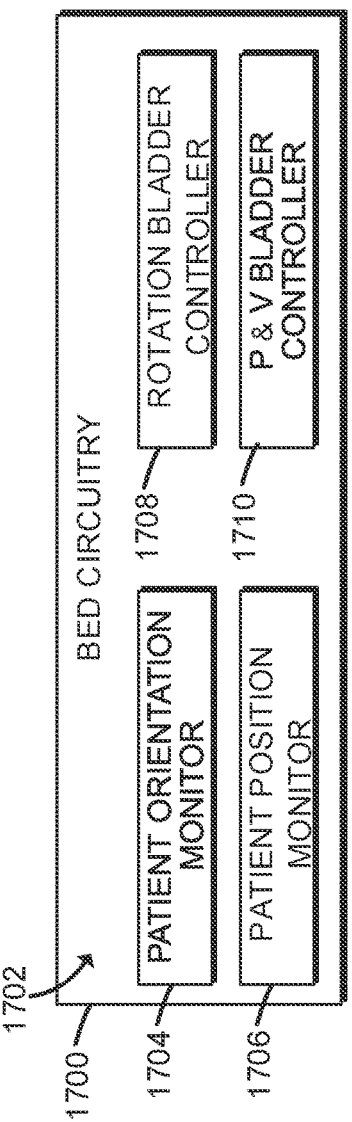
FIG. 17 is an environment that may be established by bed circuitry of the systems of FIG. 14, 15, or 16.

Referring now to FIG. 17, in an illustrative embodiment, bed circuitry 1700, which may be an embodiment of bed circuitry 1406 and/or bed circuitry 1606, establishes an environment 1702 during operation. The illustrative environment 1702 includes a patient orientation monitor 1704, a patient position monitor 1706, a rotation bladder controller 1708, and a P & V bladder controller 1710. The various modules of the environment 1702 may be embodied as hardware, software, firmware, or a combination thereof. For example, the various modules, logic, and other components of the environment 1702 may form a portion of, or otherwise be established by, a processor, memory, or other hardware components of the bed circuitry 1700. As such, in some embodiments, one or more of the modules of the environment 1702 may be embodied as circuitry or collection of electrical devices (e.g., a patient orientation monitor 1704, a patient position monitor 1706, a rotation bladder controller 1708, etc.). It should be appreciated that, in such embodiments, one or more of the circuits (e.g., the patient orientation monitor 1704, the patient position monitor 1706, the rotation bladder controller 1708, etc.) may form a portion of one or more of the processor, the memory, the data storage, and/or other components of the bed circuitry 1700. Additionally, in some embodiments, one or more of the illustrative modules may form a portion of another module and/or one or more of the illustrative modules may be independent of one another. Further, in some embodiments, one or more of the modules of the environment 1702 may be embodied as virtualized hardware components or emulated architecture, which may be established and maintained by the processor or other components of the bed circuitry 1700.

The patient orientation monitor 1704, which may be embodied as hardware, firmware, software, virtualized hardware, emulated architecture, and/or a combination thereof as discussed above, is configured to monitor the orientation of the patient on a patient bed with use of one or more radar sensors. The patient orientation monitor 1704 may monitor whether the patient is supine, prone, one the patient's side, etc. The patient orientation monitor 1704 saves the patient orientation data over time, allowing for determination of how long a patient has been lying in the same orientation. The orientation determined by the patient orientation monitor 1704 may be used as feedback for controlling the rotation bladders 1408 and/or the P & V bladders 1608.

The patient position monitor 1706, which may be embodied as hardware, firmware, software, virtualized hardware, emulated architecture, and/or a combination thereof as discussed above, is configured to monitor the position of the patient on a patient bed with use of one or more radar sensors. The patient position monitor 1706 may monitor the position of the patient, such as where the patient is on the patient bed and where the patient is relative to the rotation bladders 1408 and/or the P & V bladders 1608. The position determined by the patient position monitor 1706 may be used as feedback for controlling the rotation bladders 1408 and/or the P & V bladders 1608.

The rotation bladder controller 1708, which may be embodied as hardware, firmware, software, virtualized hardware, emulated architecture, and/or a combination thereof as discussed above, is configured to control the rotation bladders 1408. The rotation bladder controller 1708 may determine when a rotation is necessary, such as by determining that the patient has been lying on the same side for an amount of time that is past a threshold amount of time. The threshold may be any suitable value, such as any time between 30 minutes and 5 hours, for example. In the illustrative embodiment, the threshold is 2 hours. In some embodiments, the rotation bladder controller 1708 may determine where the patient is on the patient bed, and control the rotation bladders 1408 that will cause the patient to rotate from their current position. For example, the rotation bladder controller 1708 may cause the rotation bladders that are under the right side of the patient to inflate. In some embodiments, the rotation bladder controller 1708 may control the rotation bladders 1408 to cause the patient to move position, which may be done to, e.g., position the patient over a desired portion of the rotation bladders 1408 and/or the P & V bladders 1608.

The P & V bladder controller 1710, which may be embodied as hardware, firmware, software, virtualized hardware, emulated architecture, and/or a combination thereof as discussed above, is configured to control the P & V bladders 1608. The P & V bladder controller 1710 may determine when P & V therapy is necessary, such as by determining that the patient has not had P & V therapy for an amount of time that is past a threshold amount of time. The threshold may be any suitable value, such as any time between 30 minutes and 24 hours. In the illustrative embodiment, the threshold is 2 hours. In some embodiments, the time threshold may be determined based on a patient's symptoms. In some embodiments, P & V therapy may be determined to be necessary based on the symptoms of the patient. The P & V therapy may be initiated based on the patient's symptoms and/or the threshold time for performing P & V therapy may be set based on the symptoms of the patient.

To perform P & V therapy, the P & V bladder controller 1710 monitors the position of the patient. If necessary, the P & V bladder controller 1710 can move the patient to be located over the P & V bladders 1608. Additionally or alternatively, in some embodiments, the P & V bladder controller 1710 may select the P & V bladders 1608 that are under the current position of the patient. The P & V bladder controller 1710 may then perform P & V therapy by inflating and deflating the selected P & V bladders 1608. In some embodiments, the P & V bladder controller 1710 may monitor the amplitude of the vibrations of the patient, such as by using radar sensors. The amplitude of the inflation and deflation of the P & V bladders 1608 may be controlled based on the measured amplitude of the vibrations of the patient, forming a "closed loop" for the P & V therapy.

Figure 18:
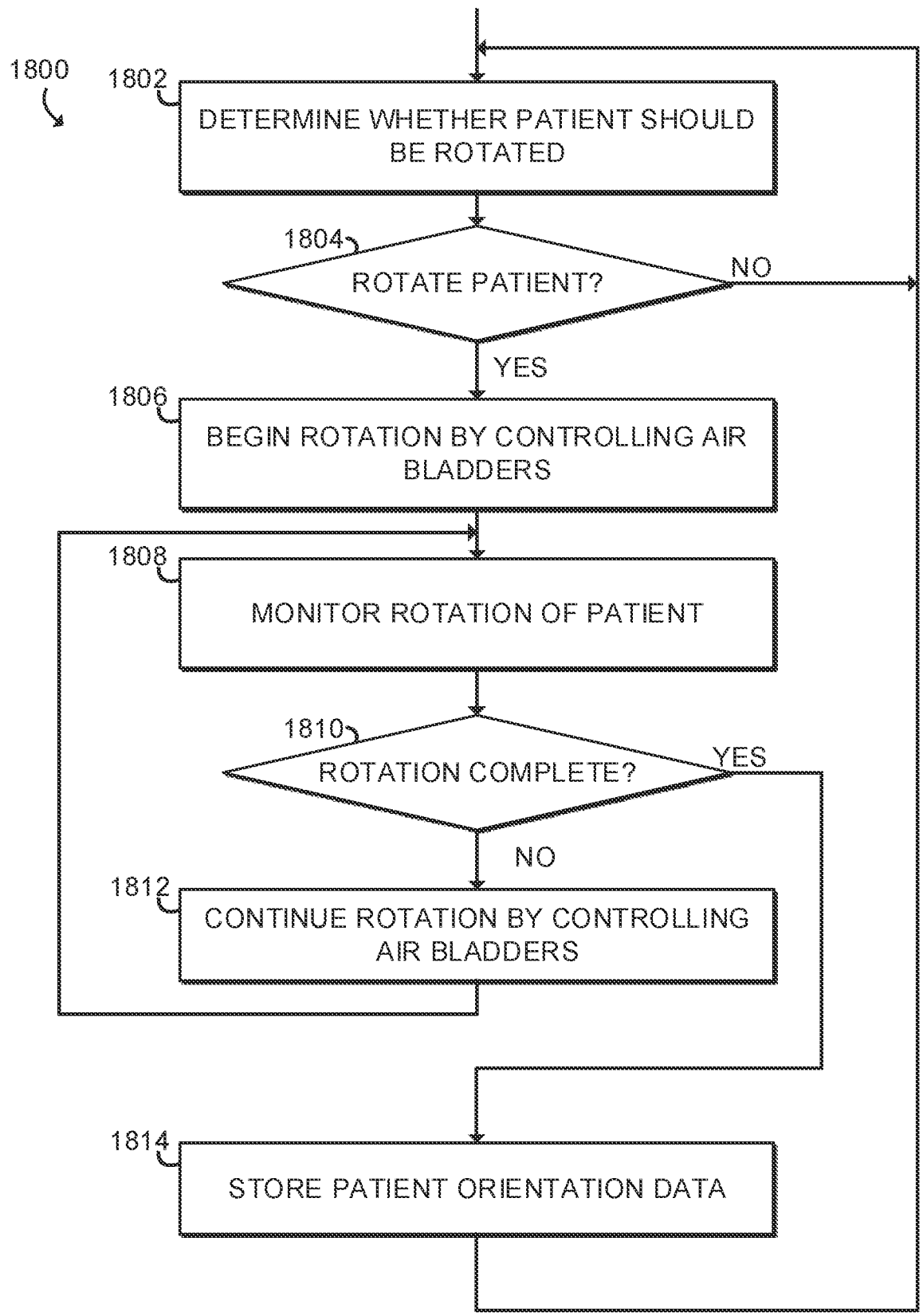
FIG. 18 is a flowchart for one embodiment of a method to monitor patient position that may be executed by the system of FIG. 14, 15, or 16.

Referring now to FIG. 18, in use, a method 1800 for rotating a patient may be performed. In some embodiments, some or all of the method 1800 may be performed by the bed circuitry 1700. Additionally or alternatively, in some embodiments, certain portions of the method 1800 may be performed a person, such as a caregiver of the patient. For example, the bed circuitry 1700 may indicate that a patient has changed orientation for a certain period of time, and a caregiver may rotate the patient in response to that indication. In another example, a caregiver may determine that a patient needs to be rotated and may initiate the rotation by the bed circuitry 1700. The method 1800 begins in block 1802, in which the bed circuitry 1700 determines whether the patient should be rotated. In the illustrative embodiment, the bed circuitry 1700 determines whether the patient should be rotated based on whether the patient has changed orientation in a predetermined period of time, such as the last two hours. The bed circuitry 1700 may determine whether the patient has changed orientation based on data from one or more radar sensors.

In block 1804, if the patient is not to be rotated, the method 1800 loops back to block 1802 to determine whether the patient should be rotated. If the patient is to be rotated, the method proceeds to block 1806, in which the rotation bladders 1408 under one side of the patient are inflated. The rotation bladders 1408 to be inflated may be selected based on a position of the patient that can be determined based on one or more radar sensors. It should be appreciated that, in some embodiments, the patient may be rotated by deflating the rotation bladders 1408, such as when the patient has already been rotated by inflation of the rotation bladders 1408.

In block 1808, the rotation of the patient is monitored. In some embodiments, the rotation of the patient is monitored with use of one or more radar sensors. In block 1810, if the rotation is not complete, the method 1800 proceeds to block 1812 to continue the rotation by controlling the rotation bladders 1408. If the rotation is complete, the method 1800 proceeds to block 1814, in which the patient orientation data is stored. The method 1800 then loops back to block 1802 to determine whether the patient should be rotated.

Figure 19:
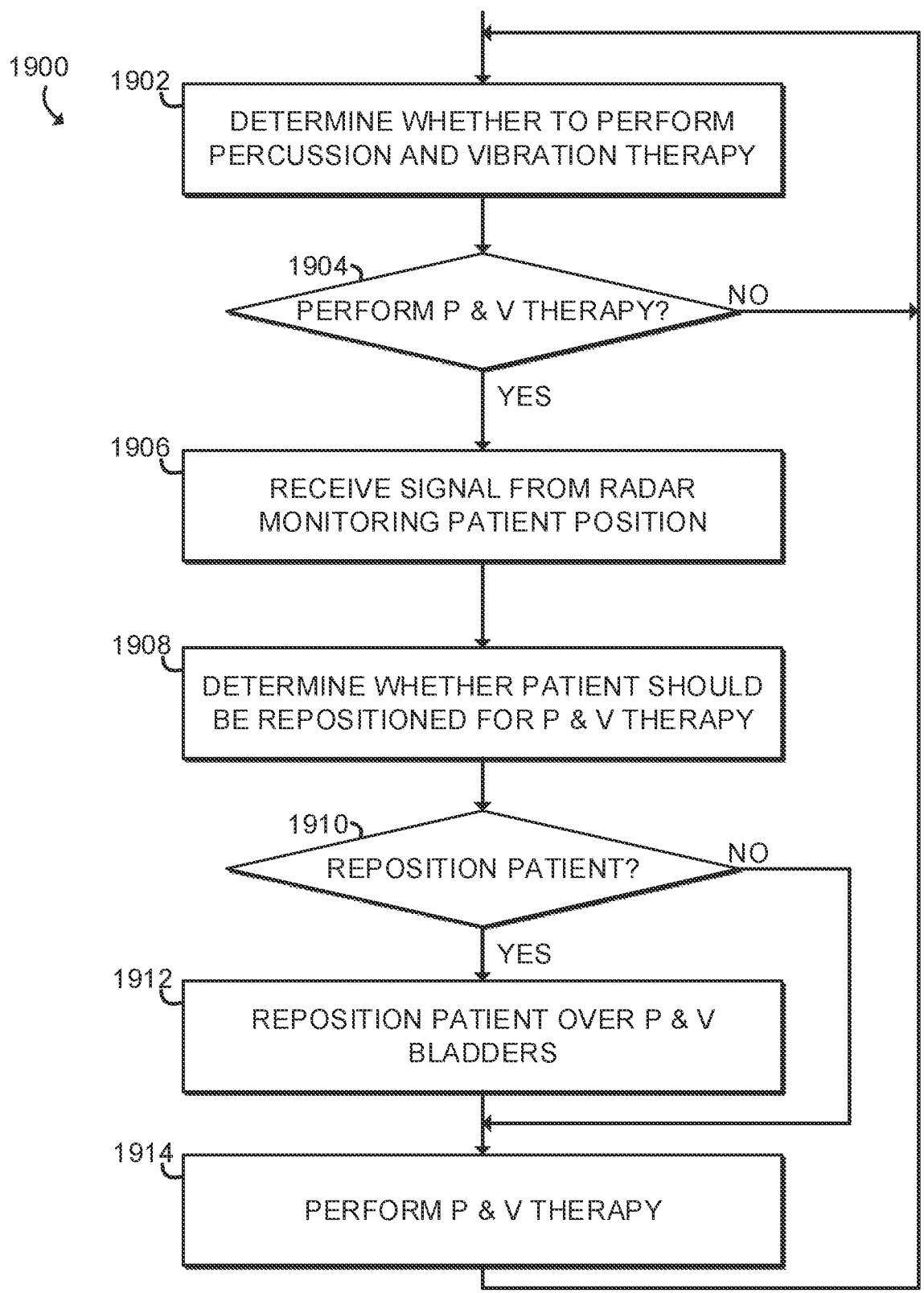
FIG. 19 is a flowchart for one embodiment of a method to perform percussion and vibration (P & V) therapy on a patient.

Referring now to FIG. 19, in use, a method 1900 for performing P & V therapy on a patient may be performed. In some embodiments, some or all of the method 1900 may be performed by the bed circuitry 1700. Additionally or alternatively, in some embodiments, certain portions of the method 1900 may be performed a person, such as a caregiver of the patient. For example, a caregiver may determine that P & V therapy should be performed, and the bed circuitry 1700 perform P & V therapy. The method 1900 begins in block 1902, in which the bed circuitry 1700 determines whether to perform P & V therapy. The bed circuitry 1700 may determine whether P & V therapy is to be performed by determining that the patient has not had P & V therapy for an amount of time that is past a threshold amount of time. The threshold may be any suitable value, such as any time between 30 minutes and 24 hours. In the illustrative embodiment, the threshold is 2 hours. In some embodiments, the threshold may be determined based on a patient's symptoms. In some embodiments, P & V therapy may be determined to be necessary based on the symptoms of the patient. The P & V therapy may be initiated based on the patient's symptoms and/or the threshold time for performing P & V therapy may be set based on the symptoms of the patient.

In block 1904, if P & V therapy is not to be performed, the method 1900 loops back to block 1902 to determine whether P & V therapy should be performed. If P & V therapy is to be performed, the method 1900 continues to block 1906, in which the bed circuitry 1700 receives a signal from a radar sensor monitoring a position of the patient. In block 1908, the bed circuitry 1700 determines whether the patient should be repositioned for P & V therapy. For example, the bed circuitry 1700 may determine that the patient should be positioned over the P & V bladders 1608 prior to beginning the P & V therapy.

In block 1910, if the patient is to be repositioned, the method proceeds to block 1912 to reposition the patient over the P & V bladders 1608. In the illustrative embodiment, other bladders such as the rotation bladders 1408 may be used to reposition the patient.

After the patient is repositioned, or if no repositioning is required, the method 1900 proceeds to block 1914, where the bed circuitry 1700 performs P & V therapy. The bed circuitry 1700 performs P & V therapy by rapidly inflating and deflating the P & V bladders 1608. In some embodiments, the bed circuitry 1700 may monitor the amplitude of the vibrations of the patient, such as by using radar sensors. The amplitude of the inflation and deflation of the P & V bladders 1608 may be controlled based on the measured amplitude of the vibrations of the patient, forming a "closed loop" for the P & V therapy. After the P & V therapy is performed, the method loops back to block 1902 to determine whether further P & V therapy is needed.

Figure 20A:
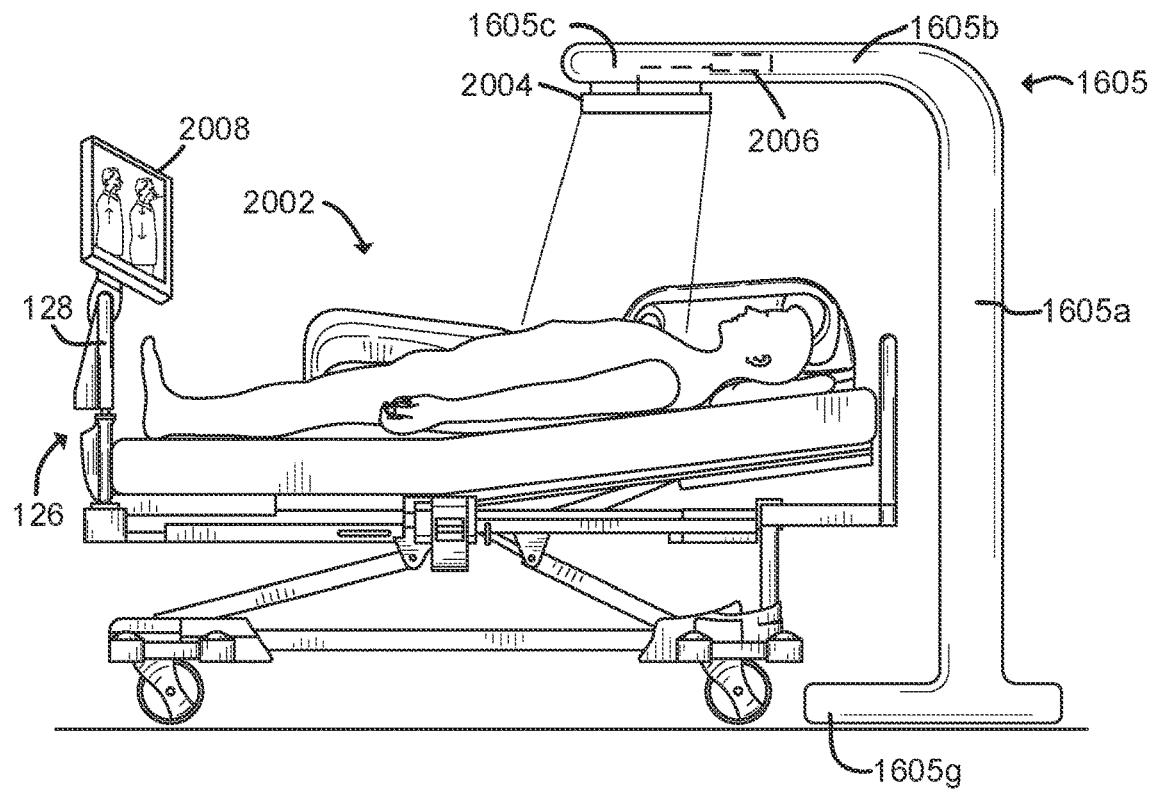
FIG. 20A is a side view of a system for performing breathing exercises with radar monitoring.

Referring now to FIG. 20A, in one embodiment, a patient bed 2002 includes one or more radar sensors 2004 connected to bed circuitry 2006. Furthermore, the embodiment of FIG. 20A includes radar support mount 1605 which was discussed above in connection with FIG. 16 and so the same reference numbers are used in FIG. 20A to denote portions of mount 1605. The patient bed 2002 also has a display 2008 positioned on footboard 128 at the foot end 126 of the bed 2002, visible to the patient. In use, the bed circuitry 2006 executes a program for helping the patient perform breathing exercises, such as by presenting on the display 2008 breathing exercises for the patient to perform. The breathing exercises may be any suitable exercises, such as exercises for breathing deeply, exercises for properly performing belly breathing as opposed to chest breathing, etc. The breathing of the patient can be monitored using the radar sensor 2004, allowing for feedback that can be provided to the bed circuitry 2006. In some embodiments, the breathing exercises can be "gamified," such as by allowing a user to earn points or achievements based on time spent performing exercises or results obtained. The breathing exercises may be done while the patient is supine, siting up, or in any other suitable position.

Figure 20B:
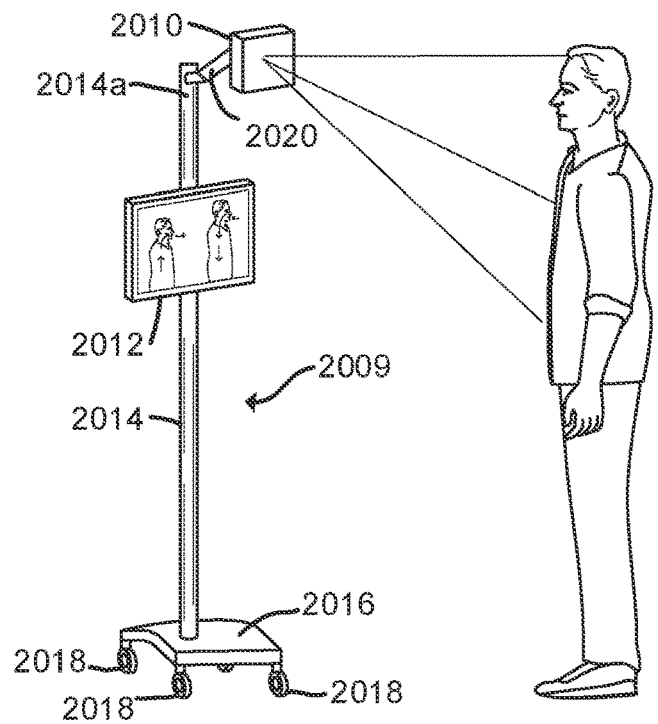
FIG. 20B is a perspective view of an alternative system for performing breathing exercises with radar monitoring.

It should be appreciated that use of radar sensors as feedback in performing breathing exercises is not limited to patients that are in a patient bed. For example, as shown in FIG. 20B, in one embodiment, a radar sensor 2010 and a display 2012 are mounted on a mobile breathing exercise device 2009, allowing for a patient to perform breathing exercises while standing up, sitting, etc., in any suitable location. Mobile breathing exercises device 2009 is similar to radar unit 902 which was discussed above in connection with FIG. 9. Thus, device 2009 includes a wheeled base 2016 having casters 2018 coupled thereto. Mobile radar unit 2009 further includes a generally vertically oriented pole or mast 2014 extending upwardly from base 2016. A pivotable arm 2020 extends from an upper region 2014a of pole 2014 and radar sensor 2010 is mounted to a distal end of arm 2020 in spaced relation with pole 2014. Arm 2020 is pivotable upwardly and downwardly relative to pole 2014 to adjust a height at which radar sensor 2010 is supported above the floor.

In some embodiments, arm 2020 is movable vertically along pole 2014 to provide further adjustment of the vertical position of radar sensor 2010 relative to the floor. For example, a lockable and releasable collar may be coupled to pole 2014 and arm 2020 may extend from the collar. When released, the collar is movable upwardly and downwardly along pole 2014 and then lockable in the desired position. A clamp, lock, thumb screw, or similar releasable locking device is provided in some embodiments for locking the collar relative to pole 2014. A similar collar and locking device may be provided for coupling display 2012 to pole 2014 thereby to allow for vertical adjustment of display 2012 along pole 2014. Radar unit 2010 on mobile breathing exercise device 2009 is well suited for obtaining patient breathing data from patients who are standing up such as may be the case during a medical examination at a doctor's office or during a therapy session with a respiratory therapist, for example.

Figure 21:
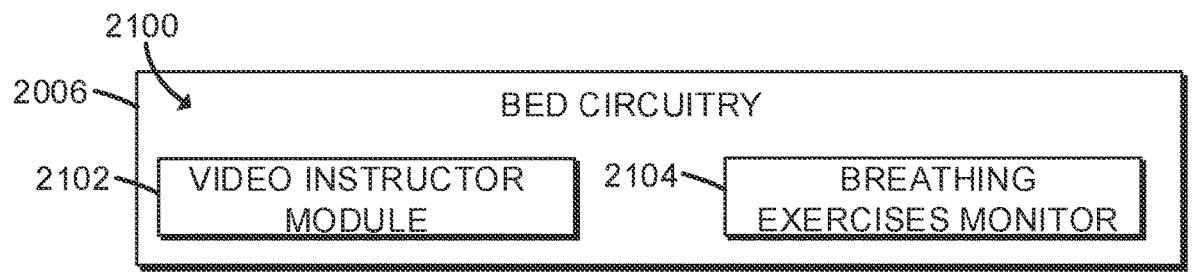
FIG. 21 is an environment that may be established by bed circuitry of the systems of FIG. 20A or 20B.

Referring now to FIG. 21, in an illustrative embodiment, bed circuitry 2006 establishes an environment 2100 during operation. The illustrative environment 2100 includes a video instructor module 2102 and a breathing exercises monitor 2104. The various modules of the environment 2100 may be embodied as hardware, software, firmware, or a combination thereof. For example, the various modules, logic, and other components of the environment 2100 may form a portion of, or otherwise be established by, a processor, memory, or other hardware components of the bed circuitry 2006. As such, in some embodiments, one or more of the modules of the environment 2100 may be embodied as circuitry or collection of electrical devices (e.g., a video instructor circuit 2102, a breathing exercises monitor circuit 2104, etc.). It should be appreciated that, in such embodiments, one or more of the circuits (e.g., the video instructor circuit 2102, the breathing exercises monitor circuit 2104, etc.) may form a portion of one or more of the processor, the memory, the data storage, and/or other components of the bed circuitry 2006. Additionally, in some embodiments, one or more of the illustrative modules may form a portion of another module and/or one or more of the illustrative modules may be independent of one another. Further, in some embodiments, one or more of the modules of the environment 2100 may be embodied as virtualized hardware components or emulated architecture, which may be established and maintained by the processor or other components of the bed circuitry 2006.

The video instructor module 2102, which may be embodied as hardware, firmware, software, virtualized hardware, emulated architecture, and/or a combination thereof as discussed above, is configured to provide video instructions for breathing exercises to a patient. The breathing exercises may be any suitable exercises, such as exercises for breathing deeply, exercises for properly performing belly breathing as opposed to chest breathing, etc. In some embodiments, the breathing exercises can be "gamified," such as by allowing a user to earn points or achievements based on time spent performing exercises or results obtained. The breathing exercises may be done while the patient is supine, siting up, or in any other suitable position.

The breathing exercises monitor 2104, which may be embodied as hardware, firmware, software, virtualized hardware, emulated architecture, and/or a combination thereof as discussed above, is configured to monitor the patient's breathing during the breathing exercises. The breathing exercises monitor 2104 may use one or more radar sensors to monitor a chest, belly, and/or other parts of the patient to determine breathing parameters of the patient, such as how deeply the patient is breathing, whether the patient is doing belly breathing or chest breathing, etc.

Figure 22:
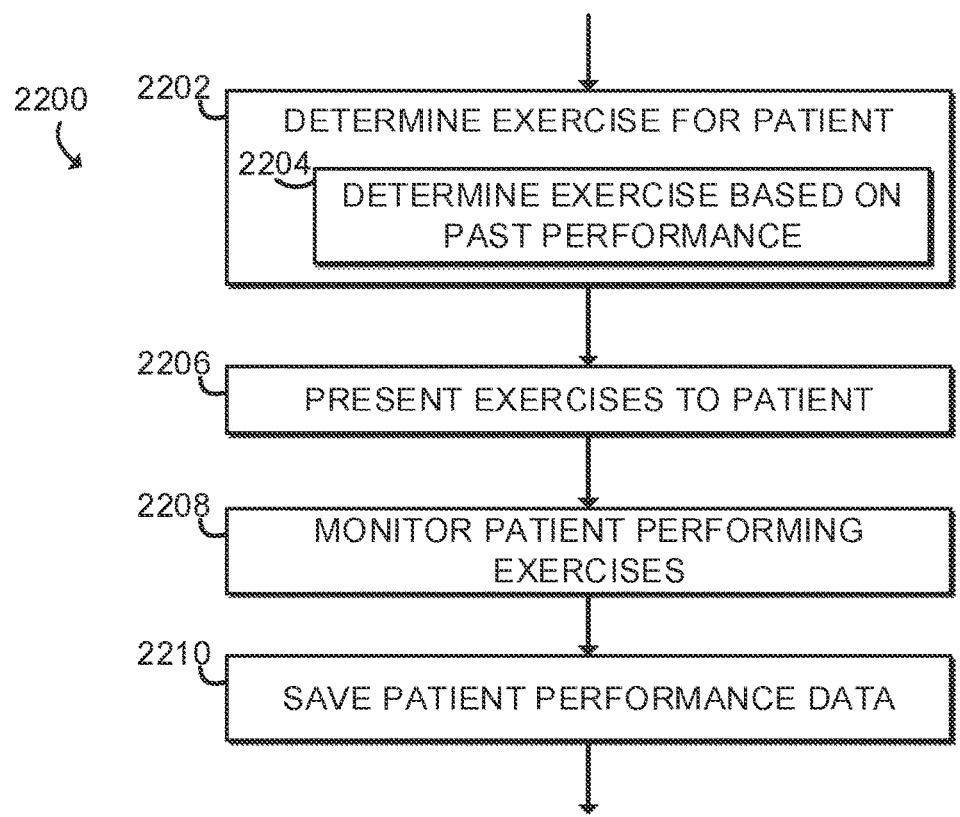
FIG. 22 is a flowchart for one embodiment of a method to guide a patient to perform breathing exercises.

Referring now to FIG. 22, in use, a method 2200 for facilitating monitored breathing exercises by a patient may be performed. In some embodiments, some or all of the method 2200 may be performed by the bed circuitry 2006. Additionally or alternatively, in some embodiments, certain portions of the method 2200 may be performed by a person, such as a caregiver of the patient. For example, a caregiver may determine what breathing exercises should be done and configure the bed circuitry 2006 to instruct the patient to perform those breathing exercises. The method 2200 begins in block 2202, in which the bed circuitry 2006 determines a breathing exercise for a patient. The bed circuitry 2006 may determine the breathing exercise in any suitable way, such as based on symptoms of the patient, a configuration of a caregiver, etc. In some embodiments, in block 2204, the bed circuitry 2006 may determine an exercise based on past performance of the patient. For example, if the patient successfully completed 10 minutes of breathing exercises previously, the bed circuitry 2006 may determine that 12 minutes of breathing exercises should be done.

In block 2206, the bed circuitry 2006 presents one or more instructions of the exercise to the patient. For example, a video of a person or avatar may be presented on a display, such as display 2008 or display 2012, and the user may be instructed to follow along with breathing in, breathing out, taking deep breaths, etc. In block 2208, the bed circuitry 2006 monitors the patient performing the breathing exercises based on data acquired by radar sensor 2004 or radar sensor 2010, for example. It should be appreciated that, in the illustrative embodiment, the bed circuitry 2006 provides the patient's performance as feedback. For example, if a patient is not breathing deeply enough or is chest breathing instead of belly breathing, the bed circuitry 2006 may notify the patient and instruct the patient on how to correctly perform the breathing exercises. Such a notification appears on display 2008 or display 2012 in some embodiments.

In block 2210, the bed circuitry 2006 saves the patient performance data for the breathing exercises. The patient performance data may be used to monitor a patient's progress, to develop a treatment plan, to determine future breathing exercises, etc.

Figure 23:
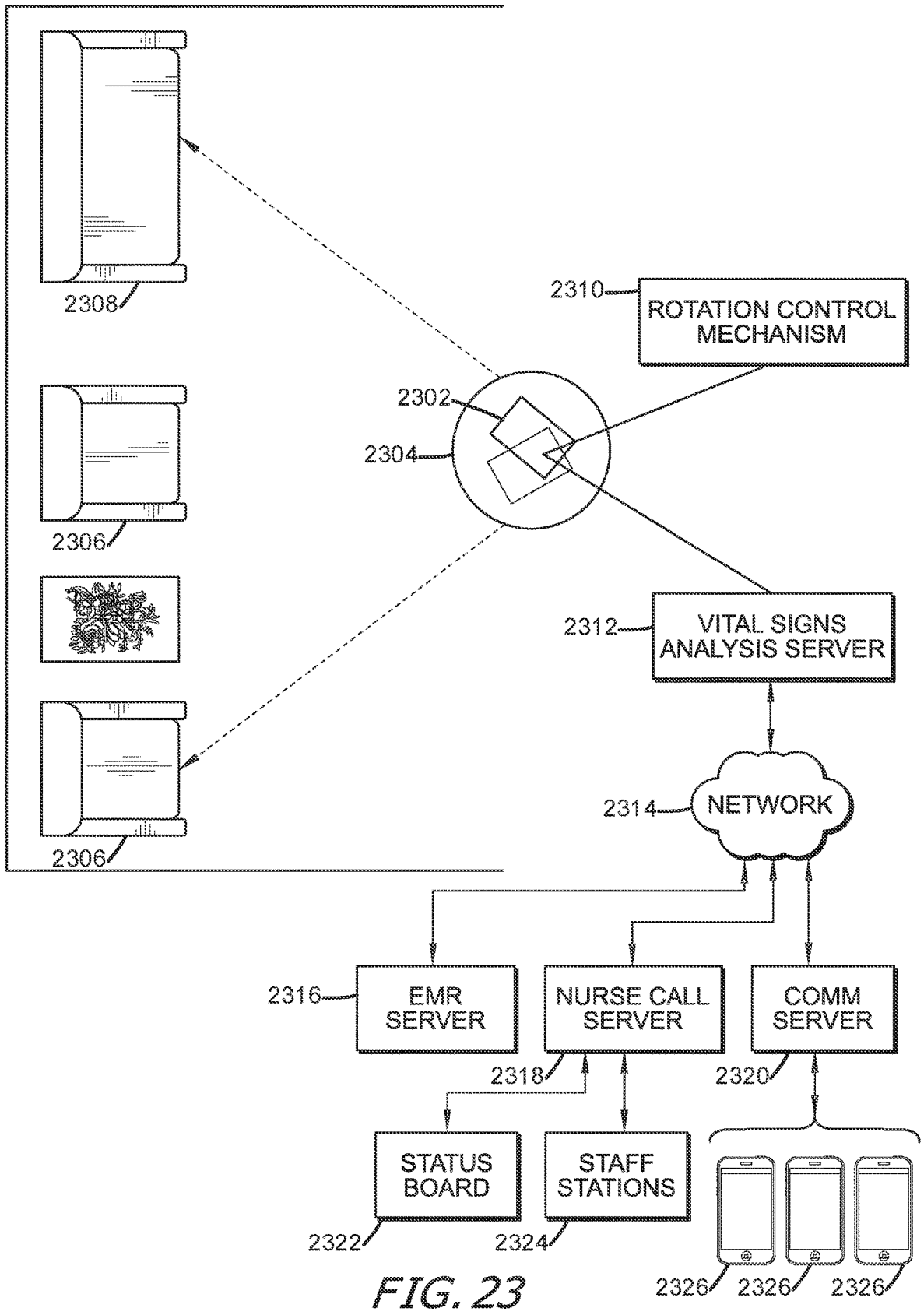
FIG. 23 is a top view of a system for monitoring patients in a waiting area and a simplified block diagram of circuitry of the system.

Referring now to FIG. 23, in one embodiment, one or more radar sensors 2302 may be present in a location such as a hospital waiting room or waiting area. In the illustrative embodiment, as described in more detail below, the one or more radar sensors 2302 may be used to monitor vital signs of patients in a waiting room, such as heart rate, respiration, etc. In some embodiments, the one or more radar sensors 2302 may be on a one or two axis mount, allowing the orientation of the one or more radar sensors 2302 to change to point in different directions. A rotation control mechanism 2310 can control the orientation of the one or more radar sensors to direct them at various areas of the room, such as at various chairs 2306, couches, 2308, etc. and more particularly, to direct them at patients seated on the chairs 2306 and couches 2308. In some embodiments, rotation control mechanism 2310 comprises a motorized gimbal having movable gimbal frame elements to which the one or more radar sensors 2302 are mounted. Other mechanisms 2310 may include movable linkages, arms, shafts and the like that are movable by a motor to aim radar sensor(s) 2302 at the chairs 2306, couches 2308, etc.

The one or more radar sensors 2302 are directly or indirectly connected to a vital signs analysis server 2312 using one or more wired or wireless communication means. The vital signs analysis server 2312 may monitor the vital signs of the patients on chairs 2306 and couches 2308 or patients otherwise in the waiting area and may determine if the vital signs are such that intervention is warranted.

The vital signs analysis server 2312 may be connected over a network 2314 to additional components, such as an electronic medical records server 2316, a nurse call system 2318, a communication server 2320, a status board 2322, staff stations 2324, and one or more mobile compute devices

2326. In use, vital signs analysis server 2312 may communicate monitoring information of the patient to other components over the network 2314. For example, the vital signs analysis server 2312 may monitor the heart rate of a patient and send the heartrate of the patient to the electronic medical records server 2316 to be stored as part of the medical record of the patient. The vital signs analysis server 2312 may also send the heartrate of the patient to the nurse call system 2318, allowing the heartrate to be presented on a status board 2322, staff stations 2324, and/or sent to mobile compute devices 2326 carried by caregivers.

In many instances, the identity of the patients seated on chairs 2306 and couches 2308 in the waiting area are not known because the patients may choose to sit at any open seat and/or may not yet have been admitted into the healthcare facility. Accordingly, in some embodiments, a seat location identification (ID) is assigned to each seating area of chairs 2306 and couches 2308 and stored in server 2312. If intervention is warranted, the seat location ID is presented on an appropriate display of one or more of servers 2312, 2316, 2318, 2320 or devices 2322, 2324, 2326, for example, along with the vital signs data causing the alert notification to occur. A caregiver can then attend to the patient sitting or otherwise located at the area designated by the seat location ID. Thus, use of radar sensors 2302 to monitor patients in waiting areas assists caregivers in triaging and prioritizing the patients for medical attention.

Figure 24:
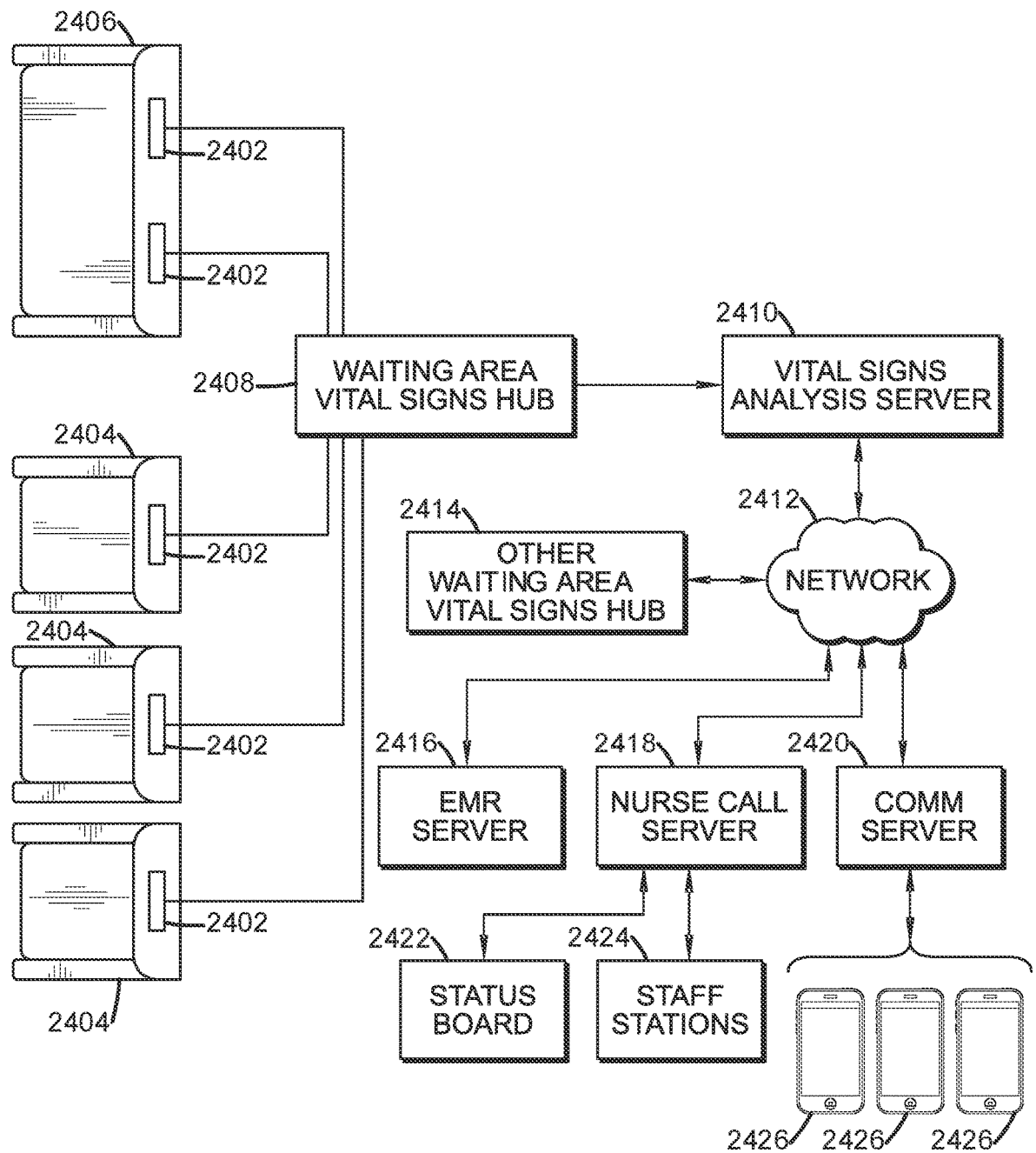
FIG. 24 is a top view of an alternative system for monitoring patients in a waiting area and a simplified block diagram of circuitry of the system.

Referring now to FIG. 24, in one embodiment, one or more radar sensors 2402 may be present on one or more chairs 2404 and/or couches 2406 in a room such as a hospital waiting room. In the illustrative embodiment, as described in more detail below, the one or more radar sensors 2402 may be used to monitor vital signs of patients in a waiting room, such as heart rate, respiration, etc. In the illustrative example, radar sensors 2402 are situated within the backrests of chairs 2404 and couches 2406 so that the radar sensors are aimed at the torsos of patients seated on chairs 2404 and couches 2406.

The one or more radar sensors 2402 are directly or indirectly connected to a waiting area vital signs hub 2408 using one or more wired or wireless communication means. The waiting area vital signs hub 2408 may pass data from the one or more radar sensors 2402 indirectly or directly to a vital signs analysis server 2410 using one or more wired or wireless communication means. The vital signs analysis server 2410 may monitor the vital signs of the patients and may determine if the vital signs are such that intervention is warranted.

Similar to the vital signs analysis server 2312, the vital signs analysis server 2410 may be connected over a network 2412 to additional components, such as one or more other waiting area vital signs hubs 2414, an electronic medical records server 2416, a nurse call server 2418, a communication server 2420, a status board 2422, staff stations 2424, and one or more mobile compute devices 2426. In use, vital signs analysis server 2410 may communicate monitoring information of the patient to other components over the network 2412. Each of the components in FIG. 24 may operate in a similar manner as the corresponding component in FIG. 23, which will not be repeated in the interest of clarity. Moreover, seat location ID's may be assigned to each of the seating locations of chairs 2404 and 2406 and stored in hub 2408 and/or server 2410 in the same manner as discussed above in connection with the embodiment of FIG. 23.

Figure 25:
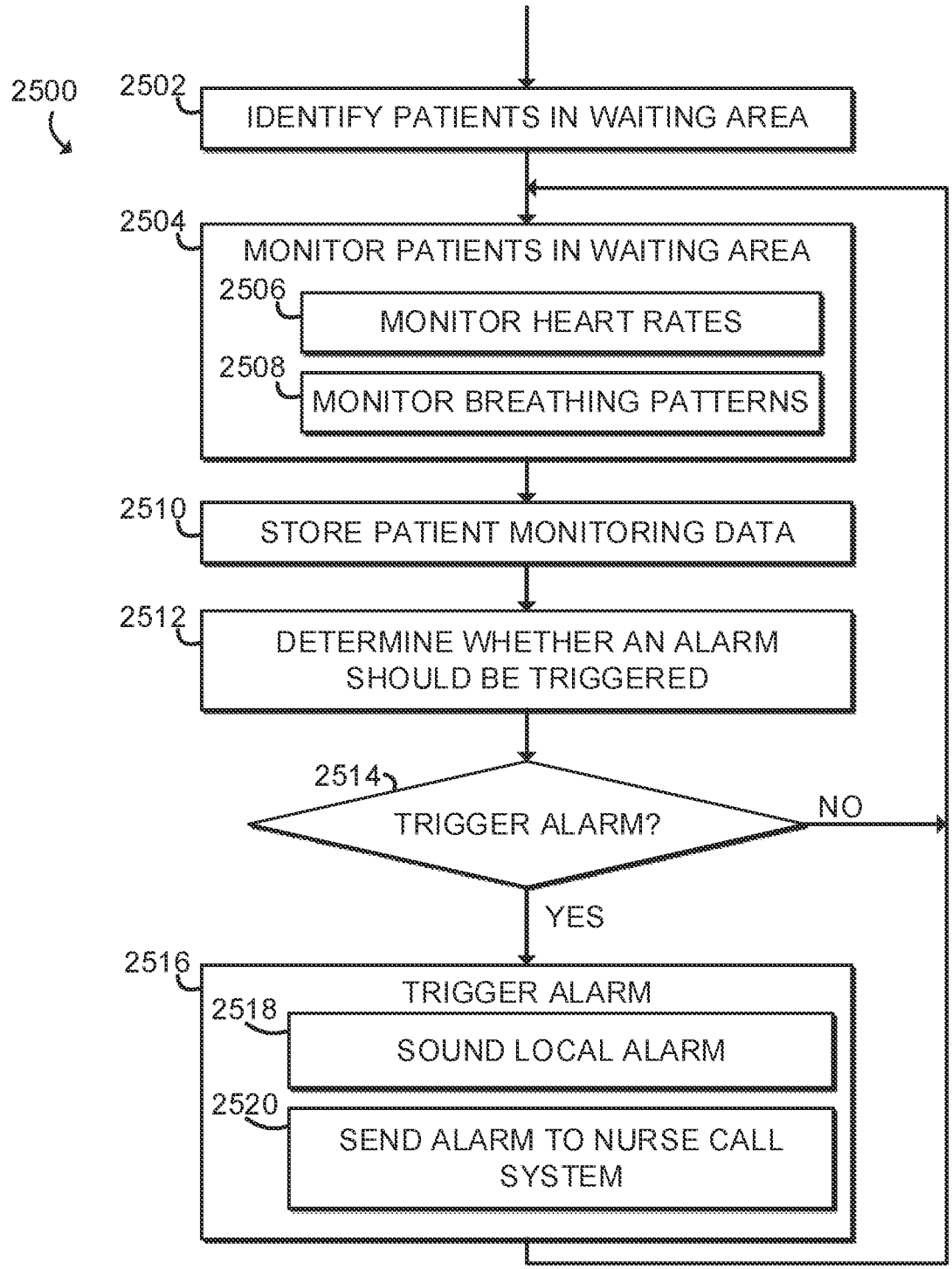
FIG. 25 is a flowchart for one embodiment of a method to monitor patients in a waiting area.

Referring now to FIG. 25, in use, a method 2500 for monitoring patients in a waiting area may be performed. In some embodiments, some or all of the method 2500 may be performed by a vital signs analysis server, such as the vital signs analysis server 2312 and/or the vital signs analysis server 2410. Additionally or alternatively, in some embodiments, certain portions of the method 2500 may be performed a person, such as a caregiver of the patient. For example, a vital signs analysis server may present patient vital signs to a caregiver, and a caregiver may determine that action should be taken, such as treating the patient or triggering an alarm. The method 2500 begins in block 2502, in which the vital signs analysis server identifies patients in a waiting area. The vital signs analysis server may identify patients in any suitable manner, such as by using one or more radar sensors, image processing from images from a camera, identification of patients provided by a caregiver, identification of patients from other sensors, etc. In some embodiments, patients may be provided with a radiofrequency identification (RFID) tag that can be used to track and/or identify the patient. Alternatively or additionally, the monitoring of patients at block 2504 is done in connection with the seat location ID's such that block 2502 is omitted in some embodiments.

In block 2504, the vital signs analysis server monitors patients or seat locations in a waiting area using data from one or more radar sensors. In block 2506, the vital signs analysis server monitors a heart rate of each of the identified patients or seat locations. In block 2508, the vital signs analysis sever monitors breathing patterns of each of the identified patients or seat locations. It should be appreciated that, in some embodiments, data from the radar sensors may be analyzed for chest mobility and breathing patterns in a similar manner as described above in regard to, e.g., blocks 1004-1022 in FIG. 10A, which will not be repeated in the interest of clarity. Additionally or alternatively, in some embodiments, different vital signs may be monitored.

In block 2510, the vital signs analysis server stores patient monitoring data. The vital signs analysis server may store patient monitoring data for a short time, such as for as long as the patient is in the waiting area or at the hospital, or the vital signs analysis server may store patient monitoring data for longer, such as by storing the patient monitoring data in an electronic medical record associated with the patient if the identity of the patient is known. Otherwise, the vital signs analysis server associates the vital signs data with the seat location and stores the vital signs data at least for as long as a particular patient is at the seat location.

In block 2512, the vital signs analysis server determines whether the vital signs of the patient indicates that an alarm should be triggered. The vital signs analysis server may be configured to trigger an alarm based on any suitable measurement of the patient's vital signs. For example, an alarm may be triggered if the heart rate is too high or, too low, or matches a pattern of a problematic heart rate. An alarm may also be triggered if a problematic breathing pattern or chest expansion is detected.

In block 2514, if an alarm is not to be triggered, the method 2500 loops back to block 2504 to continue monitoring patients in the waiting area. If the alarm is to be triggered, the method 2500 proceeds to block 2516, in which the vital signs analysis server triggers an alarm. The vital signs analysis server may trigger a local alarm, such as by making a local visible or audible alarm, in block 2518. Additionally or alternatively, the vital signs analysis server may trigger a remote alarm, such as by sending an alarm to the nurse call system in block 2520. The alarm may result in a message being displayed on a status board, a message being sent to one or more mobile compute devices of caregivers, etc. The method 2500 then loops back to block 2504 to continue monitoring patients in the waiting area.

Figure 26:
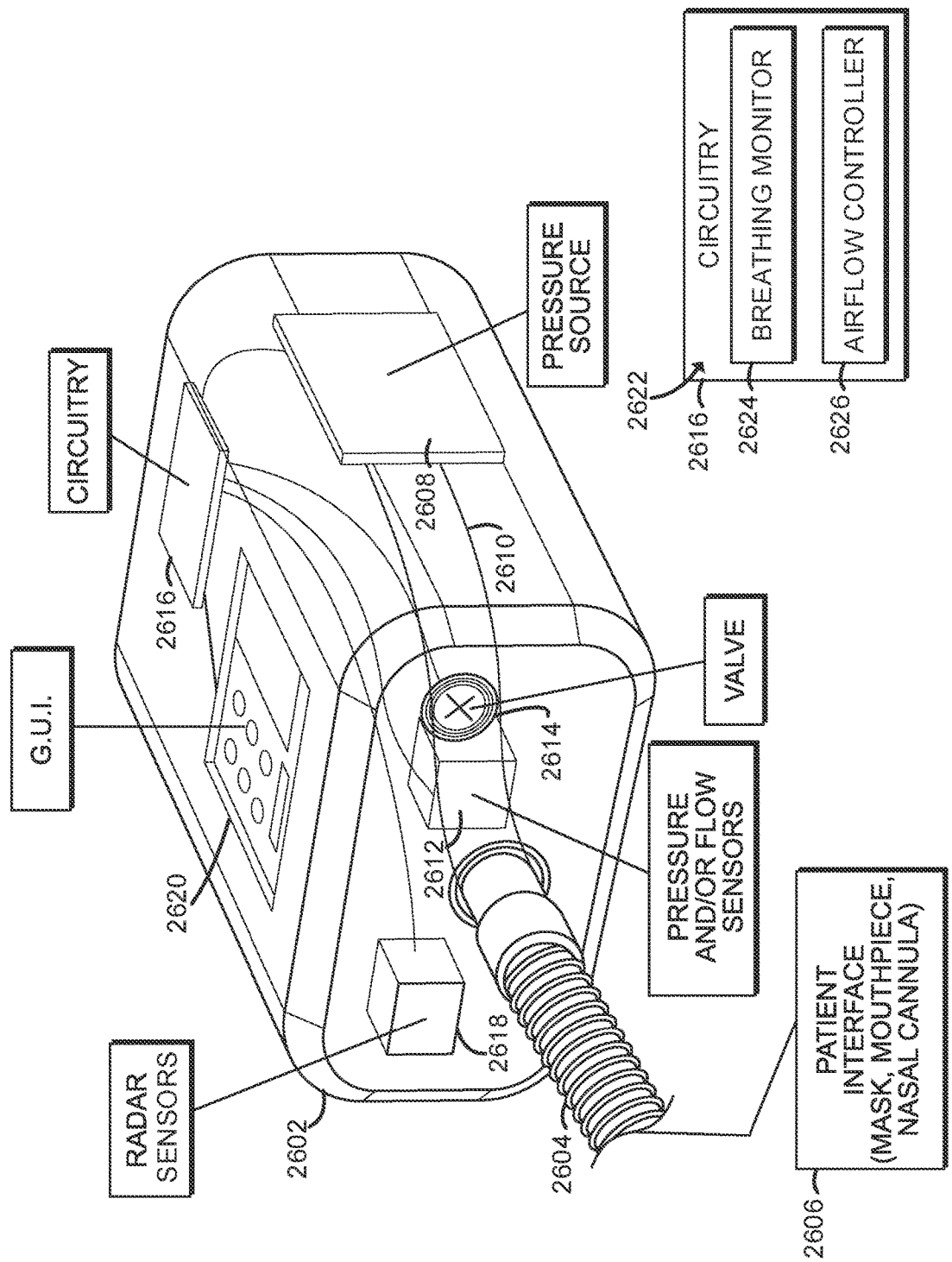
FIG. 26 is one embodiment of a device for providing pressurized air to a patient.

Referring now to FIG. 26, a breathing therapy system 2602 can provide various types of breathing therapy, such as continuous positive airway pressure (CPAP) and/or cough assistance such as mechanical insufflation/exsufflation (MIE) therapy. The breathing therapy system 2602 includes tubing 2604 that can be connected to a patient interface 2606, such as a mask, mouthpiece, nasal cannula, etc. A pressure source 2608 is connected to the external tubing 2604 through internal tubing 2610. The pressure and/or flow in the tubing 2604, 2610 can be monitored by one or more pressure and/or flow sensors 2612. A valve 2614 can be used to control the air flow and/or pressure delivered to tubing 2604 from the pressure source 2608. Circuitry 2616 controls the breathing therapy system 2602. The circuitry 2616 can be connected to the pressure source 2608, the valve 2614, the pressure and/or flow sensors 2612, and one or more radar sensors 2618. In use, the one or more radar sensors 2618 can be used to monitor a user's breathing pattern, allowing the breathing therapy system 2602 to synchronize air flow with the user's breathing (e.g., inhalation and exhalation), as described in more detail below. The circuitry 2616 may also be connected to a graphical user interface (GUI), which may include one or more buttons, one or more switches, a display, and/or the like.

In use, the circuitry 2616 establishes an environment 2622 during operation. The illustrative environment 2622 includes a breathing monitor 2624 and an airflow controller 2626. The various modules of the environment 2622 may be embodied as hardware, software, firmware, or a combination thereof. For example, the various modules, logic, and other components of the environment 2622 may form a portion of, or otherwise be established by, a processor, memory, or other hardware components of the circuitry 2616. As such, in some embodiments, one or more of the modules of the environment 2622 may be embodied as circuitry or collection of electrical devices (e.g., breathing monitor circuitry 2624, airflow controller circuitry 2626, etc.). It should be appreciated that, in such embodiments, one or more of the circuits (e.g., the breathing monitor circuitry 2624, the airflow controller circuitry 2626, etc.) may form a portion of one or more of a processor, a memory, a data storage, and/or other components of the circuitry 2616. Additionally, in some embodiments, one or more of the illustrative modules may form a portion of another module and/or one or more of the illustrative modules may be independent of one another. Further, in some embodiments, one or more of the modules of the environment 2622 may be embodied as virtualized hardware components or emulated architecture, which may be established and maintained by the processor or other components of the circuitry 2616.

The breathing monitor 2624, which may be embodied as hardware, firmware, software, virtualized hardware, emulated architecture, and/or a combination thereof as discussed above, is configured to monitor the breathing of the user of the breathing therapy system 2602 with use of one or more radar sensors 2618. The breathing monitor 2624 may monitor a breathing frequency, a breathing phase, a point in a user's breathing pattern, etc. For example, the breathing monitor 2624 may determine when a user is beginning to inhale, is done inhaling, is beginning to exhale, and is done exhaling. In some embodiments, the breathing monitor 2624 may determine when a user has taken a large breath in, which may indicate that the user is going to cough.

The airflow controller 2626, which may be embodied as hardware, firmware, software, virtualized hardware, emulated architecture, and/or a combination thereof as discussed above, is configured to control the airflow of the breathing therapy system 2602 into and out of the tubing 2604. In the illustrative embodiment, the airflow controller 2626 provides a positive pressure to the tubing 2604 when a patient is breathing in, providing positive airway pressure to assist in breathing in. When a patient is breathing out, the airflow controller 2626 may provide a negative pressure or may not provide any pressure at all. In some embodiments, the airflow controller 2626 may be configured to assist a user with a cough. The airflow controller 2626 may assist a user with a cough when a beginning of a cough is detected or when an external indication (such as a button press on the GUI 2620) is provided. A beginning of a cough may be detected by a large inhale, a tensing of the upper chest, a pause in airflow, and/or the beginning of a rapid exhale. When a cough is detected, the airflow controller 2626 can provide a strong, brief negative airflow, assisting the user of the breathing therapy system 2602 with the cough. Thus, by equipping breathing therapy system 2602 with one or more radar sensors 2618, circuitry 2622 is able to synchronize the operation of pressure source 2608, which may be a blower in some embodiments, and valve 2614 with the patient's breathing pattern by controlling pressure source 2608 and valve 2614 based on an inspiratory trigger and/or an expiratory trigger determined from data acquired by the radar sensor(s) 2618.

Figure 27:
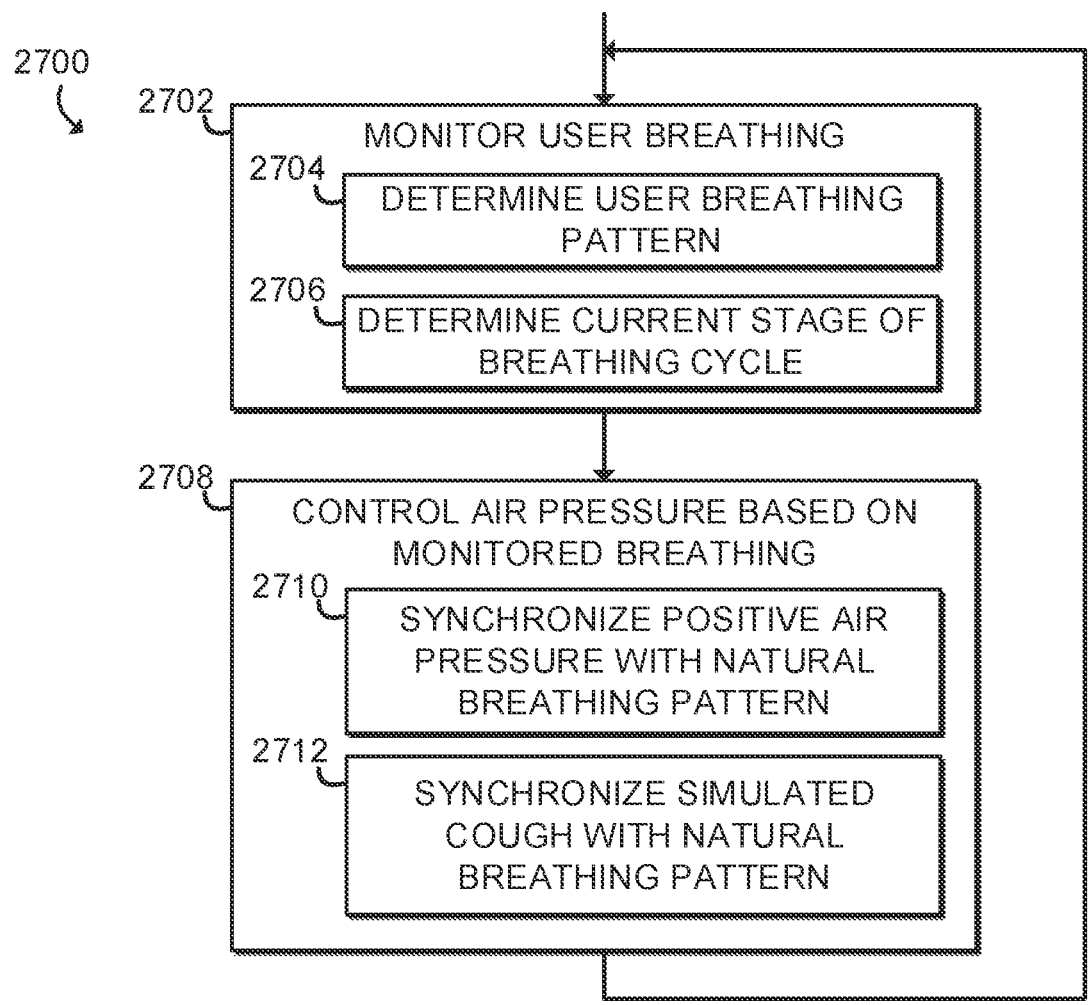
FIG. 27 is a flowchart for one embodiment of a method of providing pressurized air to a patient that may be performed by the device of FIG. 26.

Referring now to FIG. 27, in use, a method 2700 for breath therapy of a patient may be performed. In some embodiments, some or all of the method 2700 may be performed by circuitry 2616 of a breathing therapy system 2602. Additionally or alternatively, in some embodiments, certain portions of the method 2700 may be performed a person, such as a caregiver of the patient. The method 2700 begins in block 2702, in which the circuitry 2616 monitors the breathing of a user of the breathing therapy system 2602 using data from one or more radar sensors 2618. The circuitry 2616 may determine a user breathing pattern in block 2704. The circuitry 2616 may determine a current stage of the breathing cycle of the user in block 2706, such as whether the user is beginning to inhale, is done inhaling, is beginning to exhale, or is done exhaling. In some embodiments, the circuitry 2616 may determine when a user has taken a large breath in, which may indicate that the user is going to cough.

In block 2708, the circuitry 2616 controls the air pressure and/or air flow delivered to the tubing 2604 based on the monitored breathing. In the illustrative embodiment, the circuitry 2616 provides a positive pressure to the tubing 2604 when a patient is breathing in, providing positive airway pressure to assist in breathing in. When a patient is breathing out, the circuitry 2616 may provide a negative pressure or may not provide any pressure at all. In some embodiments, the circuitry 2616 may be configured to assist a user with a cough. The circuitry 2616 may assist a user with a cough when a beginning of a cough is detected or when an external indication (such as a button press on the GUI 2620) is provided. A beginning of a cough may be detected by a large inhale, a tensing of the upper chest, a pause in airflow, and/or the beginning of a rapid exhale. When a cough is detected, the circuitry 2616 can provide a strong, brief negative airflow, assisting the user of the breathing therapy system 2602 with the cough. The method 2700 then returns to block 2702 to continue monitoring the user's breathing.

Figure 28:
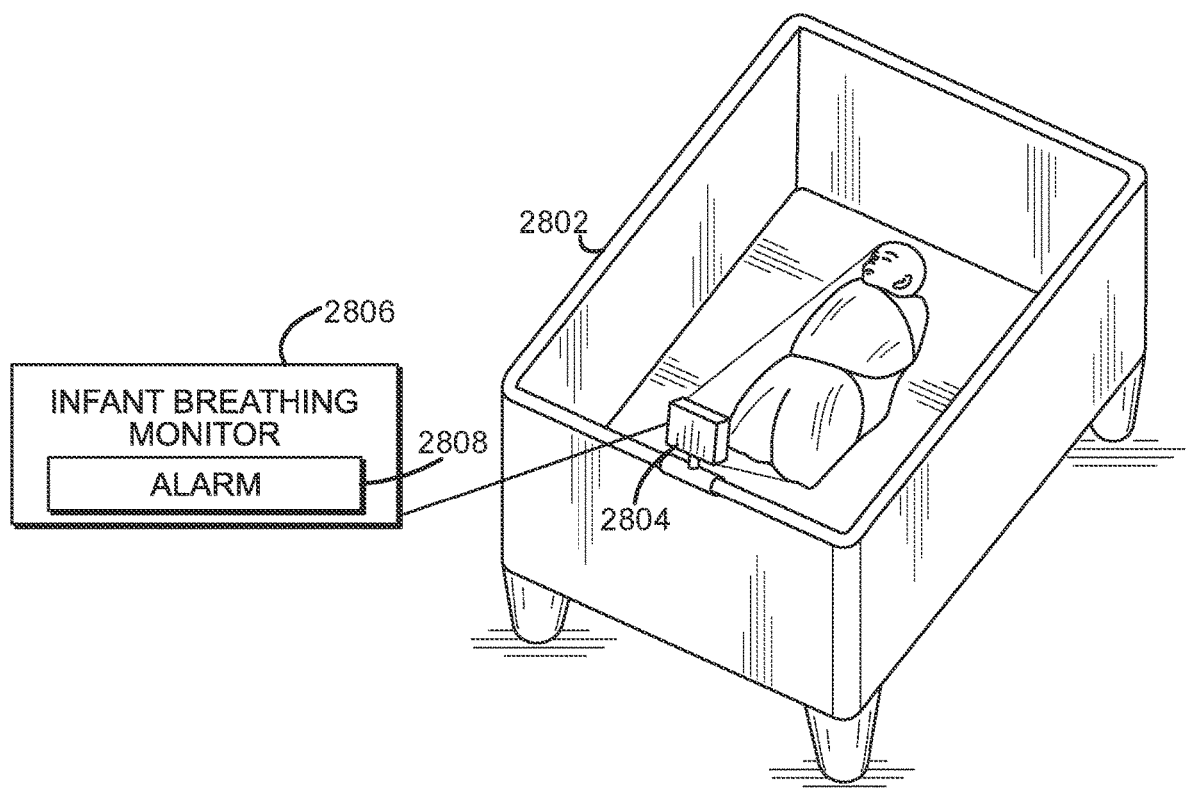
FIG. 28 is a perspective view of a system for monitoring an infant breathing.

Referring now to FIG. 28, in one embodiment, a crib 2802 has a radar sensor 2804 mounted on it, monitoring an infant supported by the crib 2802. The radar sensor 2408 is connected to an infant breathing monitor 2806. The infant breathing monitor 2806 includes circuitry that uses the radar sensor 2408 to monitor the infant's breathing. If the infant's breathing stops, suggesting a possible episode of sudden infant death syndrome (SIDS), the circuitry can trigger an alarm 2808 of the infant breathing monitor 2806, alerting a parent or other caregiver to check on the infant.

Figure 29:
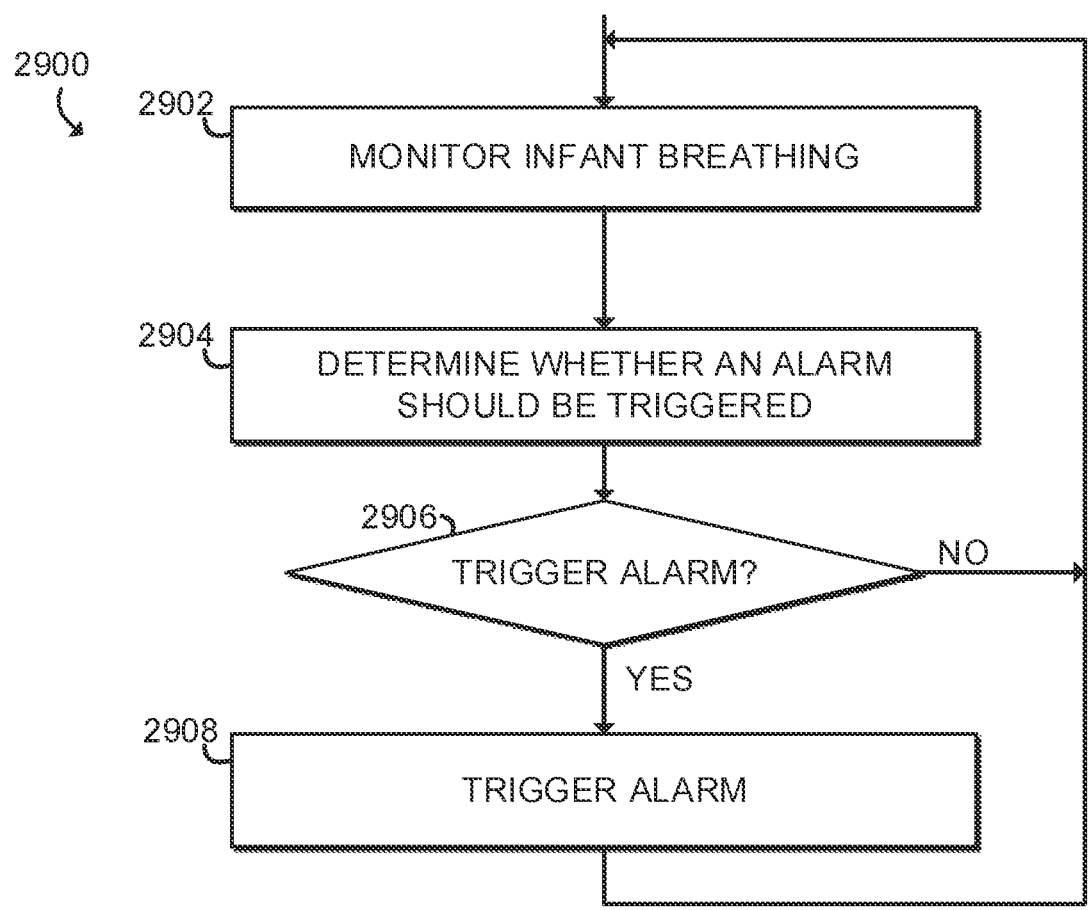
FIG. 29 is a flowchart for one embodiment of a method of monitoring an infant breathing that may be performed by the system of FIG. 28.

Referring now to FIG. 29, in use, the infant breathing monitor 2806 can execute a method 2900 for monitoring an infant breathing. The method 2900 begins in block 2902, in which the infant breathing monitor 2806 monitors the breathing of the infant in the crib 2802 using one or more radar sensors 2804.

In block 2904, the infant breathing monitor 2806 determines whether an alarm should be triggered. In the illustrative embodiment, an alarm should be triggered if the infant has stopped breathing for a predetermined amount of time, such as any time from 10-30 seconds to give one arbitrary range of possible time thresholds.

In block 2906, if an alarm should not be triggered, the method 2900 loops back to block 2902 to continue monitoring the breathing of the infant. If the alarm should be triggered, the method 2900 proceeds to block 2908, in which the infant breathing monitor 2806 triggers an alarm. The infant breathing monitor 2806 may trigger an alarm in any suitable manner, such as by sounding an audible or visible alarm or sending a message to a remote device such as a baby monitor. The method 2900 then loops back to block 2902 to continue monitoring the breathing of the infant.

The discussion of bed 102 of FIG. 1 and its various component parts is equally applicable to beds 500, 802, 1102, 1402, 1602, 2002 of FIGS. 5, 8, 11, 14 and 15, 16, and 20A, respectively, unless specifically noted otherwise.

Although certain illustrative embodiments have been described in detail above, variations and modifications exist within the scope and spirit of this disclosure as described and as defined in the following claims.

The invention claimed is:

1. A system for monitoring movement of a patient, the system comprising:
   one or more radar sensors configured to:
      transmit a radar signal towards a patient on a patient bed; and
      receive a reflection of the radar signal from the patient, and
   circuitry comprising a patient position monitor to:
      receive data from the one or more radar sensors indicative of the reflection of the radar signal from the patient; and
      determine a position parameter of the patient, wherein the position parameter is indicative of a location or orientation of the patient on the patient bed,
      wherein the circuitry further comprises a percussion and vibration (P & V) bladder controller to: determine, based on the position parameter, a subset of a plurality of P & V bladders of the patient bed to inflate in order to perform P & V therapy on the patient, wherein the selected subset of the plurality of P & V bladders are P &V bladders under a current position of the patient; and send a signal to inflate the subset of the plurality of P & V bladders,
      wherein the one or more radar sensors are further configured to: transmit an additional radar signal towards the patient during the P & V therapy; and receive a reflection of the additional radar signal from the patient, and wherein the P & V bladder controller is further configured to: receive additional data from the one or more radar sensors indicative of the reflection of the additional radar signal from the patient; determine, based on the additional data from the one or more radar sensors, an amplitude of vibration of the patient caused by the P & V therapy; and adjust a signal sent to inflate the subset of the plurality of P & V bladders based on the amplitude of vibration of the patient.

2. The system of claim 1, wherein the circuitry further comprises a rotation bladder controller to determine whether the patient should be rotated based on the position parameter of the patient.

3. The system of claim 2, wherein to determine whether the patient should be rotated comprises to determine that the patient has not been rotated for at least a threshold amount of time.

4. The system of claim 1, wherein the circuitry further comprises a rotation bladder controller configured to: determine, based on the position parameter, a subset of a plurality of rotation bladders of the patient bed to inflate in order to rotate the patient; and send a signal to inflate the subset of the plurality of rotation bladders.

5. The system of claim 1, wherein the circuitry further comprises a rotation bladder controller to: determine, based on the position parameter, a subset of a plurality of rotation bladders of the patient bed to inflate in order to move the patient towards a center of the patient bed; and send a signal to inflate the subset of the plurality of rotation bladders.

6. The system of claim 1, wherein the P & V bladder controller is further to: determine, based on the position parameter, a subset of a plurality of rotation bladders of the patient bed to inflate in order to move the patient towards a center of the patient bed; and send a signal to inflate the subset of the plurality of rotation bladders to move the patient towards the center of the patient bed prior to sending the signal to inflate the subset of the plurality of P & V bladders.

7. The system of claim 1, further comprising a mast having an upstanding portion and an arm extending from the upstanding portion in a cantilevered manner and wherein the one or more radar sensors are connected to the arm of the mast, the arm being arranged to overlie the patient.

8. The system of claim 7, wherein the one or more radar sensors are movable relative to the arm.

9. The system of claim 1, wherein the radar signal has a frequency between 30 and 300 gigahertz.

10. The system of claim 1, wherein the one or more radar sensors comprises a first radar sensor arranged to detect a first position of a first portion of the patient, a second radar sensor arranged to detect a second position of a second portion of the patient, and a third radar sensor arranged to detect a third position of a third portion of the patient.

11. The system of claim 10, wherein the first and second radar sensors are movable relative to the patient in a lateral dimension of the patient.

12. The system of claim 11, wherein the third radar sensor is movable relative to the patient in a longitudinal dimension of the patient.

13. The system of claim 10, further comprising a mast having an upstanding portion and an arm extending from the upstanding portion in a cantilevered manner so as to overlie the patient and wherein the first, second, and third radar sensors are coupled to the arm.

14. The system of claim 13, wherein the first, second, and third radar sensors are individually movable relative to the arm.

15. The system of claim 13, further comprising a patient bed and wherein the mast is coupled to an upper frame assembly at a head end of the patient bed.

16. The system of claim 15, wherein the patient bed further includes a display that is operable under the control of the circuitry to show information sensed by the one or more radar sensors.

17. The system of claim 16, wherein the display is also configured to display user inputs for control of functions of the patient bed.

18. The system of claim 17, wherein the functions of the patient bed that are controllable by the user inputs on the display include functions of components associated with a mattress of the patient bed and movement of portions of a frame of the patient bed.

* * * * *